(12) United States Patent
Ohya et al.

(10) Patent No.: US 9,477,875 B2
(45) Date of Patent: Oct. 25, 2016

(54) CELL MONITORING DEVICE, CELL MONITORING METHOD AND PROGRAM THEREOF

(71) Applicant: Japan Science and Technology Agency, Kawaguchi-shi, Saitama (JP)

(72) Inventors: Yoshikazu Ohya, Tokyo (JP); Shigeyuki Kawano, Tokyo (JP); Satoru Nogami, Tokyo (JP); Shinsuke Ohnuki, Tokyo (JP); Shuhei Ota, Tokyo (JP); Koichi Watanabe, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 14/647,904

(22) PCT Filed: Nov. 27, 2013

(86) PCT No.: PCT/JP2013/081894
§ 371 (c)(1),
(2) Date: May 28, 2015

(87) PCT Pub. No.: WO2014/084255
PCT Pub. Date: Jun. 5, 2014

(65) Prior Publication Data
US 2015/0302237 A1 Oct. 22, 2015

(30) Foreign Application Priority Data
Nov. 28, 2012 (JP) .................................. 2012-259880

(51) Int. Cl.
*G06K 9/00* (2006.01)
*G06T 7/00* (2006.01)
(Continued)

(52) U.S. Cl.
CPC .............. *G06K 9/0014* (2013.01); *C12M 1/34* (2013.01); *C12Q 1/02* (2013.01); *G01N 21/27* (2013.01);
(Continued)

(58) Field of Classification Search
None
See application file for complete search history.

(56) References Cited

U.S. PATENT DOCUMENTS

2006/0285743 A1  12/2006  Oh et al.
2009/0213214 A1   8/2009  Yamada
(Continued)

FOREIGN PATENT DOCUMENTS

GB    2 433 985 A       7/2007
JP    2007-097584 A     4/2007
(Continued)

OTHER PUBLICATIONS

Lu Fan et al., "Effect of Temperature and Irradiance on Growth of *Haematococcus pluvialis* (Chlorophyceae)", Journal of Phycology, vol. 30, pp. 829-833 (1994), Phycological Society of America.
(Continued)

*Primary Examiner* — Weiwen Yang
(74) *Attorney, Agent, or Firm* — Amster, Rothstein & Ebenstein LLP

(57) ABSTRACT

A cell monitoring device includes an outline detecting section that detects edge pixels from a cell image in a captured image of cells arranged in a single layer and generates an edge image including the detected edge pixels; a pigmented region detecting section that detects pixels of a pigmented region of the cell image in the captured image, and generates a pigmented region image including the detected pixels of the pigmented region; and an image merging section that, in a merged image obtained by overlaying the edge image and the pigmented region image together, detects a cell image region and a background image region in the captured image based on the pixel intensity variance and thus detects the cell image region in the captured image.

8 Claims, 38 Drawing Sheets

(51) Int. Cl.
  G06T 7/60    (2006.01)
  C12M 1/34    (2006.01)
  C12Q 1/02    (2006.01)
  G01N 21/27   (2006.01)
  G06T 11/60   (2006.01)

(52) U.S. Cl.
  CPC ......... *G06K 9/00147* (2013.01); *G06T 7/0016* (2013.01); *G06T 7/0081* (2013.01); *G06T 7/602* (2013.01); *G06T 11/60* (2013.01); *G06T 2207/10024* (2013.01); *G06T 2207/10056* (2013.01); *G06T 2207/30024* (2013.01)

(56) References Cited

U.S. PATENT DOCUMENTS

| | | | | |
|---|---|---|---|---|
| 2010/0291575 | A1* | 11/2010 | Shamah | G01N 33/5044 435/6.16 |
| 2012/0014608 | A1 | 1/2012 | Watanabe | |
| 2013/0194410 | A1* | 8/2013 | Topman | G06K 9/0014 348/79 |

FOREIGN PATENT DOCUMENTS

| | | | |
|---|---|---|---|
| JP | 2009-175334 | A | 8/2009 |
| JP | 2010-063403 | A | 3/2010 |
| JP | 2011-030494 | A | 2/2011 |
| JP | 2012-021904 | A | 2/2012 |
| WO | 02/067195 | A2 | 8/2002 |

OTHER PUBLICATIONS

Yoram Hoffman et al., "Isolation and characterization of a novel chytrid species (phylum Blastocladiomycota), parasitic on the green alga *Haematococcus*", Mycological Research, 112, pp. 70-81 (2008), Elsevier Ltd.

T-M. Enari, E.B.C. "Analytica Microbiologica", Journal of the Institute of Brewing, vol. 83, pp. 109-118, Mar.-Apr. 1977, John Wiley & Sons, Inc.

Serena Rasconi et al., "Use of Calcofluor White for Detection, Identification, and Quantification of Phytoplanktonic Fungal Parasites", Applied and Environmental Microbiology, vol. 75, No. 8, pp. 2545-2553 (2009), American Society for Microbiology.

Jenia Gutman et al., "Evidence for the involvement of surface carbohydrates in the recognition of *Haematococcus pluvialis* by the parasitic blastoclad Paraphysoderma sedebokerensis", Fungal Biology, vol. 115, pp. 803-811 (2011), Elsevier B.V.

John Canny, "A Computational Approach to Edge Detection", IEEE Transactions on Pattern Analysis and Machine Intelligence, vol. PAMI-8, No. 6, pp. 679-698 (Nov. 1986).

Nobuyuki Otsu, "A Threshold Selection Method from Gray-Level Histograms", IEEE Transactions on Systems, Man, and Cybernetics, vol. SMC-9, No. 1, pp. 62-66 (Jan. 1979).

Serge Beucher, "Watersheds of functions and picture segmentation", Acoustics, Speech, and Signal Processing, IEEE International Conference on ICASSP '82., vol. 7, pp. 1928-1931 (1982).

Alexander Toshev et al., "Object Detection via Boundary Structure Segmentation", The Twenty-Third IEEE Conference on Computer Vision and Pattern Recognition, pp. 950-957 (2010).

Sandesh B. Kamath et al., "Digital image processing—an alternate tool for monitoring of pigment levels in cultured cells with special reference to green alga *Haematococcus pluvialis*", Biosensors and Bioelectronics, vol. 21, Issue 5, pp. 768-73, (2005), Elsevier B.V.

Chia-Hung Su et al., "Simultaneous Estimation of Chlorophyll a and Lipid Contents in Microalgae by Three-Color Analysis", Biotechnology and Bioengineering, vol. 99, No. 4, pp. 1034-1039 (2008), Wiley Periodicals, Inc.

Aaron M. Collins et al., "Carotenoid Distribution in Living Cells of *Haematococcus pluvialis* (Chlorophyceae)", PLoS One, vol. 6, Issue 9, e24302 (Sep. 2011), PLOS.

Shinsuke Ohnuki et al., "Image-Based Monitoring System for Green Algal *Haematococcus pluvialis* (Chlorophyceae) Cells during Culture", Plant and Cell Physiology, vol. 54, Issue 11, pp. 1917-1929 (2013), Oxford Journals.

Satoru Nogami et al., "HaematoCalMorph: *Haematococcus pluvialis* no TamenoTakino Saibo Gazo Shori Software", The bulletin of Japanese Society of Phycology, vol. 61, No. 1, p. 44, (2013).

International Search Report received for PCT Patent Application No. PCT/JP2013/081894 mailed on Mar. 4, 2014, 4 pages. (2 page of English Translation and 2 page of International Search Report).

Li F M et al., entitled "Cells Segmentation Using the Hybrid of Image Morphology and Edge Detector Algorithm and Cell Counting," Department of Electrical Engineering and Computer Science, Case Western Reserved University, Dec. 20, 2007, retrieved form the Internet: http://engr.case.edu/merat_francis/eecs490f07/StudentPapersF07/EECS490_Li.pdf, 7 pages.

Malpica N. et al., entitled "Applying Watershed Algorithms to the Segmentation of Clustered Nuclei," Cytometry, vol. 28, No. 4, Jan. 1, 1997, pp. 289-297.

Communication Supplementary European Search Report dated Jul. 18, 2016 in connection with European Patent Application No. 13857702.8, 8 pages.

\* cited by examiner

FIG. 3

1. NUMERICAL INFORMATION CONCERNING EACH CELLS

Name:                    NAME OF THE IMAGE FILE
ID:                      NUMBER OF THE REGION RECOGNIZED AS A CELL
Type:                    TYPE OF THE RECOGNIZED REGION (TARGET ALGAE, OTHER CONTAMINANT ORGANISMS,
                         AN INCOMPLETE REGION AT THE EDGE OF THE IMAGE, ETC.)
OuterArea:               AREA OF A CELL (PIXEL)
OuterOutlineLength:      LENGTH OF OUTLINE OF A CELL (PIXEL)
OuterCenterX:            X-COORDINATE OF THE GRAVITY CENTER (THE NUMBER OF PIXELS FROM THE LEFT)
OuterCenterY:            Y-COORDINATE OF THE GRAVITY CENTER (THE NUMBER OF PIXELS FROM THE TOP)
OuterMaxRadius:          MAXIMUM DISTANCE FROM THE GRAVITY CENTER TO THE EDGE (PIXEL)
OuterLongAxisLength:     LENGTH OF THE LONG AXIS (PIXEL)
OuterShortAxisLength:    LENGTH OF THE SHORT AXIS (PIXEL)
OuterAxisRatio (L/S):    LONG AXIS/SHORT AXIS
Round fitness:           FITNESS TO A CIRCLE ($4\pi \times$ AREA / SQUARED OUTLINE LENGTH).
Chordiogram distance:    CHORDIOGRAM DISTANCE*
OuterRedIntensity:       INTENSITY VALUE OF THE RED CHANNEL OF A CELL
OuterGreenIntensity:     INTENSITY VALUE OF THE GREEN CHANNEL OF A CELL
OuterBlueIntensity:      INTENSITY VALUE OF THE BLUE CHANNEL OF A CELL
InnerArea:               AREA OF THE PIGMENT PORTION IN A CELL (PIXEL)
InnerOutlineLength:      OUTLINE LENGTH OF THE PIGMENT PORTION IN A CELL (PIXEL)
InnerRedIntensity:       INTENSITY VALUE OF THE RED CHANNEL OF THE PIGMENT PORTION IN A CELL
InnerGreenIntensity:     INTENSITY VALUE OF THE GREEN CHANNEL OF THE PIGMENT PORTION IN A CELL
InnerBlueIntensity:      INTENSITY VALUE OF THE BLUE CHANNEL OF THE PIGMENT PORTION IN A CELL

* THE DIFFERENCE FROM THE HISTOGRAM OF THE MODEL IMAGE (CIRCLE HAVING A RADIUS OF 50 PIXELS)
TO THE HISTOGRAM OF EACH REGION. THE HISTOGRAM (CHORDIOGRAM) IS TAKEN FOR THE CORDS BETWEEN
ARBITRARY TWO POINTS ON THE OUTER PERIPHERY AND TAKEN FOR THE DISTANCE OF THE TWO POINTS AND
FOR THE ANGLE THE TWO POINT MAKES TO THE LINES PERPENDICULAR TO THE OUTER EDGE (DISSIMILARITY
FROM THE MODEL IMAGE, 0 TO 2)

FIG. 4

2. NUMERICAL INFORMATION CALCULATED FOR EACH FOLDER INCLUDING A PLURALITY OF IMAGE FILES

Name: FILE NAME

Touch: THE NUMBER OF CELLS TOUCHING THE EDGE OF AN IMAGE

Contaminant: THE NUMBER OF CONTAMINANT CELLS (CELLS OF WHICH THE SIMILARITY WITH THE MODEL IMAGE IS LESS THAN 0.5, AND WHICH DOES NOT HAVE A PIGMENT)

Algae: THE NUMBER OF TARGET ALGAE (CELLS OF WHICH THE SIMILARITY WITH THE MODEL IMAGE IS 0.5 OR GREATER, AND WHICH HAVE A PIGMENT)

Others: THE NUMBER OF THE OTHERS (UNDETERMINABLE CELLS OF WHICH THE SIMILARITY WITH THE MODEL IMAGE IS 0.5 OR GREATER)

Cell count: TOTAL NUMBER OF CELLS RECOGNIZED IN EACH FOLDER

Astaxanthin predictor: NUMERICAL VALUE USED FOR MEASURING THE ASTAXANTHIN AMOUNT (AVERAGE VALUE OF RED CHANNEL INTENSITY / AVERAGE VALUE OF BLUE CHANNEL INTENSITY)

Astaxanthin: ASTAXANTHIN AMOUNT CALCULATED USING PREDICTOR (137.9 × PREDICTOR − 174.3)

Chlorophyll predictor: NUMERICAL VALUE USED FOR MEASURING THE CHLOROPHYLL AMOUNT (AVERAGE VALUE OF GREEN CHANNEL INTENSITY / AVERAGE VALUE OF BLUE CHANNEL INTENSITY)

Chlorophyll: CHLOROPHYLL AMOUNT CALCULATED USING PREDICTOR (284.7 × PREDICTOR − 369.1)

(a) BRIGHT-FIELD IMAGE IS USED
(b) PIGMENTED REGION IMAGE
(c) CELL REGION IMAGE
(d) OUTERMOST EDGE PORTION OF EACH CELL

MERGE TWO IMAGES

FIG. 9
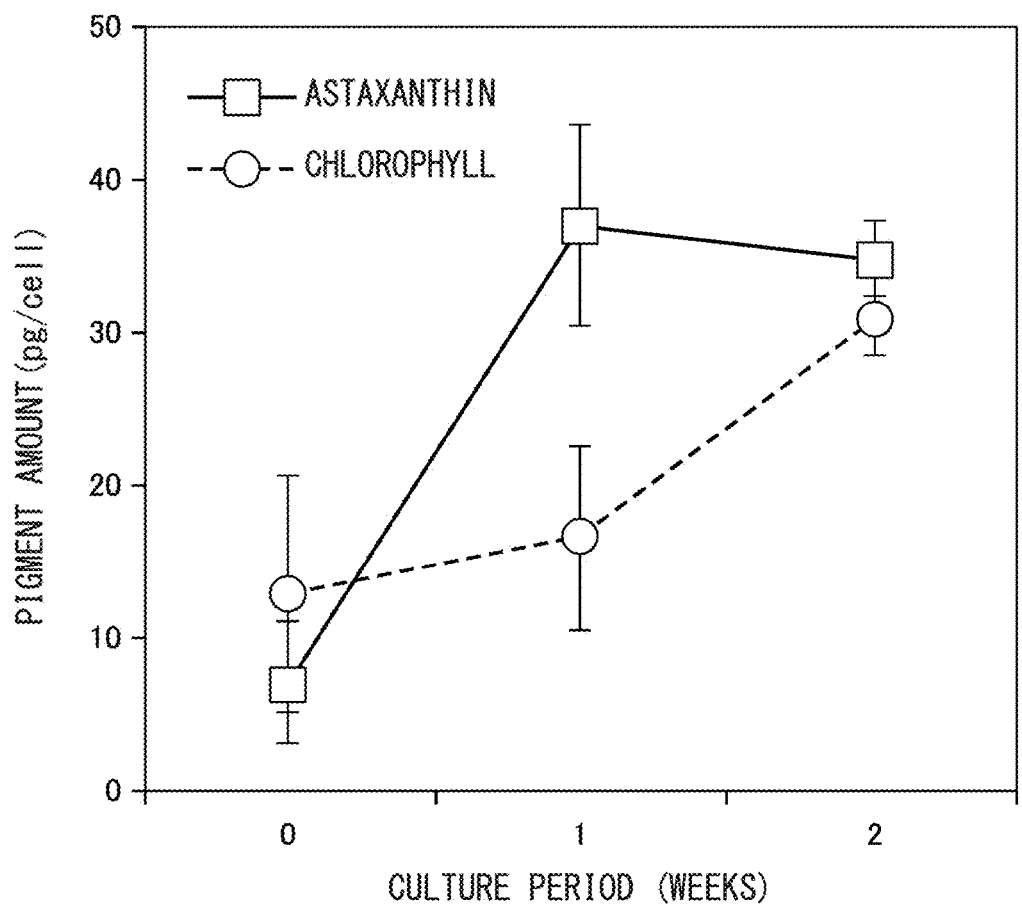
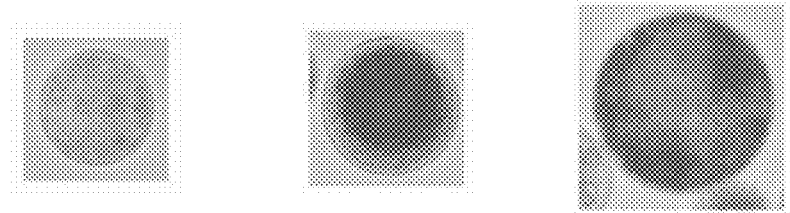

- CHLOROPHYLL CONCENTRATION (Pg/cell)
$Y_{chl} = -0.46 \times I_R + 0.56 \times I_G - 0.83 \times I_B - 72.01$

- CAROTENOID CONCENTRATION (Pg/cell)
$Y_{car} = 0.75 \times I_R - 0.22 \times I_G - 0.27 \times I_B - 61.83$

FIG. 51

| No | ID | kw | e6/wt | e8/wt | e6/e8 |
|---|---|---|---|---|---|
| 1 | OuterArea | 5.08E-08 | 1.457 | 1.130 | 1.289563 |
| 2 | OuterOutlineLength | 8.71E-08 | 1.223 | 1.083 | 1.129032 |
| 3 | OuterMaxRadius | 1.70E-07 | 1.193 | 1.097 | 1.087027 |
| 4 | OuterLongAxisLength | 1.01E-07 | 1.180 | 1.086 | 1.086540 |
| 5 | OuterShortAxisLength | 1.07E-07 | 1.226 | 1.023 | 1.198499 |
| 6 | OuterAxisRatio | 4.92E-01 | 0.872 | 1.043 | 0.832447 |
| 7 | OuterRoundFitness | 3.08E-01 | 1.020 | 0.989 | 1.031107 |
| 8 | OuterChordiogramDistance | 2.62E-02 | 0.841 | 0.992 | 0.848149 |
| 9 | InnerArea | 2.65E-08 | 1.562 | 0.937 | 1.666935 |
| 10 | InnerOutlineLength | 1.16E-06 | 1.262 | 0.992 | 1.272237 |
| 11 | AreaRatio | 2.54E-07 | 1.133 | 0.791 | 1.432700 |
| 12 | DistanceFromInnerCellCenterToInnerCenterOfMass | 5.06E-04 | 1.329 | 1.350 | 0.984769 |
| 13 | AngleFromInnerCenterOfMassToFarendOfLongAxis | 3.63E-01 | 1.068 | 1.054 | 1.013001 |
| 14 | OuterTotalRedIntensity | 1.01E-07 | 1.445 | 1.204 | 1.199808 |
| 15 | OuterTotalGreenIntensity | 1.07E-07 | 1.430 | 1.206 | 1.186122 |
| 16 | OuterTotalBlueIntensity | 5.39E-07 | 1.406 | 1.435 | 0.979507 |
| 17 | OuterMeanRedIntensity | 3.98E-06 | 1.011 | 1.039 | 0.972518 |
| 18 | OuterMeanGreenIntensity | 9.45E-10 | 0.984 | 1.039 | 0.950186 |
| 19 | OuterMeanBlueIntensity | 3.65E-06 | 0.947 | 1.119 | 0.845911 |
| 20 | InnerTotalRedIntensity | 3.22E-08 | 1.560 | 0.953 | 1.637704 |
| 21 | InnerTotalGreenIntensity | 7.11E-08 | 1.525 | 0.974 | 1.564987 |
| 22 | InnerTotalBlueIntensity | 6.29E-08 | 1.462 | 0.855 | 1.710387 |
| 23 | InnerMeanRedIntensity | 7.22E-06 | 1.004 | 1.034 | 0.971289 |
| 24 | InnerMeanGreenIntensity | 9.53E-08 | 0.989 | 1.034 | 0.950932 |
| 25 | InnerMeanBlueIntensity | 1.26E-01 | 0.952 | 1.087 | 0.876031 |

FIG. 53

| No | ID | LD1 | LD2 |
|---|---|---|---|
| 1 | OuterArea | -0.15363 | -0.65456 |
| 2 | OuterOutlineLength | -0.14185 | -0.66336 |
| 3 | OuterMaxRadius | -0.10451 | -0.6628 |
| 4 | OuterLongAxisLength | -0.1379 | -0.66294 |
| 5 | OuterShortAxisLength | -0.14749 | -0.66832 |
| 6 | InnerArea | -0.4001 | -0.4994 |
| 7 | InnerOutlineLength | -0.21255 | -0.42668 |
| 8 | AreaRatio | -0.46888 | 0.146919 |
| 9 | DistanceFromCellCenterToInnerCenterOfMass | -0.23593 | -0.51998 |
| 10 | OuterTotalRedIntensity | -0.09891 | -0.65988 |
| 11 | OuterTotalGreenIntensity | -0.08226 | -0.65972 |
| 12 | OuterTotalBlueIntensity | 0.018873 | -0.6006 |
| 13 | OuterMeanRedIntensity | 0.387047 | -0.25671 |
| 14 | OuterMeanGreenIntensity | 0.505544 | -0.25072 |
| 15 | OuterMeanBlueIntensity | 0.373876 | -0.1005 |
| 16 | InnerTotalRedIntensity | -0.3805 | -0.52855 |
| 17 | InnerTotalGreenIntensity | -0.35808 | -0.52804 |
| 18 | InnerTotalBlueIntensity | -0.42372 | -0.48206 |
| 19 | InnerMeanRedIntensity | 0.318035 | -0.30692 |
| 20 | InnerMeanGreenIntensity | 0.445407 | -0.30371 |

CELL MONITORING DEVICE, CELL MONITORING METHOD AND PROGRAM THEREOF

CROSS-REFERENCE TO RELATED APPLICATIONS

This application is a U.S. national phase of PCT Application No. PCT/JP2013/081894, filed Nov. 27, 2013, which claims priority to Japanese Application No. JP 2012-259880, filed Nov. 28, 2012, the contents of each of which are incorporated by reference herein.

TECHNICAL FIELD

The present invention relates to a cell monitoring device that monitors a state of cells using a microscopic image of the cells, a cell monitoring method, and a program thereof.

Priority is claimed on Japanese Patent Application No. 2012-259880, filed Nov. 28, 2012, the content of which is incorporated herein by reference.

BACKGROUND ART

In recent years, in determining cell status, experimental devices became available that are capable of monitoring live cells using a microscope for a long period of time. Using such experimental devices, real time monitoring can be performed on processes such as cell growth and cell division. Furthermore, by analyzing the time series of the cell image data obtained by imaging the process of such cell changes, a detailed analysis of the changes in the cells can be performed.

As an example, fermentation by unicellular yeast may be used to produce various liquors such as beer and distilled spirit. In order to maintain the quality of the liquors, the physiological state of yeast used in such fermentation is determined before the fermentation, to predict the effects on subsequent fermentation (for example, refer to Patent document 2). In fermentation, brewing, and substance production, or the like using yeast, it is necessary to figure out the physiological state of the yeast cells to be used in production in advance, in order to estimate the successfulness of the fermentation in advance, and to obtain a stable product with high quality.

Microalgae mainly refer to unicellular photosynthetic organisms. The microalgae convert light energy to chemical energy by photosynthesis, and use the converted energy for their survival and proliferation.

Some species of the microalgae biosynthesize useful components such as carbohydrates, essential unsaturated fatty acids (e.g., Docosa Hexaenoic Acid (DHA), Eicosa Pentaenoic Acid (EPA)), starch, or pigment. Industrial applications of these biosynthesis functions are expected.

For an efficient production of the aforementioned useful components using microalgae, it is important to appropriately monitor the physiological state of the microalgae cells. This is because the physiological state of the microalgae cells greatly varies depending on growth conditions from the surrounding environment, e.g., the culture medium composition, the carbon dioxide concentration, the light intensity, the culture temperature, and the cell density. Furthermore, in microalgae cells, the production amount and the accumulated amount of the useful components also change depending on the physiological state.

Therefore, for a highly efficient production of the useful components by the microalgae cells, it is essential to monitor the physiological state of the microalgae cells during cultivation, and the amount of production of the useful components, both in the optimization process of cell growth conditions, and in the production process of useful components by the cells.

In some cases, other organisms may contaminate in the culture medium in which cells are cultured and affect the physiological state of the microalgae cells. This influence from contaminant other organisms to the physiological state frequently causes a problem in the production process of the useful components by the cells.

Therefore, identification of such contaminant other organisms in the culture medium during cultivation is also important for a highly efficient production of the useful components using the microalgae cells.

An example of the microalgae cells is *Haematococcus pluvialis*, which is one of microalgae. This *Haematococcus pluvialis* has a high industrial utility since it biosynthesizes astaxanthin, which is a red antioxidant also provided as health food. *Haematococcus pluvialis* shows various cell morphologies reflecting the physiological state of the cells. In addition, the accumulated amount of astaxanthin also varies depending on the conditions during cultivation (for example, refer to Non-patent document 1).

In order to obtain efficient astaxanthin production by *Haematococcus pluvialis*, highly productive strains has been used, and the culture conditions has been optimized (for example, refer to Patent document 1). However, the present productivity is still not enough, and thus, further improvement in productivity is required. Furthermore, in recent years, a fungus *Paraphysoderma sedebokerensis* has been discovered as one of organisms which parasitize *Haematococcus pluvialis*. The cell color of *Haematococcus pluvialis* infected with *Paraphysoderma sedobokerensis* turns from green to dark brown, and eventually *Haematococcus pluvialis* dies (for example, refer to Non-patent document 2).

Different culture strains identified as *Haematococcus pluvialis* were obtained from all over the world, and contamination with organisms other than *Haematococcus pluvialis* was examined. As a result, surprisingly, contamination was observed in all culture strains including strains that are used industrially. Therefore, knowing the physiological state of the cells of *Haematococcus pluvialis*, the accumulated amount of astaxanthin which is a useful component, and the contamination ratio of other organisms is an important issue in industrial use.

As a method for detecting the physiological state of cells, for one microorganism, budding yeast, evaluating methods are known such as an viability measurement technique by a methylene blue method (for example, refer to Non-patent document 3).

However, in the method according to Non-patent document 3, the physiological state of cells cannot be determined from multiple aspects.

In addition, in Patent document 2, a method for evaluating the physiological state of yeast using a cell morphology quantitative value is described. Specifically, in this method, a fluorescent stained image of the outer portion, the nucleus, and the actin cytoskeleton in the yeast cell of interest is image-analyzed. Cell morphology quantitative analytic values are obtained for preset morphological parameters based on the morphological characteristics of the yeast cells, and by comparing these values with a database prepared in advance, the physiological state of the yeast of interest is evaluated.

However, in this method, a fixing and staining treatment of cells and observation by a fluorescence microscope are needed, and thus, it is not suitable for real time monitoring of physiological state in the field, production sites, or the like. In addition, no evaluation has been done or suggested on applications to the microalgae cells.

In addition, as a method for detecting the accumulated amount of useful components, Patent document 1 describes a method for quantifying the astaxanthin amount of *Haematococcus pluvialis* by detecting pigments from cells using dimethyl sulfoxide and by measuring the absorbance at 492 nm and 750 nm.

However, in the measurement, it is necessary to extract pigment from a large number of microalgae cell samples. This pigment extraction is time consuming.

In addition, regarding detection of other organisms, Non-patent document 4 describes a method for specifically staining chytrid, which is parasitic fungus found in the cells of microalgae diatom, with calcofluor white which binds to chitin. Chitin is a component of the chytrid cell wall.

In another previous study, zoosporangia of *Paraphysoderma sedebokerensis* which parasitize *Haematococcus pluvialis* are stained with FITC-WGA (Non-patent document 5).

However, in all of these, cell staining process is required, and the cells are not directly examined in the culture liquid. In addition, methods as in Patent document 2 or Non-patent document 5, require a fluorescence microscope, and thus are not suitable for examination in the field, production sites, or the like.

As described above, there have been no simple methods to real-time monitor growth status of the microalgae cells, the contamination status of contaminating other organisms in the culture medium of the microalgae cells (e.g., parasites), and the amount of useful substances produced by the microalgae cells.

RELATED TECHNICAL DOCUMENTS

Patent Documents

[Patent document 1] Japanese Unexamined Patent Application, First Publication No. 2007-97584
[Patent document 2] Japanese Unexamined Patent Application, First Publication No. 2011-30494

Non-Patent Documents

[Non-patent document 1] Journal of Phycology, Vol. 30 (1994), pp. 829-833
[Non-patent document 2] Mycological Research, Vol. 112 (2008), pp. 70-81
[Non-patent document 3] E. B. C. Analytica Microbiologica., J. Inst. Brew. Vol. 83 (1977), pp. 109-118
[Non-patent document 4] Applied and Environmental Microbiology, Vol. 75 (2009), pp. 2545-2553
[Non-patent document 5] Fungal Biology, Vol. 115 (2011), pp. 803-811

SUMMARY OF INVENTION

Technical Problem

The present invention has been accomplished in consideration of the above-described situation, and an object of the present invention is to provide a cell monitoring device, a cell monitoring method, and a program thereof, which real-time monitor the contamination status of other organisms in the cell culture medium, and also monitor the production amount of useful substances by the microalgae cells. The invention may be used for culture condition development or for breeding strains that produce large amount of useful substances, in order to improve the production of the useful substances by microalgae cells or the like.

Solution to Problem

One aspect of the invention is a cell monitoring device, including: an outline detecting section that detects edge pixels from a cell image in a captured image of cells arranged in a single layer (arranged on a plane in a single layer without overlapping) and generates an edge image including the detected edge pixels; a pigmented region detecting section that detects pixels of a pigmented region of the cell image in the captured image, and generates a pigmented region image including the detected pixels of the pigmented region; and an image merging section that, in a merged image obtained by overlaying the edge image and the pigmented region image together, detects a cell image region and a background image region in the captured image based on the variance of pixel intensity and thus detects the cell image region in the captured image.

The cell monitoring device according to the aspect may further include a cell morphology detecting section that classifies, among a plurality of the cell image region in the merged image, an image region in which the pigmented region is present as a target cell image, and classifies an image region in which the pigmented region is not present as a non-target cell image, and obtains a proportion of the non-target cell image in all of the cell images in the merged image.

The cell monitoring device according to the aspect may further include: a pigment value calculating section that calculates a pigment amount from an intensity value of the pigmented region in the cell image region.

The cell monitoring device according to the aspect may be constituted so that a mean intensity value of the pigmented region is determined from the cell image region, the pigment amount is measured by extracting pigment from the cell of which the captured image is captured, a regression equation between the mean intensity value and the pigment amount per cell is built in advance and saved in a storage section, the pigment value calculating section determines the mean intensity value in the cell image, and the pigment amount per cell is determined using the regression equation.

A cell monitoring method according to an aspect of the invention includes: an outline detecting process that detects edge pixels from a cell image in a captured image of cells arranged in single layer and generates an edge image including the detected edge pixels by an outline detecting section; a pigmented region detecting process that detects pixels of pigmented region of the cell image in the captured image and generates a pigmented region image including the detected pixels of the pigmented region by a pigmented region detecting section; and an image merging process that, in a merged image obtained by overlaying the edge image and the pigmented region image together, detects a cell image region and a background image region in the captured image based on the variance of pixel intensity and thus detects the cell image region in the captured image by an image merging section.

A program according to an aspect of the invention causes a computer to execute as a cell monitoring device for monitoring the shape of a cell, the program causes the computer to function as: an outline detecting section that detects edge pixels from a cell image in a captured image of cells arranged in a single layer and generates an edge image including the detected edge pixels; a pigmented region detecting section that detects pixels of a pigmented region of the cell image in the captured image, and generates a pigmented region image including the detected pixels of the pigmented region; and an image merging section that, in a merged image obtained by overlaying the edge image and the pigmented region image together, detects a cell image region and a background image region in the captured image based on the variance of pixel intensity and thus detects the cell image region in the captured image.

Advantageous Effects of Invention

According to the present invention, an edge image and a pigmented region image are extracted from the captured image, such as a microscopic image of microalgae, and the edge image and the pigmented region image are overlaid. Thus, it is possible to detect cell regions from the captured image with a higher precision as compared to the methods in the prior arts. It is also possible to easily detect the overall cell shape and the proportion of the pigmented region in the cell (for example, the region of the produced substance generated).

As a result, according to the present invention, indicators of the physiological cell states, the contamination status of other organisms, and the accumulation status of colored pigments are obtained as quantitative values. Thus, detection of the physiological state of the cells and the production status of useful components becomes easy.

BRIEF DESCRIPTION OF DRAWINGS

FIG. 3 shows the types of numerical information related to individual cells, saved and stored in a table storage section 23.

FIG. 4 shows the types of numerical information related to cells in the captured images, saved and stored in the table storage section 23.

FIG. 9 is a graph showing the changes in the accumulated amounts of the astaxanthin and chlorophyll measured by the cell monitoring device 1 after inoculating *Haematococcus* to a fresh culture medium, and representative cell images.

FIG. 51 is a table showing the significance test results for the parameters shown in FIGS. 21 to 45.

FIG. 53 is a table showing correlation coefficients between each of the classification functions LD1 and LD2 and the parameters shown in FIGS. 21 to 45.

DESCRIPTION OF EMBODIMENTS

Figure 1:
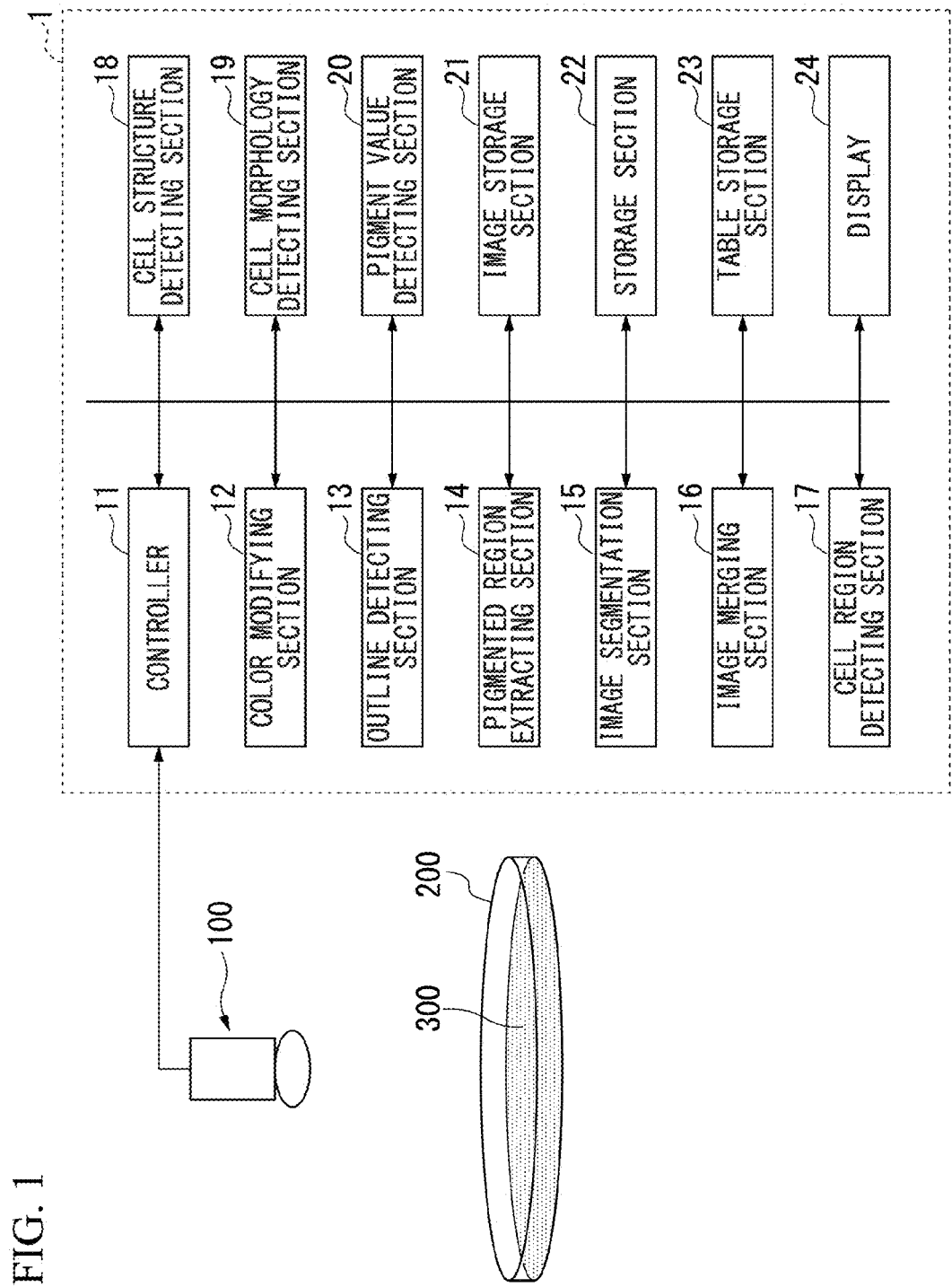
FIG. 1 is a schematic block diagram showing a configuration example of a cell monitoring device 1 according to an embodiment of the present invention.

Hereinafter, embodiments of the present invention will be described with reference to drawings. FIG. 1 is a schematic block diagram showing a configuration example of a cell monitoring device 1 according to an embodiment of the present invention. In the embodiment, images of unicellular organism cells are captured by a color camera attached to a microscope. This captured image is a color bright-field image constituted with pixels each including RGB (Red, Green, and Blue) components. In the embodiment, the captured image is used to analyze the physiological state of the growing cells, and also to analyze other contaminant organisms in the cell culture medium.

In FIG. 1, the cell monitoring device 1 of the embodiment is equipped with a controller 11, a color modifying section 12, an outline detecting section 13, a pigmented region detecting section 14, an image dividing section 15, an image merging section 16, a cell region detecting section 17, a cell structure detecting section 18, a cell morphology detecting section 19, a pigment value detecting section 20, an image storage section 21, a storage section 22, a table storage section 23, and a display 24. In the following embodiments, description will be made using cells of *Haematococcus pluvialis* (hereinafter, referred to as "*Haematococcus*"), which is unicellular microalgae, as an example of a monitoring target cell for physiological state monitoring.

In the embodiments, chytrid is used as an image of the contaminating other organisms, which are organisms other than the monitoring target cell. In *Haematococcus*, in the initial stage of its physiological state, chlorophyll (green pigment) is accumulated as a pigment body (plastid). As the cell development proceeds, the cell begins to accumulate another type of pigment body containing astaxanthin (red pigment), which is a useful substance.

An image capturing device 100, has a microscope provided with a CCD camera. The device captures images of *Haematococcus* cells at a predetermined magnification, as the cells are cultured in culture medium 300 in a culture vessel 200. The device then outputs the captured image to a cell monitoring device 1. In this process, the observer selects the imaging region where the image is captured in which the cells are arranged in a single layer and not in contact with other cells. The observer then captures images of *Haematococcus* cells in the culture medium 300 using the image capturing device 100.

Figure 2:
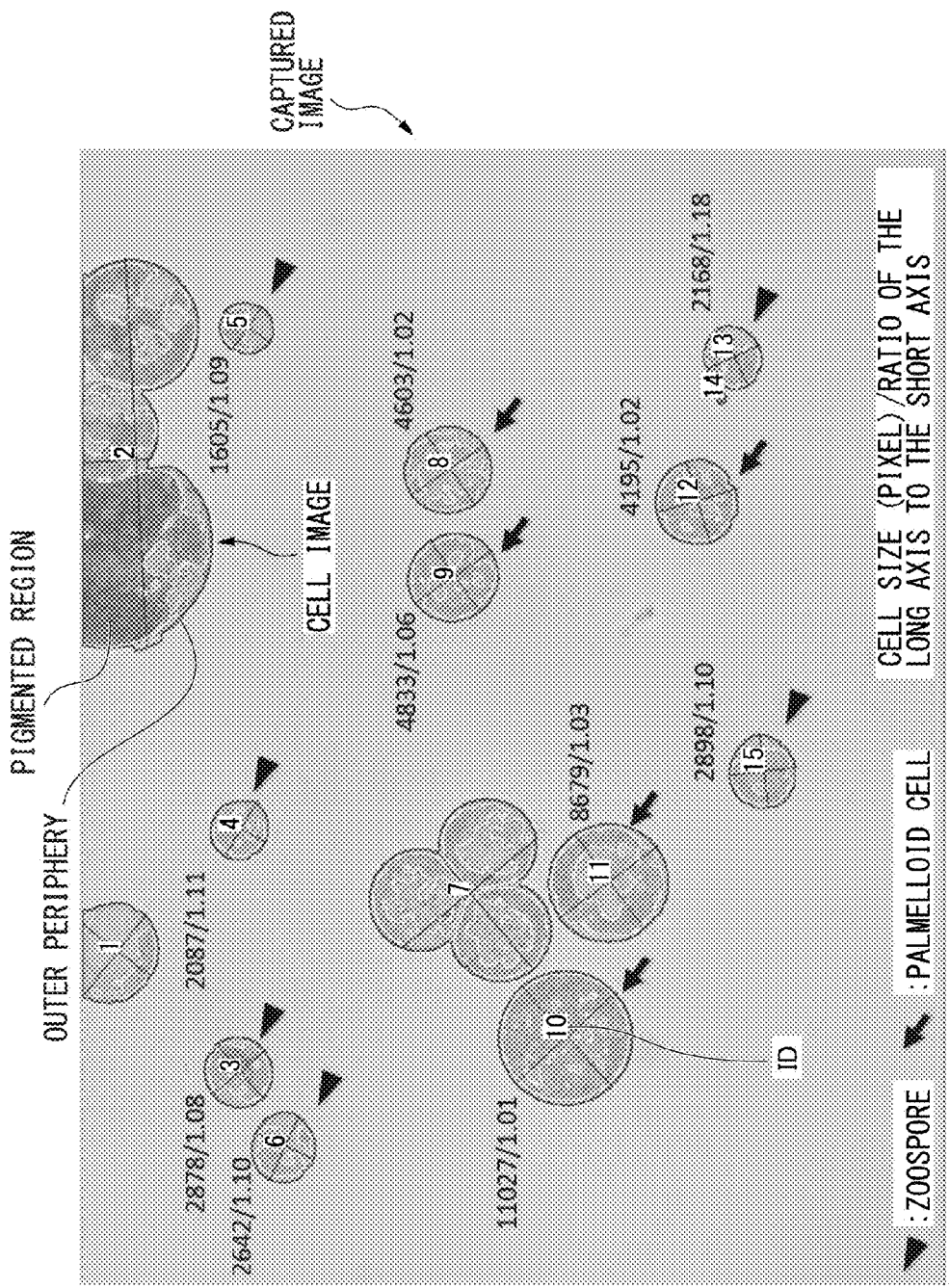
FIG. 2 shows an image obtained by overlaying an analysis result with a captured image (bright-field image) captured by an image capturing device 100.

FIG. 2 shows an image (bright-field image) captured by the image capturing device 100, and analysis results are overlaid thereon. A cell image has an outer edge and pigmented regions. The image in FIG. 2 is an image that may be displayed on the display 24. Likewise, the observer may use the display 24 to display any of the results from each section of the processing. The captured image goes through sections of the processing, and each processing section saves and stores the resulting image in the storage section 22.

In addition, as described below in detail, each of the cell images contains information of the cell area size in number of pixels, and the ratio of the long axis to the short axis (ratio L/S, i.e., OuterLongAxisLength to OuterShortAxisLength). This ratio is obtained by dividing the maximum width (OuterLongAxisLength) by the minimum width (OuterShortAxisLength) measured at the outermost edge of the cell image. FIG. 2 also shows identification numbers (ID) by which each cell image is identified, at the center of each cell image.

The figure also shows cell development morphology information, as either zoospore which is the initial stage state of *Haematococcus* development or as palmelloid cell. This information is classified by the observer based on the microscopic observation.

Returning to FIG. 1, the image capturing device 100 captures the images (bright-field image) of the cells in the culture medium 300 in the culture vessel 200. The controller 11 obtains those image data from the image capturing device 100 and save them in the image storage section 21 for storage.

The color modifying section 12 reads out the captured image from the image storage section, and adjusts RGB intensity values (gradient) for each pixel of the captured image. Based on the intensity variance within the captured image, the background is adjusted into gray.

The outline detecting section 13 carries out edge detection by Canny method on the image in the color-adjusted captured image, and generates an edge image. The Canny method is described in "Canny, J., A computational approach to edge detection, IEEE Trans. Pattern Analysis and Machine Intellgence, 8: 679-714, 1986".

The pigmented region detecting section 14 carries out binarization processing by Otsu method, which detects pixel regions having similar intensities in the read captured image (pigmented regions in the monitoring target cell described below). Otsu method is described in "Otsu N, A threshold selection method from gray-level histograms, IEEE Transaction on Systems, Man and Cybernetics, 9 (1): 62-66, 1979".

Then, the image segmentation section 15 overlays this pixel regions with the edge image detected by the outline detecting section 13. Edges overwrapping with the pixel regions are removed, to generate a new edge image. Then, the image segmentation section 15 carries out segmentation (region division) processing of the captured image using edge information of the edge image by a water-shed method, in order to detect regions of the cell image in the captured image, which corresponds to the objects to be detected. Water-shed method is described in "Beucher, S., Watershed of functions and picture segmentation, Acoustics, Speech, and Signal Processing, IEEE International Conference on ICASSP '82, 7: 1928-1931, 1982".

The image merging section 16, classifies each of the divided segments into either a cell segment in which the intensity variance is higher than the predetermined threshold value, or a background segment in which the intensity variance is lower than the predetermined threshold value. Thus, regions in the captured image corresponding to the cells are selected as cell segments.

In addition, the image merging section 16 merge the cell segments and the background segments to generate a cell image and a background image respectively, which are merged images.

The cell region detecting section 17, calculates the similarity of the cell image regions to a circular model image, using the chordiogram technique. A region having a similarity equal to or greater than a predetermined value is classified as a circular region, and a region having a similarity less than a predetermined value is classified otherwise. In addition, the cell region detecting section 17 merges the non-circular regions together. This calculation of the similarity with the circular model image using the chordiogram technique is described in "Toshev, A., Taskar, B., Daniilidis, K., Object detection via boundary structure segmentation, Computer Vision and Pattern Recognition, 950-957, 2010".

The cell structure detecting section 18 determines numerical information (described below) for each cell and for a plurality of cells, based on the cell outer shape of the cell image and the internal cell structures (pigmented region and non-pigmented region) of the cell images in the captured image. The determined numerical information is grouped for each cell image and for each captured image from which the cell images are detected, and written and stored in the table storage section 23.

The cell morphology detecting section 19 determines whether the cell is a monitoring target cell or not depending on the presence or absence of the pigmented region of the obtained cell constituting section. That is, the cell morphology detecting section 19 determines whether the cell shown in the cell image is *Haematococcus*, which is the monitoring target cell, or chytrid, a contaminant organism, based on the presence or absence of the pigmented region. In this determination, the cell morphology detecting section 19 classifies a cell image having a pigmented region to be *Haematococcus* which is the monitoring target cell, while a cell image without a pigmented region is determined to be chytrid which is not the monitoring target cell.

The cell morphology detecting section 19 also estimates the cell development stage from the outer shape of the cell (the ratio of the long diameter to the short diameter of the cell image, as described below).

The pigment value detecting section 20 calculates the mean intensity for each of RGB for the pixels in each of the cell image, and the accumulated amount of the pigment in the pigmented region is estimated from the mean value using a regression equation saved in advance in the storage section 22. In this embodiment, since cells of microalga *Haematococcus pluvialis* are the monitoring target, the astaxanthin content and the chlorophyll content are estimated.

<Numerical Information that Cell Structure Detecting Section 18 Outputs>

FIG. 3 shows the types of numerical information regarding each individual cell that are written and saved in the table storage section 23.

The type of data in this numerical information includes Name, ID, Type, OuterArea, OuterOutlineLength, OuterCenterX, OuterCenterY, OuterMaxRadius, OuterLongAxisLength, OuterShortAxisLength, OuterAxisRatio (L/S), Round fitness, Chordiogram distance, OuterRedIntensity, OuterGreenIntensity, OuterBlueIntensity, InnerArea, InnerOutlineLength, InnerRedIntensity, InnerGreenIntensity, and InnerBlueIntensity. Hereinafter, each numerical information in FIG. 3 will be described.

Name indicates the file name of the image data of the cell image. ID is an identification number that represents a cell image region that is recognized as a cell, and may include the position information (coordinate value) in the captured image. Type indicates the type of the cell shown in the cell image to which the ID is given. The type may include, in the example shown in FIG. 2: monitoring target cell (for example, the cell images with IDs 8 and 10 in FIG. 2), which are microalgae that is the monitoring target of interest; various contaminant organism images, which are organisms other than the monitoring target cells in the captured image; or incomplete shape cell image (for example, the cell image with IDs 1 and 2 in FIG. 2), that is a cell but has an incomplete shape spanning across the edge of the captured image.

OuterArea indicates the area of the cell image, in the unit of number of pixels. OuterOutlineLength indicates the length of the outer edge of the cell image, represented by the number of pixels arranged along the outer edge of the cell image. OuterCenterX is a numerical value indicating the x-coordinate of the gravity center of the cell image in the captured image using the xy coordinate system (in pixels, i.e., the number of pixels from the left end of the captured image). OuterCenterY is a numerical value indicating the y-coordinate of the gravity center of the cell image in the captured image using the xy coordinate system (in pixels, i.e., the number of pixels from the upper end of the captured image).

OuterMaxRadius is a numerical value indicating the maximum distance in pixels (maximum width) from the coordinate of the gravity center to the outer edge of the captured image. OuterLongAxisLength (L) is a numerical value indicating the size of the maximum width portion of the cell image, i.e., the length of the long axis in pixels. OuterShortAxisLength (S) is a numerical value indicating the size of the minimum width portion of the cell image, i.e., the length of the short axis in pixels. OuterAxisRatio (L/S) is a numerical value indicating the ratio L/S of OuterLongAxisLength to OuterShortAxisLength. Round fitness is a numerical value indicating the fitness of the cell image shape to a circle. The round fitness is calculated using the equation "$4\pi \times area/squared\ length\ of\ outline$".

Chordiogram distance, in this embodiment, is a numerical value indicating the similarity obtained from comparison results between a circular model image and an object image by Chordiogram, which determines the degree of similarity to the model image that is close to a circle. OuterRedIntensity is a numerical value indicating the mean intensity of the red channel (R pixels) in a cell. OuterGreenIntensity is a numerical value indicating the mean intensity of the green channel (G pixels) in a cell. OuterBlueIntensity is a numerical value indicating the mean intensity of the blue channel (B pixels) in a cell. InnerArea is a numerical value indicating the area size of a pigmented region by the number of pixels included in the region. InnerOutlineLength is a numerical value indicating the outer edge of a pigmented region by the number of pixels. InnerRedIntensity is the mean intensity of the red channel (R pixels) in a pigmented region. InnerGreenIntensity is the mean intensity of the green channel in a pigmented region. InnerBlueIntensity is the mean intensity of the blue channel in a pigmented region.

<Numerical Information Calculation of Cell Structure Detecting Section 18>

Hereinafter, calculation process of numerical information performed in the cell structure detecting section 18 will be described.

The cell structure detecting section 18 counts the number of pixels in the cell image, and this number of pixels is written in the table storage section 23 and saved as the cell area, i.e., OuterArea, one of the numerical information in FIG. 3. The cell structure detecting section 18 counts the number of pixels arranged along the outer edge of the cell image, and this number of pixels on the outer edge is written in the table storage section 23 and saved as the outline length of a cell, i.e., OuterOutlineLength in FIG. 3. The cell structure detecting section 18 determines the gravity center from the area of the cell image, determines the x coordinate and the y coordinate of the gravity center of the captured image, and the obtained x coordinate and y coordinate are written in the table storage section 23 and saved as OuterCenterX and OuterCenterY, respectively. The x coordinate is the number of pixels from the left end of the captured image, and the y coordinate is the number of pixels from the upper end of the captured image.

In addition, the cell structure detecting section 18 counts the pixel number of the maximum width from the coordinate of the gravity center (OuterCenterX, OuterCenterY) to the outer edge of the cell image, and this value is written in the table storage section 23 and saved as OuterMaxRadius in the numerical information in FIG. 3. The cell structure detecting section 18 counts the pixel number of the long axis length (long diameter) of the cell image, and this pixels number is written in the table storage section 23 and saved as OuterLongAxisLength (L) in the numerical information in FIG. 3. The cell structure detecting section 18 counts the pixel number of the short axis length (short diameter) of the cell image, and this pixels number is written in the table storage section 23 and saved as OuterShortAxisLength (S) in the numerical information in FIG. 3. The cell structure detecting section 18 divides OuterLongAxisLength by OuterShortAxisLength, and this division result is written in the table storage section 23 and saved as OuterAxisRatio (L/S) in the numerical information in FIG. 3.

The cell structure detecting section 18 also calculates "$(4\pi \times OuterArea)/(OuterOutlineLength)^2$", i.e., the goodness of fit to a circle, and this fitness is written in the table storage section 23 and saved as Round fitness in the numerical information in FIG. 3. The cell structure detecting section 18 calculates a Chordiogram for a circular model image and for the cell image, and calculate the distance between those Chordiograms. Chordiogram is a histogram of, for any chord between arbitral two points, the length, the angle, and the angles thereof to the outline normals at the two points. The distance, which represents the similarity to the model image, is written in the table storage section 23 and saved as Chordiogram distance in the numerical information in FIG. 3.

In addition, the cell structure detecting section 18 calculates the mean intensity values of the R pixels in the cell image, and this mean value is written in the table storage section 23 and saved as OuterRedIntensity in the numerical information in FIG. 3. In addition, the cell structure detecting section 18 calculates the mean intensity values of the G pixels in the cell image, and this mean value is written in the table storage section 23 and saved as OuterGreenIntensity in the numerical information in FIG. 3. In addition, the cell structure detecting section 18 calculates the mean intensity values of the B pixels in the cell image, and this mean value is written in the table storage section 23 and saved as OuterBlueIntensity in the numerical information in FIG. 3.

In addition, the cell structure detecting section 18 counts the area size of the pigmented region detected by the pigmented region detecting section 14 as the number of pixels included in the pigmented region, and this counted value is written in the table storage section 23 and saved as InnerArea in the numerical information in FIG. 3. The cell structure detecting section 18 counts, the number of pixels arranged along the outer edge of the pigmented region, and this number of pixels on the outer edge is written in the table storage section 23 and saved as the outline length of the pigmented region, i.e., InnerOutlineLength shown in FIG. 3. In addition, the cell structure detecting section 18 calculates the mean intensity value of the R pixels in the pigmented region, and this mean value is written in the table storage section 23 and saved as InnerRedIntensity in the numerical information in FIG. 3. In addition, the cell structure detecting section 18 calculates the mean intensity value of the G pixels in the pigmented region, and this mean value is written in the table storage section 23 and saved as InnerGreenIntensity in the numerical information in FIG. 3. In addition, the cell structure detecting section 18 calculates the mean intensity values of the B pixels in the pigmented region, and this mean value is written in the table storage section 23 and saved as InnerBlueIntensity in the numerical information in FIG. 3.

Next, FIG. 4 shows the types of numerical information related to cells in the captured images saved and stored in the table storage section 23.

This numerical information data includes Name, Touch, Contaminant, Algae, Others, Cell count, Astaxanthin predictor, Astaxanthin, Chlorophyll predictor, and Chlorophyll. Hereinafter, each numerical information in FIG. 4 will be described.

Name indicates the captured image file folder name constituted with image files of cell images. Touch is a numerical value indicating the number of cell images in contact with the edges of the captured image. Algae is a numerical value indicating the number of target cells (in this embodiment, unicellular microalgae) which are the monitoring targets in the captured image. The target cells of interest indicate cells having a similarity with the circular model image less than 0.5, and having a pigmented region. Contaminant is a numerical value indicating the number of non-target cells (in this embodiment, for example, unicellular chytrid) which are not monitoring targets in the captured image. The non-target, non-object cells indicate cells having a similarity with the circular model image less than 0.5, and not having a pigmented region. Others indicates a non-cell image in which neither the target cell nor the non-target cells are present. The non-cells indicate undeterminable cells of which the similarity with the model image is 0.5 or greater. The similarity used for determining whether the cell is the target cell, the non-target cell, or the non-cell is determined by the Chordiogram technique. Cell count indicates the total number of cells detected in the captured image, i.e., the sum of the number of cells in contact with the edge of the captured image, the number of target cells, and the number of non-target cells. In the embodiment, Cell count is a numerical value obtained by summation of the number of cells in contact with the edge of the captured image, the number of cells of microalgae, the number of cells of chytrid, and the number of non-cells.

Astaxanthin predictor is a numerical value used for measuring the astaxanthin amount; in this embodiment, this is a numerical value obtained by dividing the mean intensity values of the R pixels by the mean intensity values of the B pixels. The mean intensity values of the R pixels and the mean intensity values of the B pixels are mean values obtained by averaging the mean values in the target cells included in the captured image, and calculated for all of the target cells included in the captured image. The mean value in the target cell is the average of the intensity values of all pixels included in the target cell. Astaxanthin indicates the astaxanthin amount per pixel obtained from the regression curve (regression equation: 137.9×predictor−174.3, described below) using Astaxanthin predictor which is the mean intensity value of R pixels.

Chlorophyll predictor is a numerical value used for measuring the chlorophyll amount; in this embodiment, a numerical value obtained by dividing the mean intensity value of the G pixels by the mean intensity value of the B pixels. The mean intensity value of the G pixels and the mean intensity value of the B pixels are mean values obtained by averaging the mean values in the target cells included in the captured image in the entire target cells included in the captured image. The mean value in the target cell is an average of the intensity values of all pixels included in the target cell. Chlorophyll indicates the chlorophyll amount per pixel obtained from the regression curve (regression equation: 284.7×predictor−369.1, described below) using Chlorophyll predictor which is the mean intensity value of G pixels.

For Touch, Contaminant, Algae, and Others, the cell structure detecting section 18 reads out Type of the cell image in the table storage section 23, and counts the number of each type of cells, and the obtained count value is written in the table storage section 23 and saved as the numerical information in FIG. 4. In addition, for Cell count, the sum of the number of cells is obtained, and the obtained calculated value is written in the table storage section 23 and saved as the numerical information in FIG. 4.

Figure 5:
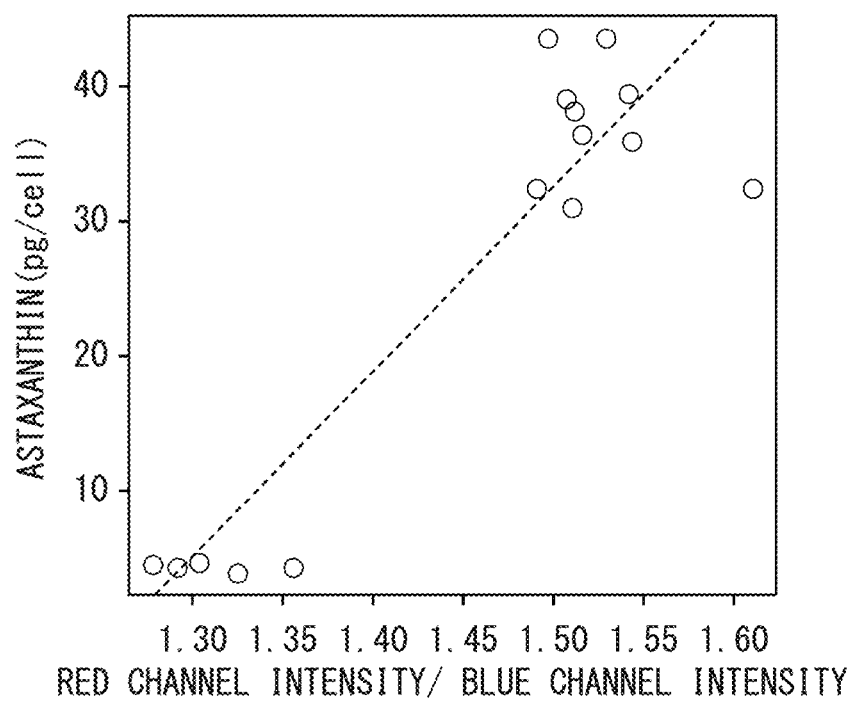
FIG. 5 is a graph showing a regression equation, showing the correlation between the pigment amount per cell for astaxanthin accumulated in the monitoring target cell (*Haematococcus*) and the intensity ratio, i.e., the ratio between the mean intensities for the R pixels and for the B pixels in the pixels of the cell image.

Next, FIG. 5 is a graph showing a regression equation which shows the correlation between the pigment amount per cell of astaxanthin accumulated in a monitoring target cell (*Haematococcus*) and the intensity ratio which is a ratio of the mean intensity value of R pixels to the mean intensity value of B pixels for the pixels in the cell image. In the graph of FIG. 5, the vertical axis indicates the accumulated amount (pg: picogram) of astaxanthin per cell, and the horizontal axis indicates the intensity value ratio obtained by dividing the mean intensity value of R pixels in the pixels in the cell image by the mean value of the B pixels.

The regression equation for astaxanthin calculation is build, for example, in the following manner in advance, and is written in the storage section 22 in advance and saved.

The above-described image analysis of the captured image is performed, numerical information in the above-described captured image is determined (except for the accumulated amount of the pigment), and the intensity ratio of the mean intensity value of R pixels to the mean intensity value of B pixels in the cell image is determined.

Furthermore, the pigment is extracted from the cells of which the image is captured in the following manner, and measurement of the pigment amount is performed. An aliquot of cell culture liquid (for example, 1 ml (milliliter)), which is the culture medium of the cells from which the image is captured, is sampled into a microcentrifuge tube, and centrifugation is performed at room temperature for 5 minutes at 8000 rpm to precipitate the cells at the bottom portion of the microcentrifuge tube. After the centrifugation, the supernatant is removed from the microcentrifuge tube, and 1 ml of 10% KOH (potassium hydroxide) solution is added to the precipitated cells, followed by heating at 70° C. for 5 minutes.

Next, the tube is centrifuged at room temperature for 5 minutes at 8000 rpm, to precipitate the cells at the bottom of the microcentrifuge tube and collected. After the centrifugation, the supernatant is removed from the microcentrifuge tube, the microcentrifuge tube containing the cell pellet is immersed into liquid nitrogen, and the cell pellet is pulverized for 30 seconds using a mixer. After the pulverization, 1 ml of dimethyl sulfoxide (DMSO) is added to the microcentrifuge tube, and the tube was vortexed for 15 minutes to extract the pigment, astaxanthin.

Thereafter, the tube is centrifuged at room temperature for 5 minutes at 8000 rpm, and the pigment, astaxanthin, is retrieved by transferring the supernatant (pigment extraction liquid) to a new microcentrifuge tube.

The light absorptions, absorbance, at 492 nm and 750 nm of the astaxanthin pigment extraction liquid are measured using a spectrophotometer. Using the measurement result of the absorbance, the pigment concentration of astaxanthin is determined by the following equation.

$$\text{Astaxanthin amount}(\mu g/ml) = 4.5(A_{492} - A_{750})$$

In this equation, 4.5 is the proportional coefficient, $A_{492}$ is the absorbance at 492 nm, and $A_{750}$ is the absorbance at 750 nm. By dividing the astaxanthin amount obtained therewith by the number of cells used in the extraction of astaxanthin, the astaxanthin amount per cell is calculated.

As described above, using the same sample from which captured images having different intensity ratios in different captured images are captured, the astaxanthin pigment concentration is determined.

Furthermore, the mean intensity values of R pixels and B pixels in the cell image is determined, and the ratio between those mean intensity values, i.e., the intensity ratio is determined. A regression equation between this intensity ratio and the extracted amount of astaxanthin, i.e., a regression equation to estimate the astaxanthin amount, is built by a regression analysis to determine the correlation of FIG. 5.

Figure 6:
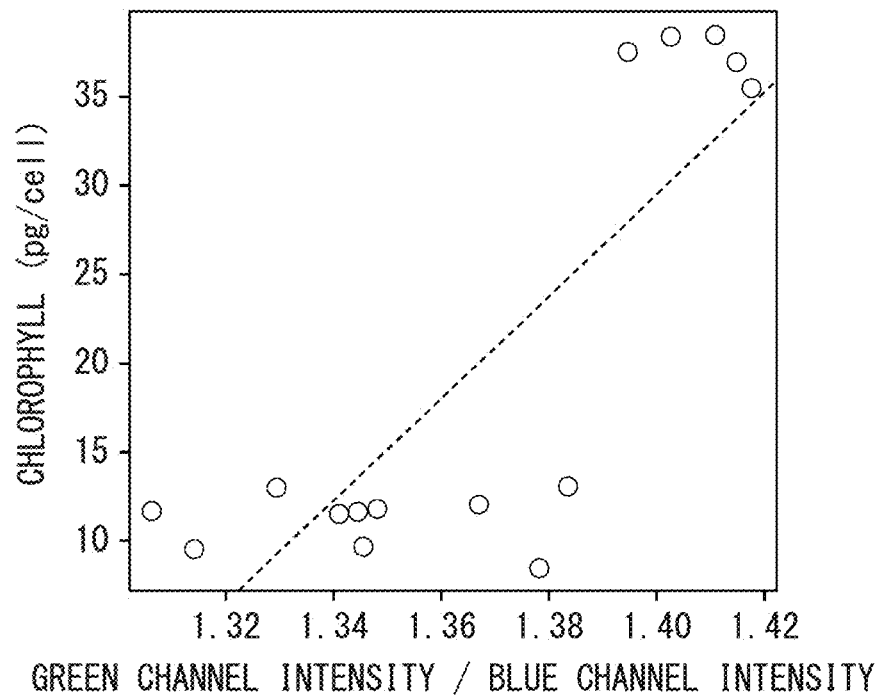
FIG. 6 is a graph showing a regression equation, illustrating the correlation between the pigment amount per cell for chlorophyll accumulated in the monitoring target cell (*Haematococcus*) and the intensity ratio, i.e., the ratio between the mean intensities for the G pixels and for the B pixels in the pixels of the cell image.

Next, FIG. 6 is a graph showing the regression equation which shows the correlation between the chlorophyll pigment amount per cell accumulated in the monitoring target cell (*Haematococcus*) and the intensity ratio which is a ratio of the mean intensity value of G pixels to the mean intensity value of B pixels in the pixels in the cell image. In the graph of FIG. 6, the vertical axis indicates the accumulated amount (pg: picogram) of chlorophyll per cell, and the horizontal axis indicates the intensity value ratio obtained by dividing the mean intensity values of G pixels in the pixels in the cell image by the mean value of the B pixels.

The regression equation for chlorophyll calculation is built, for example, in the following manner in advance, and is written in the storage section 22 in advance and saved.

The above-described image analysis of the captured image is performed, numerical information in the above-described captured image is determined (except for the accumulated amount of the pigment), and the intensity ratio of the mean intensity value of G pixels to the mean intensity value of B pixels in the cell image is determined.

Furthermore, the pigment is extracted from the cells of which the image is captured in the following manner, and measurement of the pigment amount is performed. An aliquot (for example, 1 ml (milliliter)), of the cell culture liquid, which is the culture medium of the cells of which the image is captured, is collected into a microcentrifuge tube, a centrifugation treatment is performed at room temperature for 5 minutes at 8000 rpm to precipitate the cells at the bottom portion of the microcentrifuge tube. After the centrifugation treatment, the supernatant is removed from the microcentrifuge tube, the microcentrifuge tube containing the cell pellet is immersed in liquid nitrogen, and a pulverization treatment is performed on the cell pellet for 30 seconds by a mixer. After the pulverization treatment, 1 ml of DMSO is added to the microcentrifuge tube, and the tube was vortexed for 15 minutes to extract the pigment, chlorophyll.

Thereafter, a centrifugation treatment is performed at room temperature for 5 minutes at 8000 rpm, and the pigment, chlorophyll, is retrieved by transferring the supernatant (pigment extraction liquid) to a new microcentrifuge tube. This chlorophyll extraction procedure, in which 1 ml of DMSO is added to the microcentrifuge tube, the tube is vortexed for 15 minutes and centrifuged, is repeated until the cell pellet becomes white.

Furthermore, the light absorptions, the absorbance, at 649 nm, 665 nm, and 750 nm of the chlorophyll pigment extraction liquid are measured by a spectrophotometer. Using the absorbance measurement result, the pigment concentration of chlorophyll is determined by the following equation.

$$\text{Chlorophyll amount}(\mu g/ml) = 14.85(A_{665} - A_{750}) - 5.14(A_{649} - A_{750})$$

In this equation, 14.85 and 5.14 are proportional coefficient, $A_{665}$ is the absorbance at 665 nm, $A_{649}$ is the absorbance at 649 nm, and $A_{750}$ is the absorbance at 750 nm. By dividing the chlorophyll amount obtained here by the number of cells used in the chlorophyll extraction, the chlorophyll amount per cell is calculated.

As described above, from the sample of which the captured images having different intensity ratios in different captured images are captured, the pigment concentration of chlorophyll is determined.

Furthermore, the mean intensity values of G pixels and B pixels in the cell image is determined, and a regression equation showing the correlation between the intensity ratio, i.e., the ratio of the mean values, and the chlorophyll extraction amount, i.e., a regression equation to estimate the chlorophyll amount is built by a regression analysis to determine the correlation of FIG. 6.

<Image Processing of Captured Image in Microscope>

In order to monitor the change of the cell morphology over time after inoculation to a fresh culture medium of *Haematococcus*, cell culture of *Haematococcus* is performed in the following manner. That is, the *Haematococcus* samples for microscope image capturing and for astaxanthin amount quantification for determining the regression equation is prepared in the following manner. The *Haematococcus* cell was cultured in the culture medium for three months under continuous light.

Furthermore, 10 ml culture liquid of *Haematococcus pluvialis* K0084 strains is inoculated to a culture medium of 90 ml in a flask having 300 ml capacity. Culture is performed by keeping the flask still under white light with a photon flux density of 45 µE (Einstein) $m^{-2}s^{-1}$ at the ambient temperature of 25° C.

Immediately after the start of the culture, on the 7th day, and on the 14th day, aliquots of 30 µl are collected from the flask, and microscopic observation and capturing of an image are performed.

The culture medium for the *Haematococcus* culture in this embodiment is a solution including: 4.055 mM $KNO_3$, 0.347 mM $CaCl_2$, 0.189 mM $Na_2CO_3$, 0.304 mM $MgSO_4$, 0.175 mM $K_2HPO_4$, 2.97 µM EDTA ($C_{10}H_{16}N_2O_8$), 31.2 µM citric acid, 1.68 µM $Co(NO_3)_2$, 38.17 µM Fe(III)$NH_3$ citrate, 4.7 µM $H_3BO_3$, 0.91 µM $MnCl_2$, 0.07 µM $ZnSO_4$, 0.17 µM $Na_2MoO_4$, and 0.03 µM $CuSO_4$.

In addition, the microscopic observation of *Haematococcus* in the culture medium is performed in the following manner.

A square frame having each side of 1 cm is formed with nail enamel on the surface of a glass slide having a thickness of 1 mm, and 30 µl of a culture liquid of *Haematococcus* is dropped in the frame. The frame of the nail enamel is covered with a cover glass having a thickness of 0.17 mm, and sealed with the nail enamel, whereby a preparation is prepared. In addition, the microscopic observation is performed using a upright microscope equipped with a 40× magnification objective lens. For capturing microscopic images, a color Charge Coupled Device (CCD) camera is used at a resolution of 2040×1536 pixels (approximately 3 million pixels). Furthermore, the captured image is saved in the image storage section 21 through the controller 11 as Joint Photographic Experts Group (JPEG) images in RGB format (R pixels, G pixels and B pixels).

<Description of Operation of Cell Monitoring Device>

Figure 7:
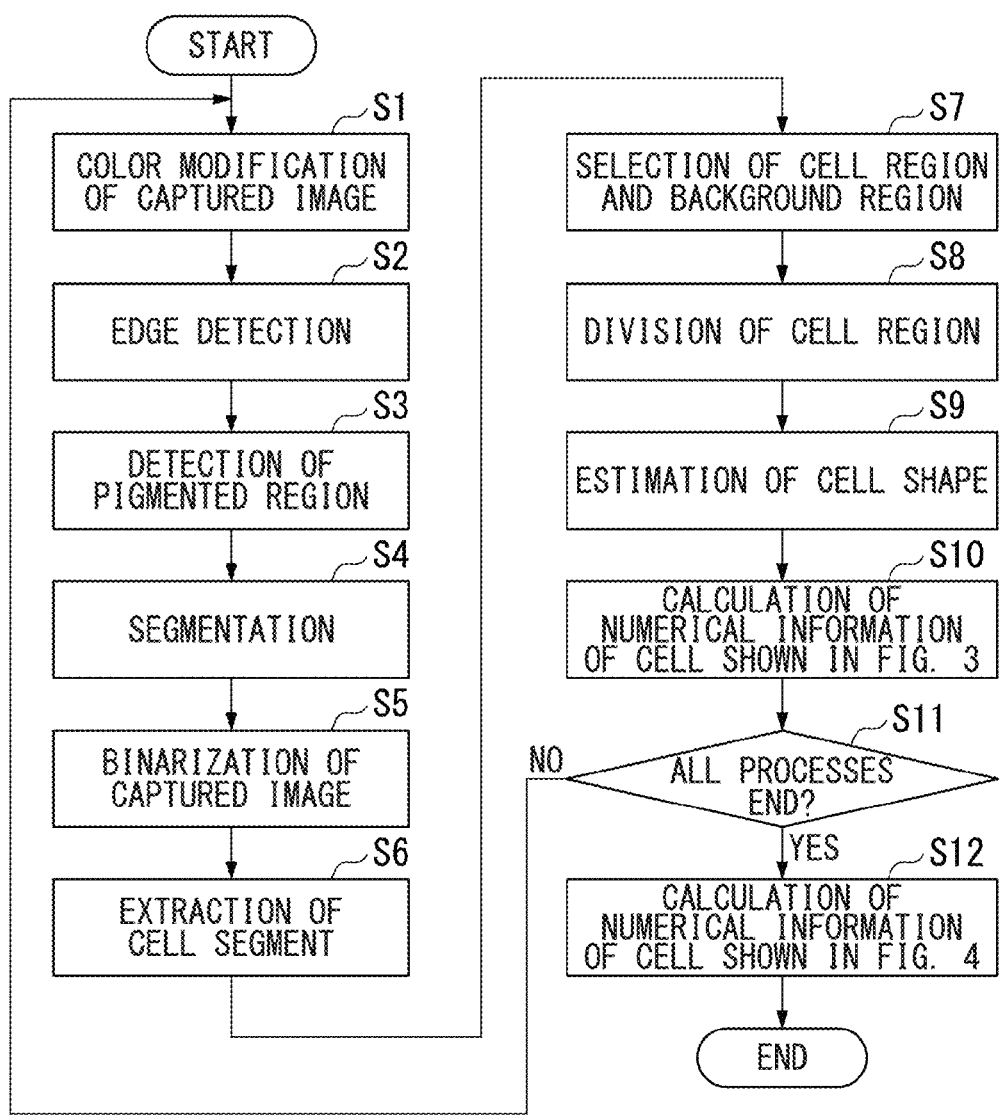
FIG. 7 is a flow chart showing an operation example of a cell monitoring process in a cell observation device 1 according to the embodiment.
Figure 8:
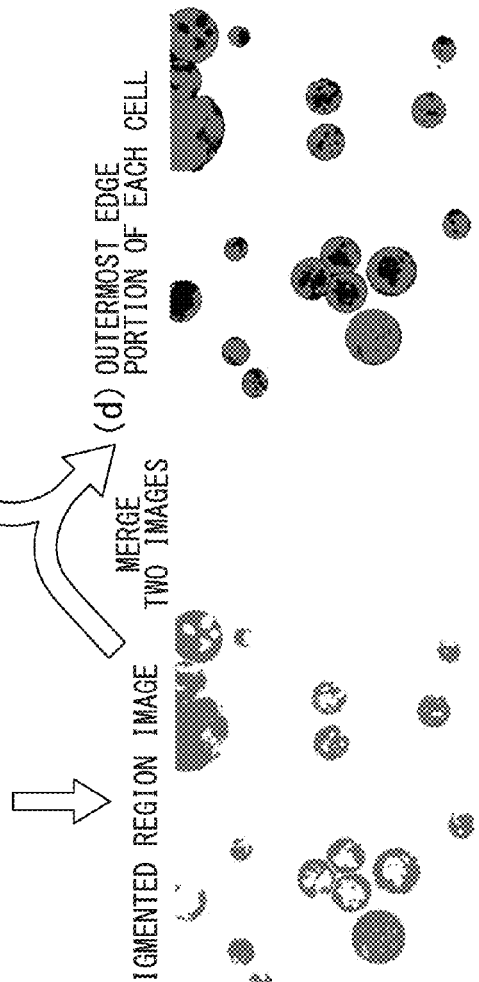
FIG. 8 shows the outermost edge portion of the cell image obtained by overlaying an edge image and a pigmented region image.

Next, the operation for monitoring cells of the cell monitoring device 1 according to the embodiment is described using FIGS. 7 and 8. FIG. 7 is a flow chart showing an operational example of the cell monitoring process in the cell monitoring device 1 according to the embodiment. FIG. 8 is a diagram showing the outermost edge portion of the cell image obtained by overlaying an edge image and a pigmented region image. FIG. 8(a) shows a captured image which is a bright-field image captured by the image capturing device 100. In the embodiment, a pretreatment such as a fluorescent staining is not performed at all on cells. FIG. 8(b) shows a pigmented region image generated by the pigmented region detecting section 14.

FIG. 8(c) shows a cell region image detected by the outline detecting section 17. FIG. 8(d) is an image obtained by overlaying the pigmented region image and the cell region image, and shows the outermost edge portion of the cell image.

As described above, before the following image analysis process is performed, the observer prepares a preparation of the culture medium, and captures images of *Haematococcus* cells in the preparation by a CCD camera. When capturing the image, the observer searches a region of a viewing field where *Haematococcus* cells are not overlapping in the vertical direction and are not in contact with other cells. That is, the observer searches a region where *Haematococcus* cells are arranged in a single layer without contacting with other cells in the preparation plane.

In addition, capturing of *Haematococcus* is performed avoiding regions which clearly appears to include abnormal cells or contaminating objects, or regions where there is dirt on the slide glass and a wall-glass causing color unevenness in the background around the cell. In addition, different viewing fields are selected, and images are captured while moving the stage of the microscope in a certain direction so as not to capture the same cell multiple times (0.5 seconds/image). For example, a number of image layers are captured that is enough to obtain the information of 200 cells.

Step S1:

The observer performs a color modifying process of the cell image in the captured image saved in the image storage section 21 on the cell monitoring device 1 by inputting a control signal from an input device (for example, a keyboard) which is not shown.

When the control signal of analysis process is supplied from the input device, the controller 11 reads the data (FIG. 8(a)) of the captured image from the image storage section 21, and supplies the read captured image to the color modifying section 12.

The color modifying section 12 aggregates histograms each of the intensity values of R pixels, G pixels, and B pixels of the captured image, and selects the intensity of the most frequent value as the intensity value of the background.

Thus, the color modifying section 12 adjusts the intensity values of respective R pixels, G pixels, and B pixels of the captured image such that the background region other than the cell image becomes gray.

Furthermore, the controller 11 supplies the captured image, in which R pixels, G pixels, and B pixels are adjusted, to the image display 24 and to the outline detecting section 13, and stores it in the image storage section 21. The image processing from the following Step S2 is performed using the captured image after the background region is adjusted to be gray.

Step S2:

The outline detecting section 13 extracts (picks up) the data of R pixel from the RGB data of each pixel that constitutes one pixel of the captured image.

Furthermore, the outline detecting section 13 adjusts the intensity value of the data of the extracted R pixel such that the minimum value and the maximum value of the intensity become 0 and 255, respectively.

Furthermore, using the adjusted R pixel data, the outline detecting section 13 performs edge (outline) pixel detection of image shapes in the captured image by the Canny method. Here, the reason R pixel is used is, for example, that since the cell membrane of microalga *Haematococcus* is red, it is convenient to detect the cell image edges in the captured image.

In addition, the outline detecting section 13 outputs the detected edge image to the image segmentation section 15.

Step S3:

After the edge detection in the outline detecting section 13 is completed, the controller 11 supplies the same captured image, which was supplied to the outline detecting section 13, to the pigmented region detecting section 14.

The pigmented region detecting section 14 extracts the B pixel data from the RGB data of each pixel constituting one pixel of the captured image.

Furthermore, the pigmented region detecting section 14 binarizes the intensity value of each B pixel in the captured image by the Otsu method, and detects the pixels in pigmented region (plastid) which is regions containing pigment (pigments of astaxanthin or chlorophyll) within a cell. In addition, the pigmented region detecting section 14 outputs the pigmented region which became black by the binarization to the image segmentation section 15 as a pigmented region image (FIG. 8(*b*)).

Step S4:

The image segmentation section 15 overlays the edge image supplied from the outline detecting section 13 and the pigmented region image supplied from the pigmented region detecting section 14, removes extra edge portions in the edge image, and performs completion of incomplete cell shapes in the edge image, whereby a new edge image is generated.

Next, the image segmentation section 15 performs a segmentation (region division) of the captured image by the water-shed method using the information of the detected edge image in order to detect regions of the cell image in the captured image which corresponds to an object to be selected.

In addition, the image segmentation section 15 thins the boundary lines of the segmented regions, i.e., generates a boundary line (boundary lines having the width of one pixel) of the segment in the captured image.

Step S5:

The image merging section 16 performs binarization of the intensity values of the RGB pixels constituting one pixel in the captured image, i.e., R pixels, G pixels, and B pixels, by the above-described Otsu method.

Furthermore, the image merging section 16 detects pixel aggregation regions which is a region of a pixel in which at least one binarized intensity value of RGB pixels constituting one pixel equals to a threshold value or less. In practical, the pixel aggregation region is included in the region of the cell image in the captured image.

Step S6:

The image merging section 16 overlays the segment boundary line onto the pixel aggregation region image in the captured image, and calculates the proportion of the above-described pixel aggregation region for each segment. Furthermore, the image merging section 16 classifies segments in which the proportion of the pixel aggregation region is greater than the proportion determined in advance, as cell segments, which is the regions of the cell image in the captured image. At this stage, there is a possibility that background regions which is not actually cell regions are still included.

Step S7:

Thus, for each of the classified cells segments, the image merging section 16 calculates the mean value and the variance of the pixel values for the cell segment, for each of R pixels, G pixels, and B pixels.

Furthermore, the image merging section 16 classifies a cell segment having a large intensity variance for at least any one of R pixel, G pixel, and B pixel as a cell segment that is corresponding to the region where the cell image is captured in the captured image.

In addition, the image merging section 16 determines that segments other than the segments classified as cell segments are background segments.

After the segment classification process is completed, the image merging section 16 merges the cell segments and the background segments, generates a cell image and a background image, that are merged images.

The classification process of the above-described cell segments and background segments is performed using the fact that the variance of the intensity values in cell segments is greater as compared to the background segment.

Step S8:

Next, in order to select the image regions that is classified as cell image regions in the merged image, the cell region detecting section 17 divides the image regions classified as the cell image from the merged image as segment regions using the above-described water-shed method.

Step S9:

Furthermore, the cell region detecting section 17 classifies the segments among each of the divided segments that are in contact with the edge of the captured image as Touch. Furthermore, the cell region detecting section 17 classifies, using the chordiogram, the rest of the segments into either as circular segments that are similar to the circular model images, and non-circular segments that are different from the circular model image. The circular segments similar to the circle is recognized as microalgae cells, i.e., *Haematococcus*.

In addition, the cell region detecting section 17 integrates the non-circular segments other than the circular segments, and outputs them to the cell structure detecting section as final cell region images (FIG. 8(*d*)).

Step S10:

The cell structure detecting section 18 calculates the numerical information shown in FIG. 3 in the cell images in the captured image described above, and writes the numerical information obtained for each of cell images in the table storage section 23 and saves them.

In addition, at this stage, the cell morphology detecting section 19 performs extraction (picking-up) of the intensity values of R pixels and G pixels in the regions classified as pigmented region by the pigmented region detecting section 14, in the cell image. Furthermore, then the intensity values of both R pixels and G pixels are less than a threshold value determined in advance, the cell morphology detecting section 19 classifies the cell as chytrid, and writes "other contaminant organism" in Type section of the numerical information in FIG. 3 for this cell.

Step S11:

The controller 11 determines whether the image analysis process is completed or not, for all of the captured images in the image storage section 21.

At this stage, if the image analysis process of all of the captured images in the image storage section 21 is completed, the controller 11 proceeds the process to Step S12.

On the other hand, if the image analysis process has not completed for all of the captured images in the image storage section 21, the controller 11 returns the process to Step S1, reads a new captured image from the image storage section 21, and continues the image analysis process.

Step S12:

The cell structure detecting section 18 reads the numerical information from the numerical table shown in FIG. 3 stored in the table storage section 23, and calculates the numerical information Contaminant, Algae, Other, and Cell count shown in FIG. 4, and writes in each folder of monitoring target cells and saves them. In this folder, for example, the numerical information obtained at a particular date and time from the cell images in the captured images used for calculation of the astaxanthin or chlorophyll pigment amount is saved.

As described above, according to the embodiment, edge images and pigmented region images detected from the captured image which is a microscopic photograph of microalga cells or the like are overlaid together. Thus, the incomplete outer shape of the cell image region is completed using the pigmented region image. Therefore, it is possible to detect the outer shape of the cell image in the captured image with higher precision compared to the method in the related art, and it is also possible to readily detect the overall shape of the cell and the proportion of the pigmented regions in the cell (for example, the region of the produced substance generated).

<Estimation Process of Pigment Amount Accumulated in Cell>

After the image analysis process of the captured image is completed, the controller 11 cause the pigment value detecting section 20 to perform a pigment amount detection process.

The pigment value calculating section 20 reads OuterRedIntensity (mean intensity value of R pixels in the cell image) and OuterBlueIntensity (mean intensity value of B pixels in the cell image) from the numerical information of all of the target algae cell images in the folder in the table storage section 23.

Next, the pigment value calculating section 20 determines the OuterRedIntensity summation value by summation of OuterRedIntensity of all cell images, and in the same manner, determines an OuterBlueIntensity summation value by summation of OuterBlueIntensity of all cell images.

Furthermore, the pigment value calculating section 20 divides the OuterRedIntensity summation value by the OuterBlueIntensity summation value, and calculates Astaxanthin predictor which is the intensity ratio of R pixel and B pixel. The pigment value calculating section 20 writes the calculated Astaxanthin predictor as the numerical information in FIG. 4 of the table storage section 23 and saves it.

Next, the pigment value calculating section 20 reads the regression equation for astaxanthin calculation from the storage section 22, determines the accumulated amount of astaxanthin per cell by substituting the obtained Astaxanthin predictor into the regression equation, and writes the accumulated amount as Astaxanthin in the numerical information in FIG. 4 of the table storage section 23 and saves it.

Next, the pigment value calculating section 20 reads OuterGreenIntensity (the mean intensity value of G pixels in the cell image) and OuterBlueIntensity (the mean intensity value of B pixels in the cell image) from the numerical information of all cell images of target algae in the folder from the table storage section 23.

Next, the pigment value calculating section 20 determines the OuterGreenIntensity summation value by summation of OuterGreenIntensity of all cell images, and in the same manner, determines an OuterBlueIntensity summation value by summation of OuterBlueIntensity of all cell images.

Furthermore, the pigment value calculating section 20 divides the OuterGreenIntensity summation value by the OuterBlueIntensity summation value, and calculates Chlorophyll predictor which is the intensity ratio of R pixel and B pixel. The pigment calculation section 19 writes the calculated Chlorophyll predictor as the numerical information in FIG. 4 in the table storage section 23 and saves it.

Next, the pigment value calculating section 20 reads the regression equation for chlorophyll calculation from the storage section 22, determines the accumulated amount of astaxanthin per cell by substituting the obtained Chlorophyll predictor into the regression equation, and writes the accumulated amount as Chlorophyll in the numerical information in FIG. 4 of the table storage section 23 and saves it.

FIG. 9 is a graph showing the changes in the accumulated amounts of the astaxanthin and chlorophyll measured by the cell monitoring device 1 after inoculating *Haematococcus* to a fresh culture medium. In FIG. 9, the vertical axis indicates the pigment amount (accumulated amount) per cell, and the horizontal axis indicates the culture period (weeks).

In the same manner as in FIG. 9, after inoculating *Haematococcus* to a culture medium, from immediately after the inoculation (0 week), to one week after the inoculation, and to two weeks after the inoculation, the accumulated amounts of astaxanthin and chlorophyll increases.

This result coincides with the knowledge that, in actual *Haematococcus* cells, the accumulated amount of astaxanthin reaches a plateau after one week, and the accumulated amount of chlorophyll increases by the lapse of time. Therefore, using the cell monitoring device 1 according to the embodiment, it is possible to accurately estimate the accumulated amount of the pigment while the cells are being cultured without actually destroying the cells for the measurement of the accumulated pigment amount.

<Estimation Process of Development of *Haematococcus*>

Figure 10:
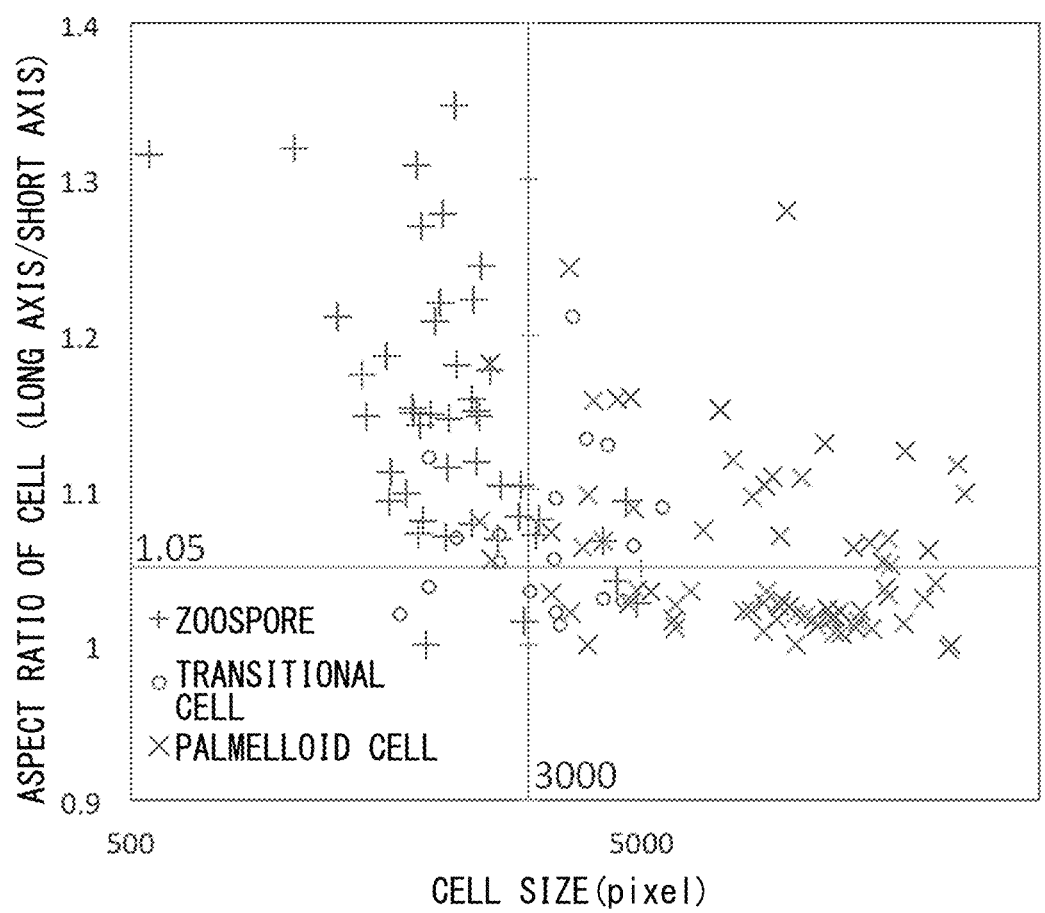
FIG. 10 shows correlation between the numerical information (OuterArea, OuterAxisRatio (L/S)) of the cell image, which are obtained from the image analysis using the cell monitoring device 1, and cell classification by manual inspection (zoospore cell, transitional cell, and palmelloid cell).

FIG. 10 is a diagram showing the correlation between the numerical information (OuterAxisRatio (L/S), OuterArea) of the cell image obtained from the image analysis by the cell monitoring device 1 and classification of the cells by manual inspection. In FIG. 10, the vertical axis indicates the ratio of the long diameter to the short diameter of the cell image, i.e., OuterAxisRatio (L/S), and the horizontal axis indicates the area of the cell image, i.e., OuterArea.

In addition, the "+" mark indicates a cell classified as a zoospore by manual inspection, the "○" mark indicates a cell classified as a transitional cell that is in the middle of a transition from a zoospore to a palmelloid cell by manual inspection, and the "X" mark indicates a cell which is classified as a palmelloid cell (*Haematococcus* cell that produces astaxanthin as pigment) by manual inspection.

When inoculated to a fresh culture medium, *Haematococcus* cell forms an endospore, and when the spore sprouts, the spore become a motile zoospore which has flagellum.

Furthermore, after a while, the zoospore loses the flagellum, and becomes a palmelloid cell which has lost the motility. FIG. 10 is a diagram for finding the conditions for performing the classification between zoospore and palmelloid cell having a different physiological states.

Using *Haematococcus* cells transferred to a fresh culture medium, *Haematococcus* cells in twenty captured images are classified into three types, zoospores, palmelloid cells, and unclassifiable cells in the transitional state, by manual inspection.

Furthermore, the captured images are analyzed by the cell monitoring device 1 of the embodiment, and using in total of 138 quantitative values concerning the cells classified as *Haematococcus*, discrimination between a zoospore and a palmelloid cell is performed. In the graph showing the size (area) of a cell and the ratio of the long axis to the short axis of a cell, as described above, a zoospore is represented by "+", a palmelloid cell is represented by "x", and a cell in a transition state is represented by "○". In the graph of FIG. 10, it is confirmed that 87% of the zoospores is included in the region where the cell area is less than 3000 pixels, and 96% of the palmelloid cells is included in the region where the cell area is 3000 pixels or greater.

Therefore, when the cell area is 3000 pixels or greater, the cell can be classified as a palmelloid cell, and when the cell area is less than 3000 pixels, the cell can be classification as a zoospore. In addition, since the ratio of the long axis to the short axis is also characteristic, it is possible to distinguish a zoospore from a palmelloid cell by classifying a cell image having OuterAxisRatio (L/S)>1.05 and having the area of the cell image, i.e., OuterArea less than 3000 pixels as a zoospore, and, on the other hand, by classifying a cell image having OuterAxisRatio (L/S)≤1.05 and having the area of the cell image, i.e., OuterArea 3000 pixels or greater as a palmelloid cell. The determination is performed by the cell morphology detecting section 19.

In addition, in the same manner as in FIG. 2, it has been known to the observers, a cell having the cell area less than 3000 pixels and the ratio (L/S) of the long axis to the short axis 1.05 or greater is a zoospore, and, on the other hand, a cell having the cell area 3000 pixels or greater and the ratio (L/S) of the long axis to the short axis less than 1.05 is a palmelloid cell. From this result, it is found that the classification of the cell monitoring device 1 according to the embodiment is the same as that from the knowledge of the observers.

In addition, in the embodiment, although *Haematococcus* used as the example of a monitoring target cell, the embodiment is not limited to this *Haematococcus*, and as long as the cell is unicellular, the embodiment is applicable to any cell as the monitoring target. For example, it is possible to quantify specific morphologies of other microalgae cells such as *chlorella, nannochloropsis, dunaliella*, and *botryococcus* as well as *Haematococcus*.

<Estimation of Pigment Amount in *Haematococcus* Cell by Multiple Regression Analysis>

Next, a method for estimating each of astaxanthin (carotenoid) amount and the chlorophyll amount using the intensity values of red channel (R pixel), green channel (G pixel), and blue channel (B pixel) in the pixels in the cell image will be described. Astaxanthin is one of carotenoids.

As described above, in FIG. 5, a method for estimating the astaxanthin amount by a regression equation using the mean intensity values of R pixels and B pixels in the cell image is described. In addition, in FIG. 6, a method for estimating the chlorophyll amount by a regression equation using respective intensity values of G pixels and B pixels in the cell image is described.

However, in the embodiment, as described above, the mean intensity value of G pixels in the cell image is added to the mean intensity values of R pixels and B pixels in the cell image, and the astaxanthin amount and the chlorophyll amount are determined using a multiple regression equation for determining the amount of pigment produced by cells from the mean intensity values of each of R pixels, G pixels, and B pixels in the cell image. The multiple regression equation for determining the astaxanthin amount and the multiple regression equation for determining chlorophyll amount are different from each other (described below), and are written in the storage section 22 in advance and saved.

In addition, the estimation of the pigment amount using the multiple regression equation is performed by the pigment value calculating section 20 described above. The pigment value calculating section 20 reads the regression equation for astaxanthin calculation from the storage section 22, determines the accumulated amount of astaxanthin or chlorophyll per cell (astaxanthin amount, chlorophyll amount) by substituting the mean intensity values of each of R pixels, G pixels, and B pixels in the cell image into each of the multiple regression equations of astaxanthin and chlorophyll, and writes the accumulated amount as Astaxanthin or Chlorophyll in the numerical information in FIG. 4 of the table storage section 23 and saves it.

Figure 11:
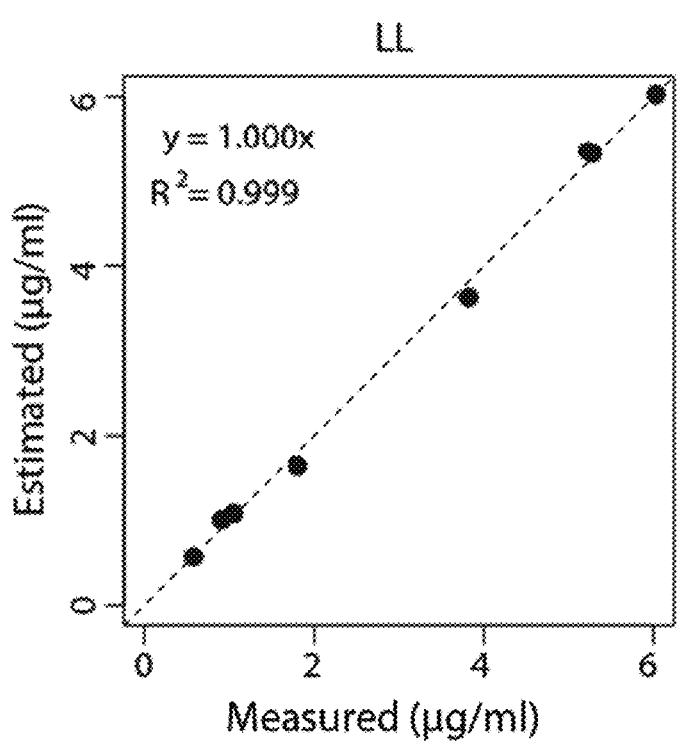
FIG. 11 is a graph showing the correlation between the pigment amount (μg/ml) obtained by converting the actually measured pigment amount per cell of chlorophyll accumulated in monitoring target cells (*Haematococcus*) into the pigment amount per 1 ml of the culture liquid, and the pigment amount estimated from a multiple regression equation using the mean intensities of R pixels, G pixels, and B pixels in the pixels of the cell image.

FIG. 11 is a graph showing the correlation between the actually measured pigment amount per 1 ml of a culture liquid for chlorophyll accumulated in the monitoring target cells (*Haematococcus*) and the pigment amount estimated from the multiple regression equation using the mean intensity values of R pixels, G pixels, and B pixels in the pixels in the cell image. In the graph of FIG. 11, the vertical axis indicates the chlorophyll amount (µg/ml) per 1 ml of a culture liquid converted from the accumulated amount (pg: picogram) of chlorophyll per cell estimated from the multiple regression equation, and the horizontal axis indicates the actually measured chlorophyll amount (µg/ml) per 1 ml of the culture liquid. The coefficient of determination $R^2$ of the correlation in FIG. 11 is 0.999. The multiple regression equation for estimating the chlorophyll amount is obtained by the multiple regression analysis measuring the correlation between the intensity values of each of R pixels, G pixels, and B pixels in the pixels in the cell image and the actually measured chlorophyll amount per cell.

FIG. 11 shows the correlation between the actually measured value of the chlorophyll amount in the monitoring target cell (cell cultured under a LL condition) used as training data and the estimated amount of chlorophyll determined using the multiple regression equation built from the intensity values of R pixels, G pixels, and B pixels determined from the cell image of the monitoring target cell used as the training data. In addition, for the measurement of the chlorophyll amount per 1 ml of a culture liquid, using the same procedure of chlorophyll extraction as in the description of FIG. 6, chlorophyll is extracted from the cell, and the chlorophyll amount per 1 ml of a culture liquid is determined. The LL condition refers to the culture condition in which cells are left in the environment in a constant bright state of a predetermined illuminance while the cells are cultured.

Figure 12:
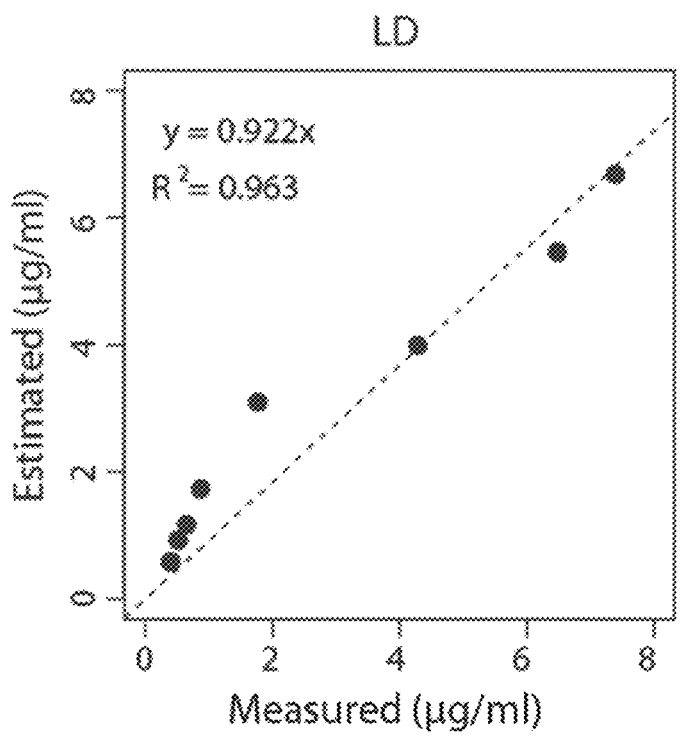
FIG. 12 is a graph showing the correlation between the pigment amount (μg/ml) obtained by converting the actually measured pigment amount per cell of chlorophyll accumulated in monitoring target cells (*Haematococcus*) into the pigment amount per 1 ml of the culture liquid, and the pigment amount estimated from a multiple regression equation using the mean intensities of R pixels, G pixels, and B pixels in the pixels of the cell image.

FIG. 12 is a graph showing the correlation between the actually measured pigment amount per 1 ml of a culture liquid for chlorophyll accumulated in monitoring target cells (*Haematococcus*) and the pigment amount estimated from the multiple regression equation using the mean intensity values of R pixels, G pixels, and B pixels in the pixels in the cell image. In the graph of FIG. 12, in the same manner as in the graph of FIG. 11, the vertical axis indicates the chlorophyll amount (μg/ml) per 1 ml of a culture liquid converted from the accumulated amount (pg: picogram) of chlorophyll per cell estimated from the multiple regression equation, and the horizontal axis indicates the actually measured chlorophyll amount (μg/ml) per 1 ml of a culture liquid. The coefficient of determination $R^2$ of the correlation in FIG. 12 is 0.963. The multiple regression equation for estimating the chlorophyll amount is built by the multiple regression analysis measuring the correlation between the intensity values of respective R pixels, G pixels, and B pixels in the pixels in the cell image and the actually measured chlorophyll amount per cell.

FIG. 12 shows the correlation between the actually measured value of the chlorophyll amount in the monitoring target cell (cell cultured under a LD condition) used as the test data and the estimated amount of chlorophyll determined using the multiple regression equation from the intensity values of R pixels, G pixels, and B pixels built from the cell image of the monitoring target cell used as the test data. In addition, for the measurement of the chlorophyll amount per 1 ml of a culture liquid, using the same treatment for extracting chlorophyll as that in description of FIG. 6, chlorophyll is extracted from the cell, and the chlorophyll amount per 1 ml of a culture liquid is determined. The LD condition is the culture condition in which cells are left in the environment in which a bright state of a predetermined illuminance and a dark state of a predetermined illuminance are repeated with a predetermined cycle while the cells are cultured.

In addition, in FIG. 12, as described above, using the multiple regression equation built from the cell cultured under the LL condition described in FIG. 11 as training data, the chlorophyll amount per 1 ml of a culture liquid is measured from the test data of the cells cultured under the LD condition. Culture conditions of the LL condition and the LD condition are different from each other, and thus they are completely different as the statistical populations. However, the coefficient of determination $R^2$ of the correlation between the actually measured value and the estimated value in FIG. 12 is 0.963, and even in this case where the multiple regression equations built from different populations are used (populations of the cells cultured under the LL condition), a high correlation is observed between the actually measured value of the chlorophyll amount in the cell cultured under the LD condition and the estimate value of the chlorophyll amount estimated using the multiple regression equation built from the cells cultured under the LL condition. Thus, it is found that the multiple regression equation for estimating the chlorophyll amount in the embodiment can perform an estimation process of the chlorophyll amount with high precision.

Figure 13:
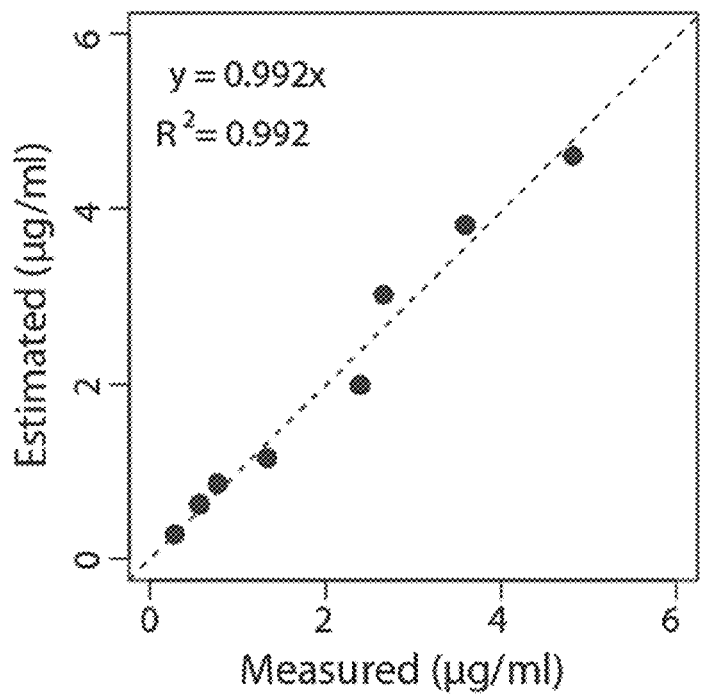
FIG. 13 is a graph showing the correlation between the pigment amount (μg/ml) obtained by converting the actually measured pigment amount per cell of astaxanthin accumulated in monitoring target cells (*Haematococcus*) into the pigment amount per 1 ml of the culture liquid, and the astaxanthin pigment amount estimated from a multiple regression equation using the mean intensities of R pixels, G pixels, and B pixels in the pixels of the cell image.

FIG. 13 is a graph showing the correlation between the pigment amount per 1 ml of a culture liquid of astaxanthin accumulated in actually measured monitoring target cells (*Haematococcus*) and the pigment amount of the astaxanthin estimated from the multiple regression equation using the mean intensity values of R pixels, G pixels, and B pixels in the pixels in the cell image. In the graph of FIG. 13, the vertical axis indicates the astaxanthin amount (μg/ml) per 1 ml of a culture liquid converted from the accumulated amount (pg: picogram) of astaxanthin per cell estimated, and the horizontal axis indicates the astaxanthin amount (μg/ml) per 1 ml of a culture liquid actually measured. The coefficient of determination $R^2$ of correlation in FIG. 13 is 0.963.

FIG. 13 shows the correlation between the actually measured value of the astaxanthin amount in the monitoring target cell (cell cultured under a LL condition) used as training data and the estimated amount determined using the multiple regression equation from the intensity values of R pixels, G pixels, and B pixels determined from the cell image of the monitoring target cell used as the training data. In addition, the measurement of the astaxanthin amount per 1 ml of a culture liquid is performed the same treatment for extracting astaxanthin as that in description of FIG. 5, astaxanthin is extracted from the cell, and the astaxanthin amount per 1 ml of a culture liquid is determined. The LL condition is a culture condition in which cells are left to stand in the environment in a bright state of a predetermined illuminance always when the cells are cultured.

Figure 14:
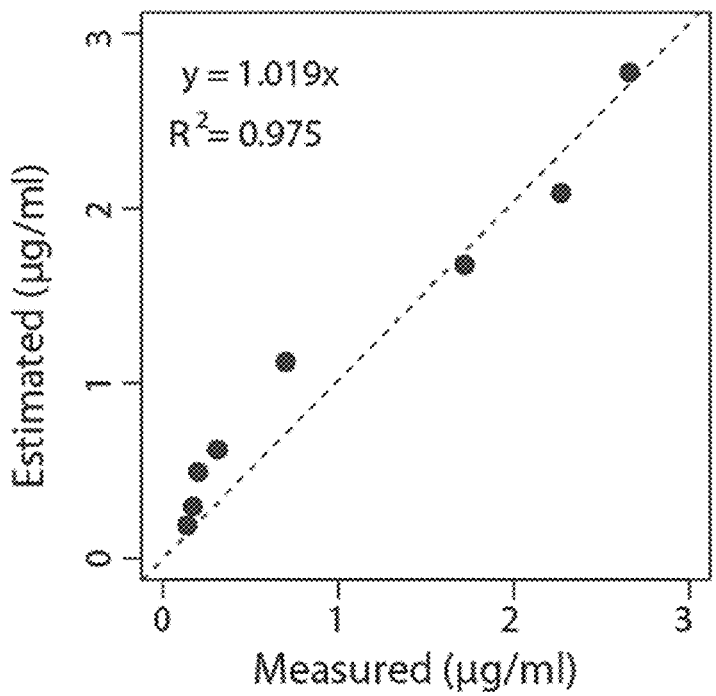
FIG. 14 is a graph showing the correlation between the pigment amount (μg/ml) obtained by converting the actually measured pigment amount per cell of astaxanthin accumulated in monitoring target cells (*Haematococcus*) into the pigment amount per 1 ml of the culture liquid, and the astaxanthin pigment amount estimated from a multiple regression equation using the mean intensities of R pixels, G pixels, and B pixels in the pixels of the cell image.

FIG. 14 is a graph showing the correlation between the pigment amount per 1 ml of a culture liquid of astaxanthin accumulated in actually measured monitoring target cells (*Haematococcus*) and the pigment amount of the astaxanthin estimated from the multiple regression equation using the mean intensity values of R pixels, G pixels, and B pixels for the pixels in the cell image. In the graph of FIG. 14, in the same manner as in the graph of FIG. 13, the vertical axis indicates the astaxanthin amount (μg/ml) per 1 ml of a culture liquid converted from the accumulated amount (pg: picogram) of astaxanthin per cell estimated, and the horizontal axis indicates the astaxanthin amount (μg/ml) per 1 ml of a culture liquid actually measured. The coefficient of determination $R^2$ of correlation in FIG. 14 is 0.975.

FIG. 14 shows the correlation between the actually measured value of the astaxanthin amount in the monitoring target cell (cell cultured under the LD condition) used as test data and the estimated amount determined using the regression equation from the intensity values of R pixels, G pixels, and B pixels determined from the cell image of the monitoring target cell used as the test data. In addition, the measurement of the astaxanthin amount per 1 ml of a culture liquid is performed the same treatment for extracting astaxanthin as that in description of FIG. 5, astaxanthin is extracted from the cell, and the astaxanthin amount per 1 ml of a culture liquid is determined. The LD condition is a culture condition in which cells are left to stand in the environment in which a bright state of a predetermined illuminance and a dark state of a predetermined illuminance are repeated with a preset period when the cells are cultured.

In addition, in FIG. 14, as described above, using the multiple regression equation built using the cell cultured under the LL condition described in FIG. 13 as training data, the astaxanthin amount per 1 ml of a culture liquid using the cell cultured under the LD condition as test data is measured. Culture conditions of the LL condition and the LD condition are different from each other, and the statistical parent populations of cultured cells are completely different. However, the coefficient of determination $R^2$ of correlation between the actually measured value and the estimated value in FIG. 14 is 0.975, and even in the case of the multiple regression equation built from different populations (populations of the cells cultured under the LL condition), a high correlation is present between the actually measured value of the astaxanthin amount in the cell cultured under the LD condition and the estimate value of the astaxanthin amount estimated by the multiple regression equation built using cells cultured under the LL condition. Thus, it is found that the multiple regression equation for estimating the astaxanthin amount in the embodiment can perform an estimation process of the astaxanthin amount with high precision.

Figure 15:
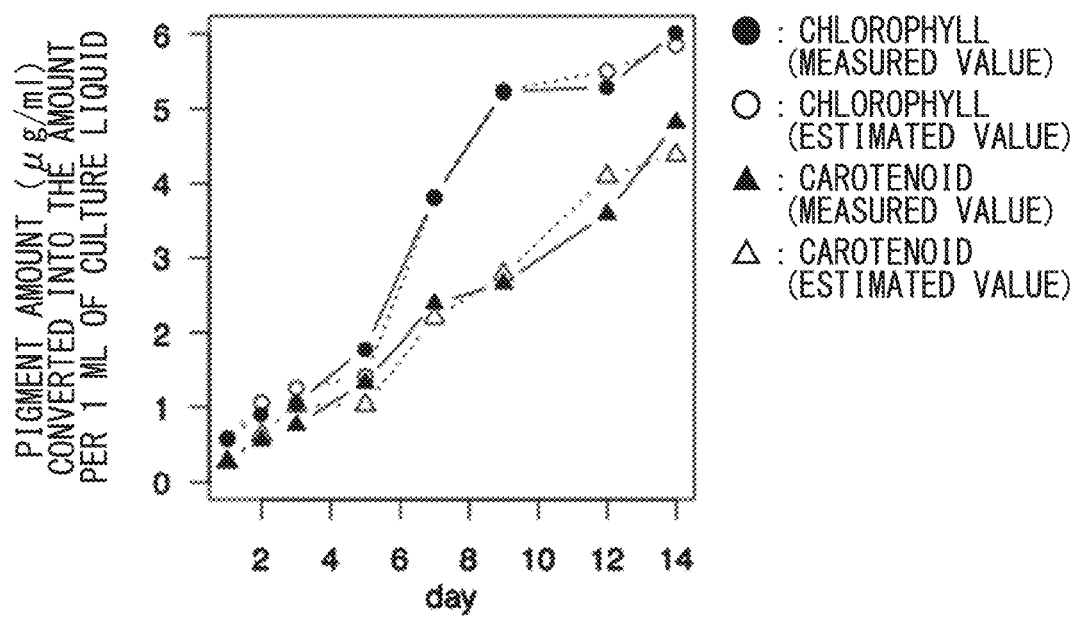
FIG. 15 is a graph showing the equation of the multiple regression analysis used for estimating each of the chlorophyll amount and the carotenoid amount.

FIG. 15 is a graph showing the equation of the multiple regression analysis used for estimating each of the chlorophyll amount and the carotenoid amount. In the graph in FIG. 15, the vertical axis indicates the pigment amount (μg/ml) converted into the amount per 1 ml of a culture liquid, and the horizontal axis indicates the time (the number of days) elapsed from the start of the culture. In FIG. 15, the black circle indicates the measured value of the chlorophyll amount actually measured, and the white circle indicates the chlorophyll amount estimated by the multiple regression equation. In addition, the black triangle indicates the measured value of the carotenoid amount actually measured, and the white triangle indicates the carotenoid amount estimated by the multiple regression equation.

In addition, the multiple regression equation (also shown in FIG. 15) of the chlorophyll concentration (pg/cell) shown below estimates the chlorophyll amount included in one cell.

$$Y_{chl} = -0.46 \times I_R + 0.56 \times I_G - 0.83 \times I_B - 72.01$$

In addition, the multiple regression equation (also shown in FIG. 15) of the carotenoid concentration (pg/cell) shown below estimates the carotenoid amount included in one cell.

$$Y_{car} = 0.75 \times I_R - 0.22 \times I_G - 0.27 \times I_B - 61.83$$

In addition, in these multiple regression equations, $Y_{chl}$ indicates the chlorophyll concentration, and $Y_{car}$ indicates the carotenoid concentration. $I_R$ is the mean intensity value of the red channel in the pigmented region in the cell image. $I_G$ is the mean intensity value of the green channel in the pigmented region in the cell image. $I_B$ is the mean intensity value of the blue channel in the pigmented region in the cell image.

The above-described multiple regression equations are built by determining each values of coefficients a, b, c, and d in the following basic equation by the multiple regression analysis.

$$Y = aI_R + bI_G + cI_B + d$$

In the above equation, the coefficient a is a coefficient to be multiplied with the mean intensity value of the red channels in the pixels of a pigmented region. The coefficient b is a coefficient to be multiplied with the mean intensity value of the green channel in the pixels of a pigmented region. The coefficient c is a coefficient which is to be multiplied with the mean intensity value of the blue channels in the pixels of a pigmented region. The coefficient d is a constant in the multiple regression equation.

<Discrimination of Zoospore from Palmelloid of *Haematococcus* by Random Forest Method>

Next, the discrimination process is described in which whether the cultured cell of the monitoring target is a zoospore or a palmelloid is determined by the random forest method. In this section, basically, using a machine learning using the random forest method, a tree model is generated for a clustering process which identifies cells shown in cell images included in a captured image into either zoospore and palmelloid respectively. The generated tree model is written in the storage section 22 in advance and saved. In the embodiment, a palmelloid is also referred to as a palmelloid cell.

Furthermore, the cell morphology detecting section 19 reads the tree model from the storage section 22, and performs clustering of the cell images included in the captured image by the tree model. In addition, the cell morphology detecting section 19 causes the clustering result to be displayed on the display 24 as a clustering image (for example, a graph of FIG. 20 described below), and causes the proportion at that moment of the zoospore and the palmelloid or the like to be visually expressed. By viewing this clustering image, it is possible to easily visually estimate the proportion at the moment of the zoospore and the palmelloid.

In addition, the cell morphology detecting section 19 may be constituted such that the machine learning by the random forest method is repeated and the tree model is continuously updated by inputting the correct clustering result.

Figure 16:
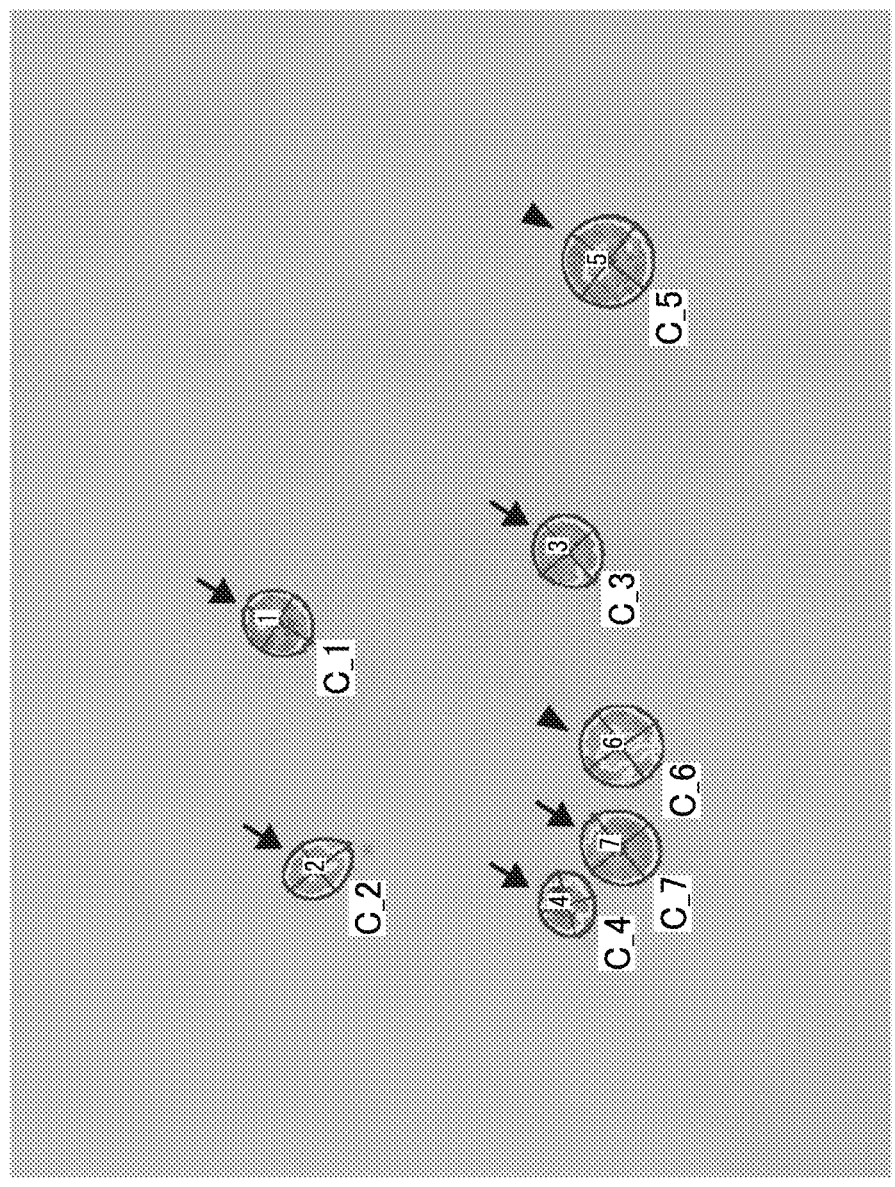
FIG. 16 shows a captured image in which zoospores and palmelloids are pictured.

FIG. 16 is a diagram showing a captured image in which both zoospores and palmelloids are captured. In FIG. 16, cells indicated by black triangles are palmelloids, and cells indicated by arrows are zoospores. That is, cells C_1, C_2, C_3, C_4, and C_7 are zoospores, and cells C_5 and C_6 are palmelloids.

When an observer is manually observing the cells using a microscope, the distinction between a palmelloid and a zoospore is easy since a zoospore has flagella or the like. However, it is difficult for the observer to classify a large amount of cells in culture, and to determine the ratio of the number of the palmelloids and the number of the zoospores.

To resolve the problems described above, each of the cultured cells are numerically clustered using the tree model and the clustering result is visually displayed on a display device. Thus, it is possible to clearly notify the proportion of the zoospore and the palmelloid.

Figure 17:
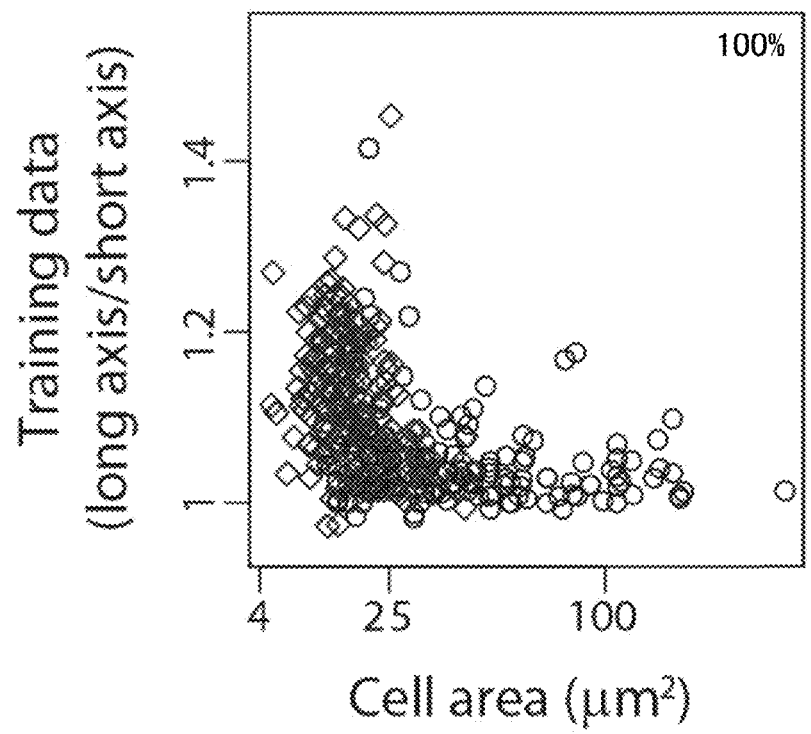
FIG. 17 is a graph showing the clustering result of the cultured cells of training data by a tree model generated using two parameters of the cultured cells in the training data by the random forest method.

FIG. 17 is a graph showing a result of clustering the cultured cells of training data by the tree model generated using two parameters of the cultured cells of the training data by the random forest method. The two parameters are: the ratio of the long diameter to the short diameter, i.e., OuterAxisRatio (L/S) which is numerical information of the cell image obtained from the image analysis by the cell monitoring device 1; and the area size of the cell image, i.e., OuterArea. In FIG. 17, the vertical axis indicates the ratio of the long diameter to the short diameter of the cell image, i.e., OuterAxisRatio (L/S), and the horizontal axis indicates the area size of the cell image, i.e., OuterArea. In FIG. 17, correct classification ratio of cells of the training data by the tree model generated by the cells of the training data is 100%. The correct classification ratio is the percentage of the correct classification results in which the classification result correctly classifies a zoospore as a zoospore and a palmelloid as a palmelloid. In each of this FIG. 17 and FIGS. 18, 19 and 20 described below, the white circle indicates a palmelloid cell, and the white diamond indicates a zoospore cell.

Figure 18:
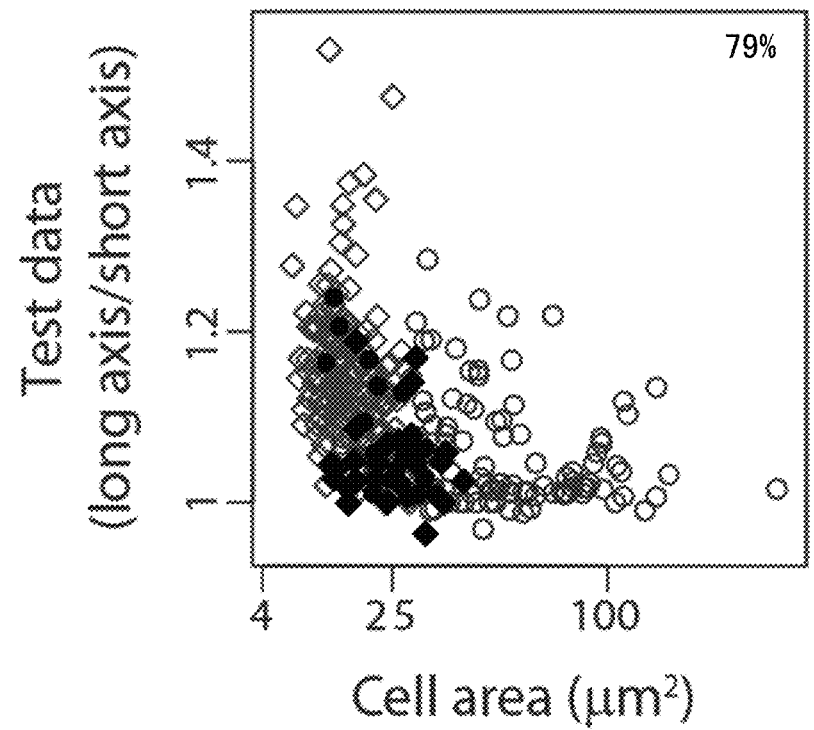
FIG. 18 is a graph showing the clustering result of the cultured cells of test data by a tree model generated using two parameters of the cultured cells in the training data by the random forest method.

FIG. 18 is a graph showing the clustering result of the cultured cells of test data. The clustering employed the random forest method with a tree model generated using two parameters of the cultured cells of the training data. The two parameters, in the same manner as in the case of FIG. 16, are the ratio of the long diameter to the short diameter, i.e., OuterAxisRatio (L/S) and the area of the cell image, i.e., OuterArea. OuterAxisRatio (L/S) is numerical information of the cell image obtained from the image analysis by the cell monitoring device 1. In FIG. 18, as in FIG. 17, the vertical axis indicates the ratio of the long diameter to the short diameter of the cell image, i.e., OuterAxisRatio (L/S), and the horizontal axis indicates the area of the cell image, i.e., OuterArea. In FIG. 18, correct classification ratio of cells in the test data by the tree model generated by the cells in the training data is 79%.

In addition, respective cells of the training data and the test data are obtained by dividing 682 cells extracted from the parent population which is *Haematococcus* cells on the 2nd day or the 3rd day transferred to a fresh culture medium into two groups, i.e., a cell group of the training data having 341 cells and a cell group of the test data having 341 cells.

Figure 19:
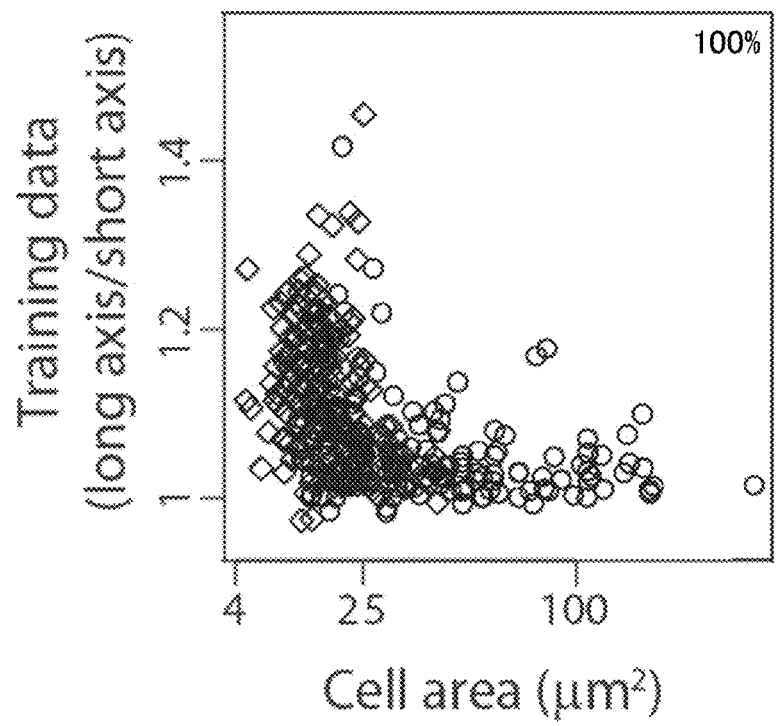
FIG. 19 is a graph showing a result of clustering the cultured cells of training data by a tree model generated using twenty five parameters of the cultured cells in the training data by machine learning of the random forest method.

FIG. 19 is a graph showing a result of clustering the cultured cells of training data by a tree model generated using twenty five parameters of the cultured cells of the training data by machine learning of the random forest method. The twenty five parameters are the ratio of the long diameter to the short diameter, i.e., OuterAxisRatio (L/S) which is numerical information of the cell image obtained from an image analysis by the cell monitoring device 1, the area of the cell image, i.e., OuterArea, and respective parameters obtained from an image analysis by the cell monitoring device 1 described in FIG. 3 or 4. In addition, in FIG. 19, the vertical axis indicates the ratio of the long diameter to the short diameter of the cell image, i.e., OuterAxisRatio (L/S), and the horizontal axis indicates the area of the cell image, i.e., OuterArea. In FIG. 19, correct classification ratio of cells of the training data by the tree model generated by the cells of the training data is 100%.

Figure 20:
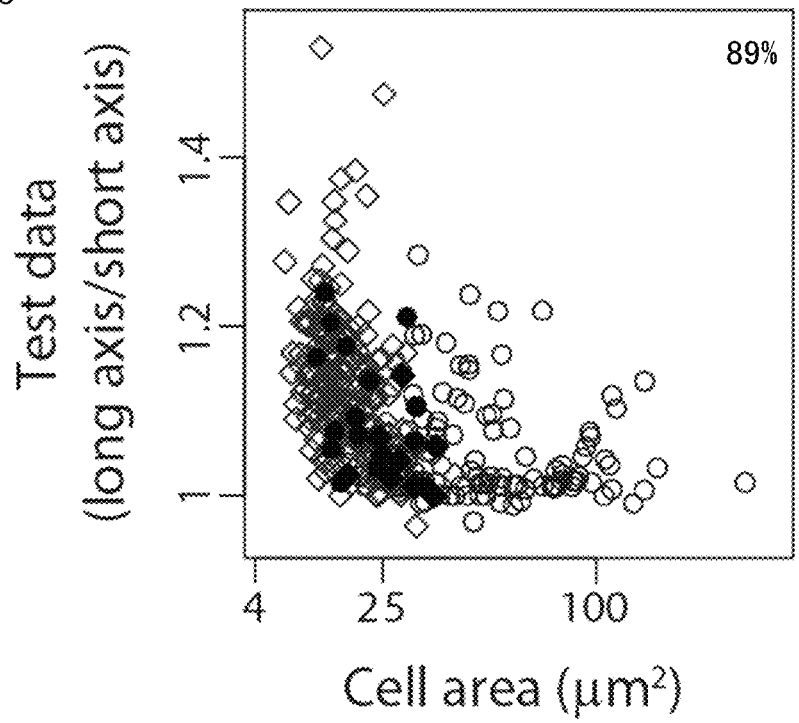
FIG. 20 is a graph showing a result of clustering the cultured cells of test data by a tree model generated using twenty five parameters of the cultured cells in the training data by machine learning of the random forest method.

FIG. 20 is a graph showing a result of clustering the cultured cells of test data by a tree model generated using twenty five parameters of the cultured cells of the training data by machine learning of the random forest method. The twenty five parameters, in the same manner as in the case of FIG. 19, are the ratio of the long diameter to the short diameter, i.e., OuterAxisRatio (L/S) which is numerical information of the cell image obtained from an image analysis by the cell monitoring device 1, the area of the cell image, i.e., OuterArea, and respective parameters obtained from an image analysis by the cell monitoring device 1 described in FIG. 3 or 4. In addition, in the same manner as in FIG. 19, in FIG. 20, the vertical axis indicates the ratio of the long diameter to the short diameter of the cell image, i.e., OuterAxisRatio (L/S), and the horizontal axis indicates the area of the cell image, i.e., OuterArea. In FIG. 20, correct classification ratio of cells in the test data by the tree model generated by the cells of the training data is 89%.

As described above, it is found that, when two parameters were used, the correct classification ratio of the zoospore and the palmelloid for the cells in the test data was 79%, but, when twenty five parameters were used, the correct classification ratio was 89% which is about 10% more precise value than that in the case of two parameters.

In addition, in each of FIGS. 17 to 20, the discrimination was performed after culture for two days or three days from the start of the cell culture. Therefore, in a case where discrimination is performed by the tree model described above in a time series from the start of the cell culture, it is possible to visually confirm changes of the proportion of the zoospore and the palmelloid by the clustering result as shown in FIGS. 17 to 20.

Furthermore, by increasing the training data using different cell culture strains and updating the tree model, it is possible to further improve the precision of clustering of zoospores and palmelloids, and serial monitoring of the cell culture can become easier by the captured cell image.

Hereinafter, each of the twenty five parameters used in the machine learning in the random forest method in the embodiment will be described. In addition, in all of the following FIGS. 21 to 45, the white circle indicates each of the parameters detected from the cell images of the cells cultured in the LL condition, and the black circle indicates each of the parameters detected from the cell images of the cells cultured in the LD condition. In each of the following figures, in the parameter calculations, when the parameter is the unit of length, the cell structure calculating section 18 counts the number of pixels along the line segment to be measured in the cell image, and determines the actual length from the number of counts, i.e., converts the number of pixels into a numerical value of the length having the unit of μm. When the parameter is an area size, the cell structure calculating section 18 counts the number of pixels in the region to be measured in the cell image, and determines the size of the actual area from the number of counts, i.e., converts the number of pixels into a numerical value having the unit of $μm^2$. In addition, each of the numerical values in FIGS. 21 to 45 is the mean value obtained by averaging the measured values among the cell images.

Figure 21:
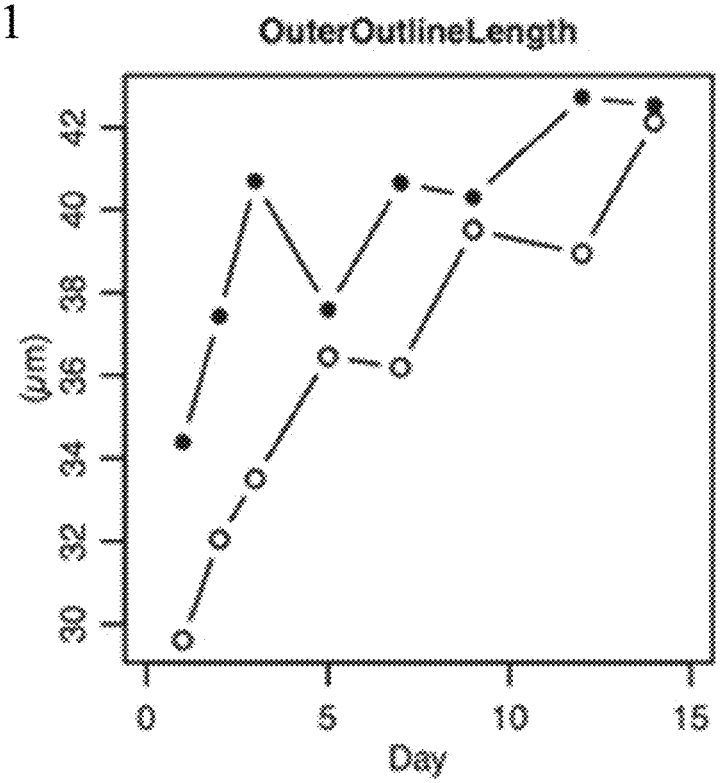
FIG. 21 is a graph showing the correlation between the culture time and OuterOutlineLength (unit: μm) indicating the outline length of the cell image of the cultured cell.

FIG. 21 is a graph showing the correlation between the culture time and OuterOutlineLength (unit: μm) indicating the outline length of the cell image of the cultured cell. In FIG. 21, the vertical axis indicates the measured value of OuterOutlineLength, and the horizontal axis indicates the number of days for which cells are cultured (Day, the same is also applied in each of the following FIGS. 22 to 45).

Figure 22:
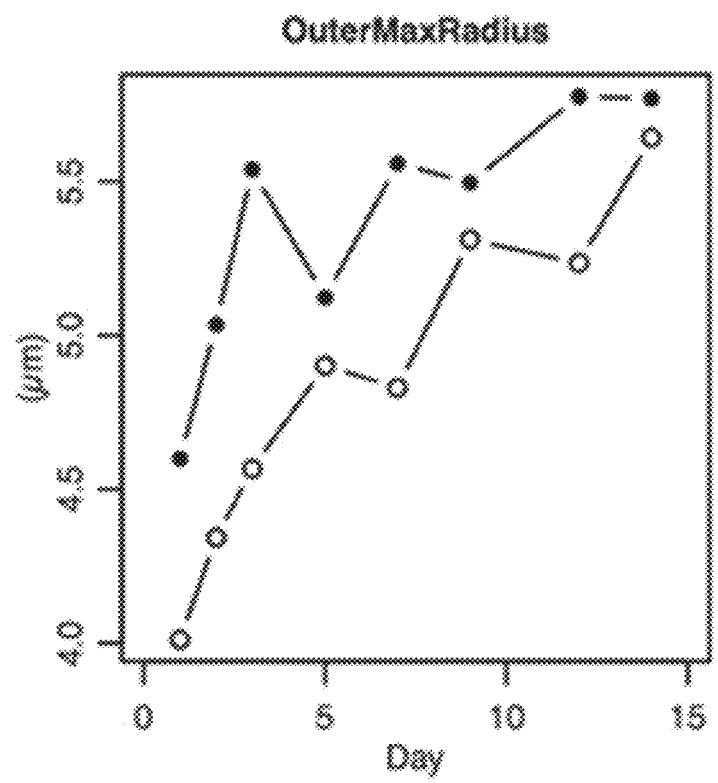
FIG. 22 is a graph showing the correlation between the culture time and OuterMaxRadius (unit: μm), indicating the maximum distance from the gravity center position of the cell image to the outer edge of the cell image for the cultured cell.

FIG. 22 is a graph showing the correlation between the culture time and OuterMaxRadius (unit: μm) indicating the maximum value of the distance from the coordinate of the gravity center in the cell image of the cultured cell to the outer edge of the cell image. In FIG. 22, the vertical axis indicates the measured value of OuterMaxRadius, and the horizontal axis indicates the number of days for which cells are cultured.

Figure 23:
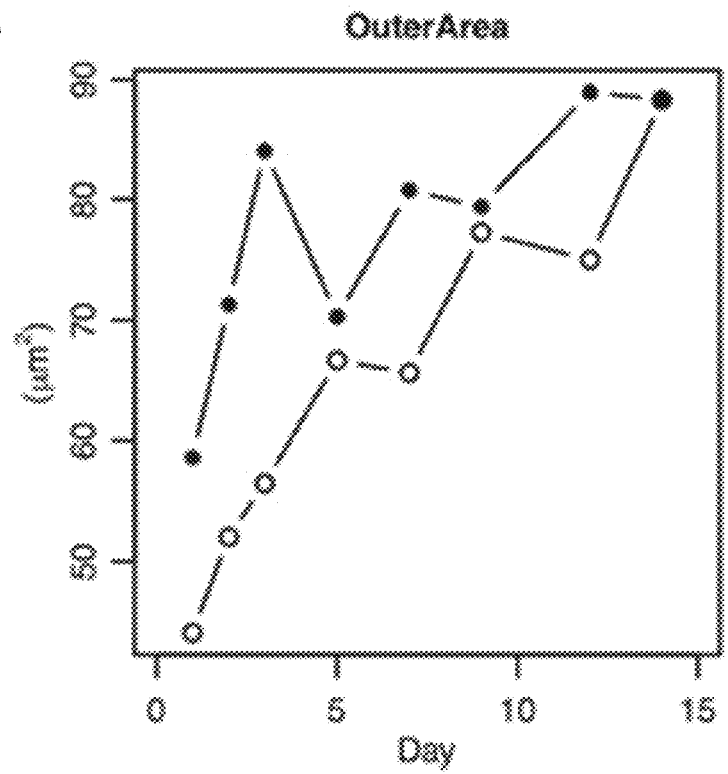
FIG. 23 is a graph showing the correlation between the culture time and OuterArea (unit: $\mu m^2$), indicating the area of the cell image of the cultured cell.

FIG. 23 is a graph showing the correlation between the culture time and OuterArea (unit: $μm^2$) indicating the area of the cell image of the cultured cell. In FIG. 23, the vertical axis indicates the measured value of OuterArea, and the horizontal axis indicates the number of days for which cells are cultured.

Figure 24:
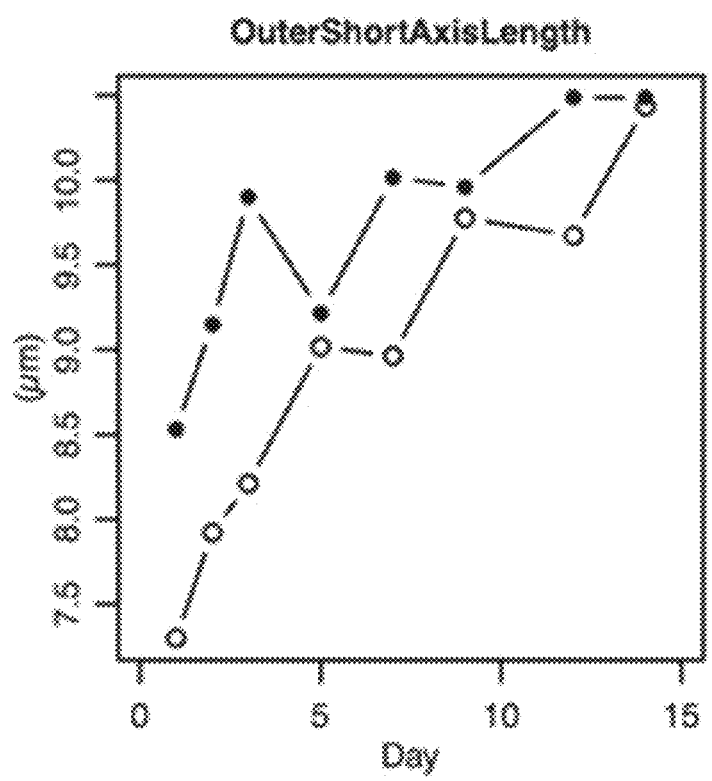
FIG. 24 is a graph showing the correlation between the culture time and OuterShortAxisLength (unit: $\mu m$), indicating the length of the minimum width portion (short axis) in the cell image of the cultured cell.

FIG. 24 is a graph showing the correlation between the culture time and OuterShortAxisLength (unit: μm) indicating the size of the minimum width (short axis) portion in the cell image of the cultured cell. In FIG. 24, the vertical axis indicates the measured value of OuterShortAxisLength, and the horizontal axis indicates the number of days for which cells are cultured.

Figure 25:
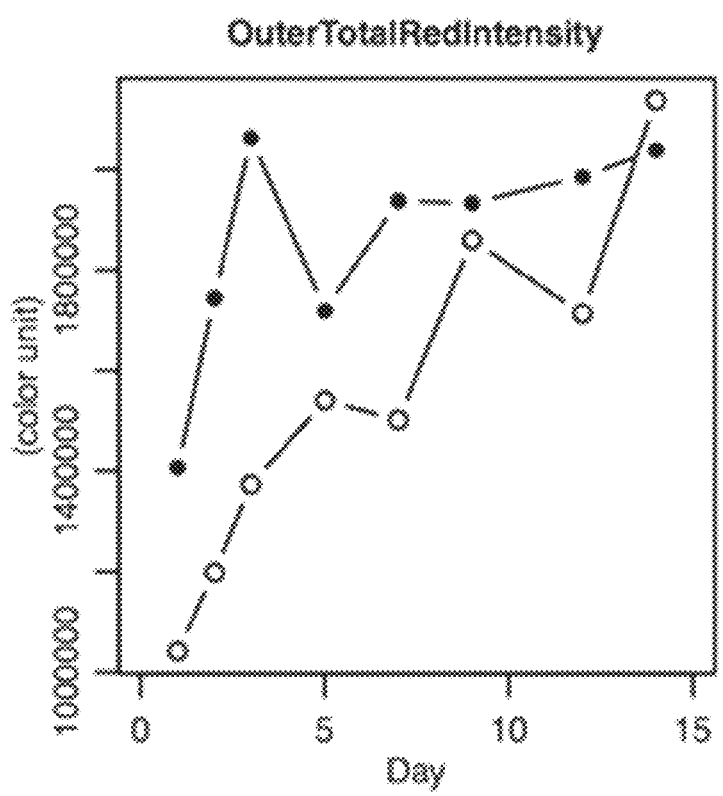
FIG. 25 is a graph showing the correlation between the culture time and OuterTotalRedIntensity (unit: color unit), which is a value indicating the sum of the red channel intensities (R pixels) for the entire area of a cell in the cell image of the cultured cell.

FIG. 25 is a graph showing the correlation between the culture time and OuterTotalRedIntensity (unit: color unit) which is a numerical value indicating the sum of the intensity values of the entire red channels (R pixels) in a cell in the cell image of the cultured cell. In FIG. 25, the vertical axis indicates the measured value of OuterTotalRedIntensity, and the horizontal axis indicates the number of days for which cells are cultured. Here, the cell structure calculating section 18 described above calculates the sum of the intensity values of R pixels in the entire pixels in the cell image, and the summation result is used as OuterTotalRedIntensity.

Figure 26:
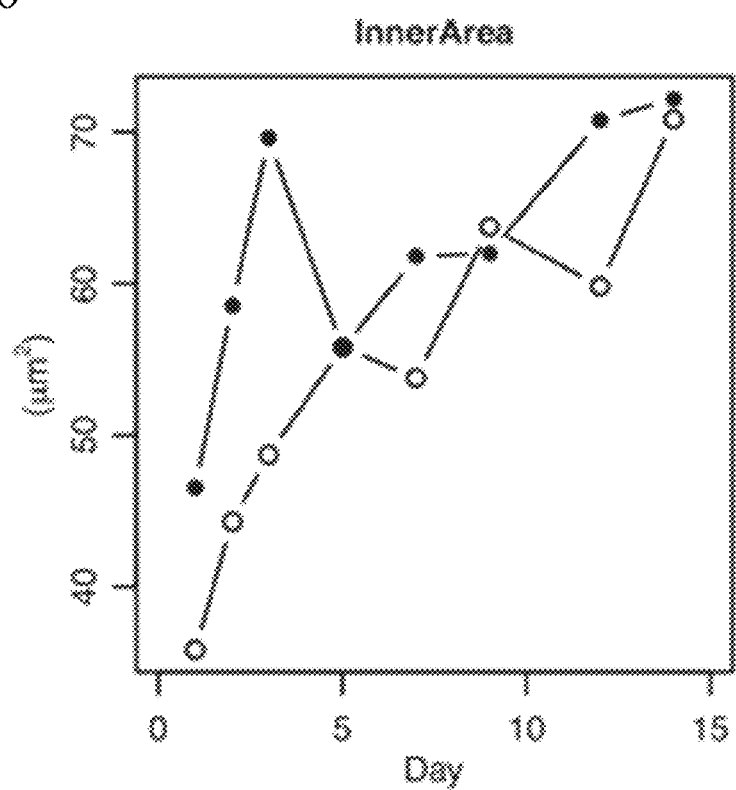
FIG. 26 is a graph showing the correlation between the culture time and InnerArea (unit: $\mu m^2$) indicating the area in a pigmented region in the cell image of the cultured cell.

FIG. 26 is a graph showing the correlation between the culture time and InnerArea (unit: $μm^2$) indicating the area of a pigmented region in the cell image of the cultured cell. In FIG. 26, the vertical axis indicates the measured value of InnerArea, and the horizontal axis indicates the number of days for which cells are cultured.

Figure 27:
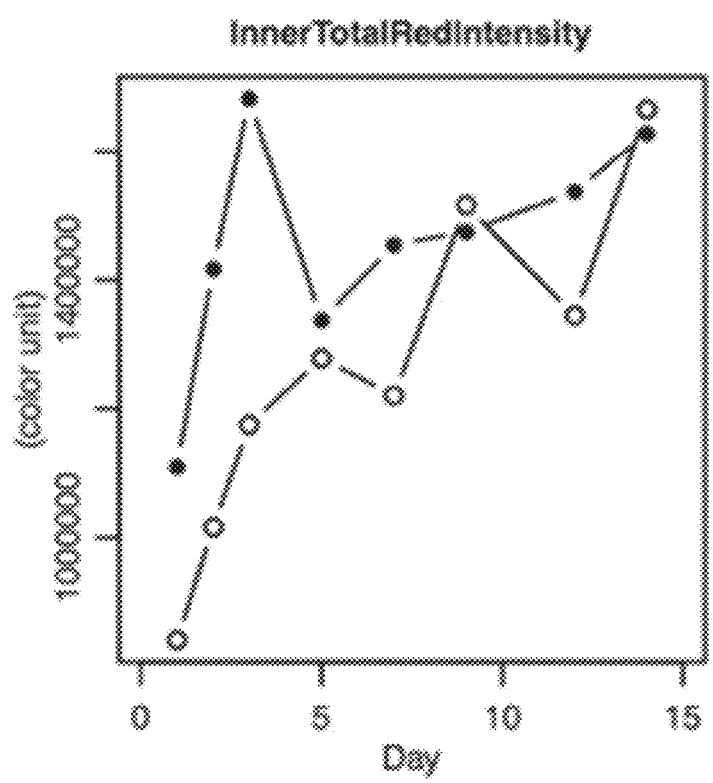
FIG. 27 is a graph showing the correlation between the culture time and InnerTotalRedIntensity (unit: color unit) which is a numerical value indicating the sum of the red channel intensities (R pixels) in a pigmented region of the cell image.

FIG. 27 is a graph showing the correlation between the culture time and InnerTotalRedIntensity (unit: color unit) which is a numerical value indicating the sum of the intensity values of the red channels (R pixels) in a pigmented region of the cell image. In FIG. 27, the vertical axis indicates the measured value of InnerTotalRedIntensity, and the horizontal axis indicates the number of days for which cells are cultured. Here, the cell structure calculating section 18 described above calculates the sum of the intensity values of R pixels in the entire pixels in the pigmented region in the cell image, and the summation result is used as InnerTotalRedIntensity.

Figure 28:
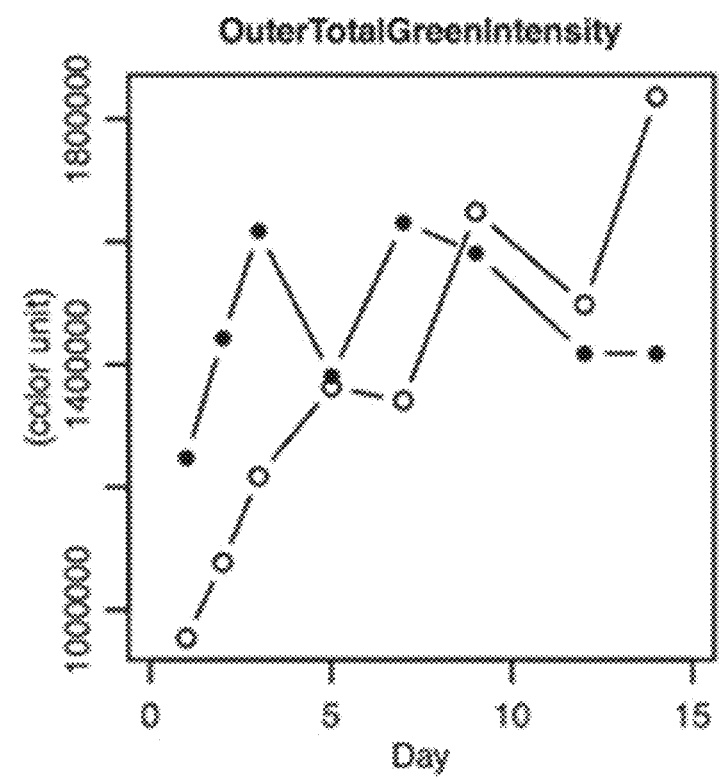
FIG. 28 is a graph showing the correlation between the culture time and OuterTotalGreenIntensity (unit: color unit) which is a numerical value indicating the sum of the intensity values of the entire green channels (G pixels) in a cell in the cell image of the cultured cell.

FIG. 28 is a graph showing the correlation between the culture time and OuterTotalGreenIntensity (unit: color unit) which is a numerical value indicating the sum of the intensity values of the entire green channels (G pixels) in a cell in the cell image of the cultured cell. In FIG. 28, the vertical axis indicates the measured value of OuterTotalGreenIntensity, and the horizontal axis indicates the number of days for which cells are cultured. Here, the cell structure calculating section 18 described above calculates the sum of the intensity values of G pixels in the entire pixels in the cell image, and the summation result is used as OuterTotalGreenIntensity.

Figure 29:
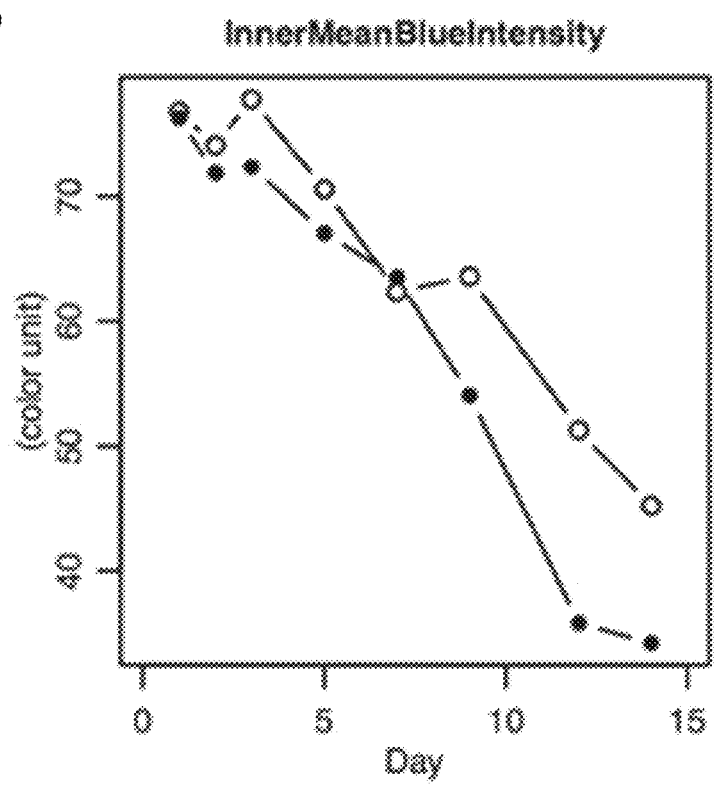
FIG. 29 is a graph showing the correlation between the culture time and InnerMeanBlueIntensity (unit: color unit) which is a numerical value indicating the mean intensity value of the blue channels (B pixels) in a pigmented region of the cell image.

FIG. 29 is a graph showing the correlation between the culture time and InnerMeanBlueIntensity (unit: color unit) which is a numerical value indicating the mean intensity value of the blue channels (B pixels) in a pigmented region of the cell image. In FIG. 29, the vertical axis indicates the measured value of InnerMeanBlueIntensity, and the horizontal axis indicates the number of days for which cells are cultured. Here, the cell structure calculating section 18 described above calculates the mean intensity value of B pixels in the entire pixels in the pigmented region in the cell image, and the calculation result is used as InnerMeanBlueIntensity.

Figure 30:
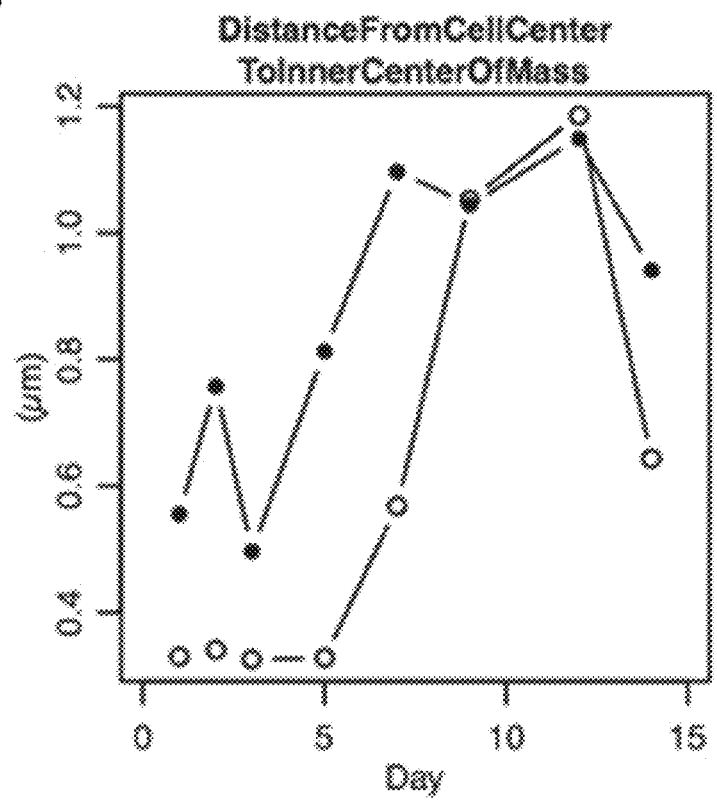
FIG. 30 is a graph showing the correlation between the culture time and DistanceFromCellCenterToInnerCenterOfMass (unit: $\mu m$) which is a numerical value indicating the distance from the center point to the gravity center in the cell image of the cultured cell.

FIG. 30 is a graph showing the correlation between the culture time and DistanceFromCellCenterToInnerCenterOfMass (unit: μm) which is a numerical value indicating the distance from the center point to the gravity center in the cell image of the cultured cell. In FIG. 30, the vertical axis indicates the measured value of DistanceFromCellCenterToInnerCenterOfMass, and the horizontal axis indicates the number of days for which cells are cultured. The cell structure calculating section 18 described above determines the center coordinate value of the cell image and the coordinate value of the gravity center of the cell image from the pixel values of the cell image, and determines the difference between the center coordinate value and the coordinate value of the gravity center, and the difference is used as DistanceFromCellCenterToInnerCenterOfMass.

Figure 31:
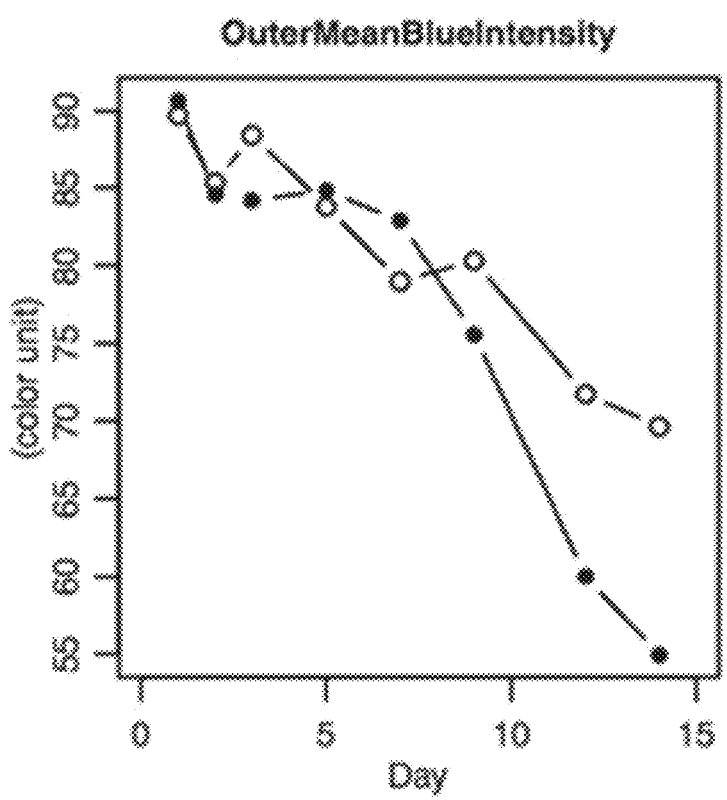
FIG. 31 is a graph showing the correlation between the culture time and OuterMeanBlueIntensity (unit: color unit) which is a numerical value indicating the mean intensity value of the blue channels (B pixels) in a cell in the cell image of the cultured cell.

FIG. 31 is a graph showing the correlation between the culture time and OuterMeanBlueIntensity (unit: color unit) which is a numerical value indicating the mean intensity value of the blue channels (B pixels) in a cell in the cell image of the cultured cell. In FIG. 31, the vertical axis indicates the measured value of OuterMeanBlueIntensity, and the horizontal axis indicates the number of days for which cells are cultured. Here, the cell structure calculating section 18 described above calculates the mean intensity value of B pixels in the entire pixels in the cell image, and the calculation result is used as OuterMeanBlueIntensity.

Figure 32:
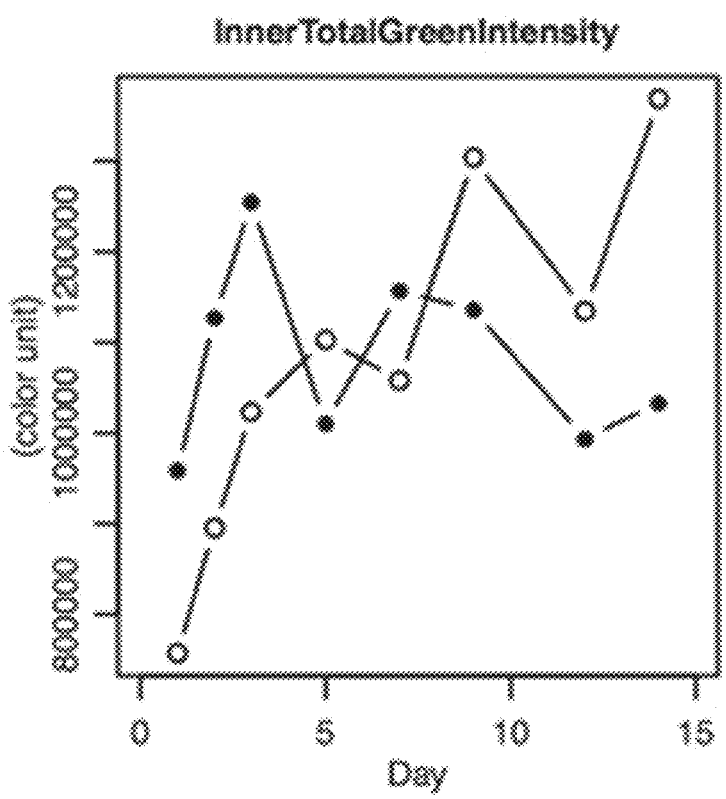
FIG. 32 is a graph showing the correlation between the culture time and InnerTotalGreenIntensity (unit: color unit) which is a numerical value indicating the sum of the intensity values of the green channels (G pixels) in a pigmented region of the cell image.

FIG. 32 is a graph showing the correlation between the culture time and InnerTotalGreenIntensity (unit: color unit) which is a numerical value indicating the sum of the intensity values of the green channels (G pixels) in a pigmented region of the cell image. In FIG. 32, the vertical axis indicates the measured value of InnerTotalGreenIntensity, and the horizontal axis indicates the number of days for which cells are cultured. Here, the cell structure calculating section 18 described above calculates the sum of the intensity values of G pixels in the entire pixels in the pigmented region in the cell image, and the summation result is used as InnerTotalGreenIntensity.

Figure 33:
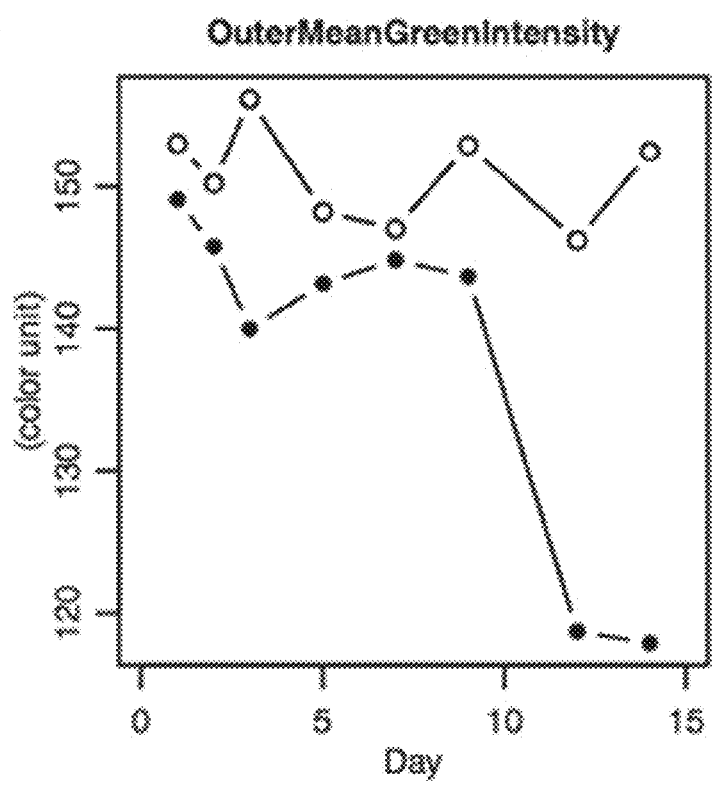
FIG. 33 is a graph showing the correlation between the culture time and OuterMeanGreenIntensity (unit: color unit) which is a numerical value indicating the mean intensity value of the green channels (G pixels) in a cell in the cell image of the cultured cell.

FIG. 33 is a graph showing the correlation between the culture time and OuterMeanGreenIntensity (unit: color unit) which is a numerical value indicating the mean intensity value of the green channels (G pixels) in a cell in the cell image of the cultured cell. In FIG. 33, the vertical axis indicates the measured value of OuterMeanGreenIntensity, and the horizontal axis indicates the number of days for which cells are cultured. Here, the cell structure calculating section 18 described above calculates the mean intensity of G pixels in the entire pixels in the cell image, and the calculation result is used as OuterMeanGreenIntensity.

Figure 34:
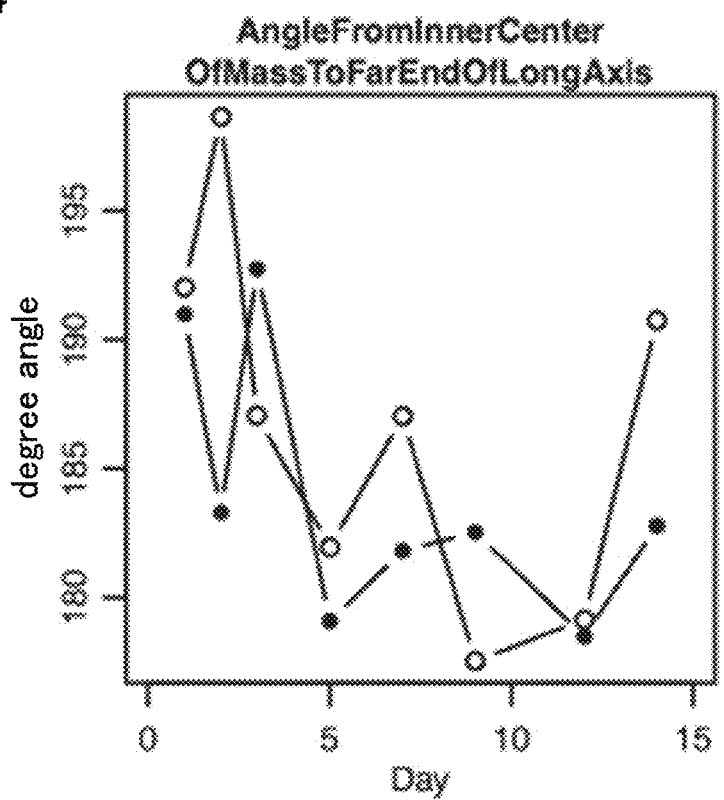
FIG. 34 is a graph showing the correlation between the culture time and AngleFromInnerCenterOfMassToFarEndOfLongAxis (unit: degree of angle) indicating the angle from the gravity center to the farthest coordinate point of the long axis in the cell image.

FIG. 34 is a graph showing the correlation between the culture time and AngleFromInnerCenterOfMassToFarEndOfLongAxis (unit: degree of angle) indicating the angle from the gravity center to the farthest coordinate point of the long axis in the cell image. In FIG. 34, the vertical axis indicates the measured value of AngleFromInnerCenterOfMassToFarEndOfLongAxis, and the horizontal axis indicates the number of days for which cells are cultured. The cell structure calculating section 18 described above determines the coordinate value of the gravity center of the cell image from the pixel values of the cell image, determines the farthest point coordinate value on the long axis from the gravity center coordinates of the cell image, and calculates the angle between the straight line connecting from this furthest point to the gravity center and the long axis of the cell image, and this angle is used as AngleFromInnerCenterOfMassToFarEndOfLongAxis.

Figure 35:
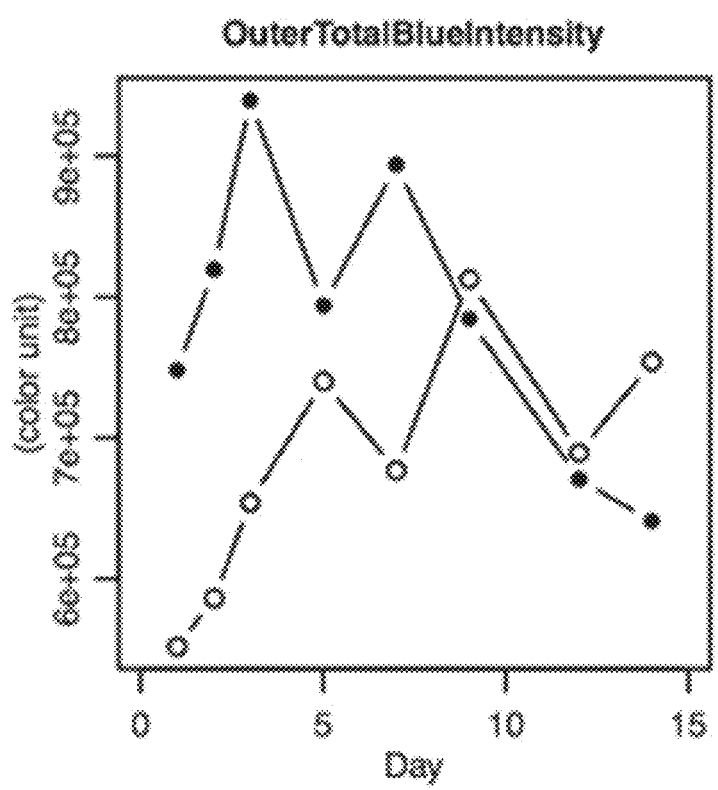
FIG. 35 is a graph showing the correlation between the culture time and OuterTotalBlueIntensity (unit: color unit) which is a numerical value indicating the sum of the intensity values of the entire blue channels (B pixels) in a cell in the cell image of the cultured cell.

FIG. 35 is a graph showing the correlation between the culture time and OuterTotalBlueIntensity (unit: color unit) which is a numerical value indicating the sum of the intensity values of the entire blue channels (B pixels) in a cell in the cell image of the cultured cell. In FIG. 35, the vertical axis indicates the measured value of OuterTotalBlueIntensity, and the horizontal axis indicates the number of days for which cells are cultured. Here, the cell structure calculating section 18 described above calculates the sum of the intensity values of B pixels in the entire pixels in the cell image, and the summation result is used as OuterTotalBlueIntensity.

Figure 36:
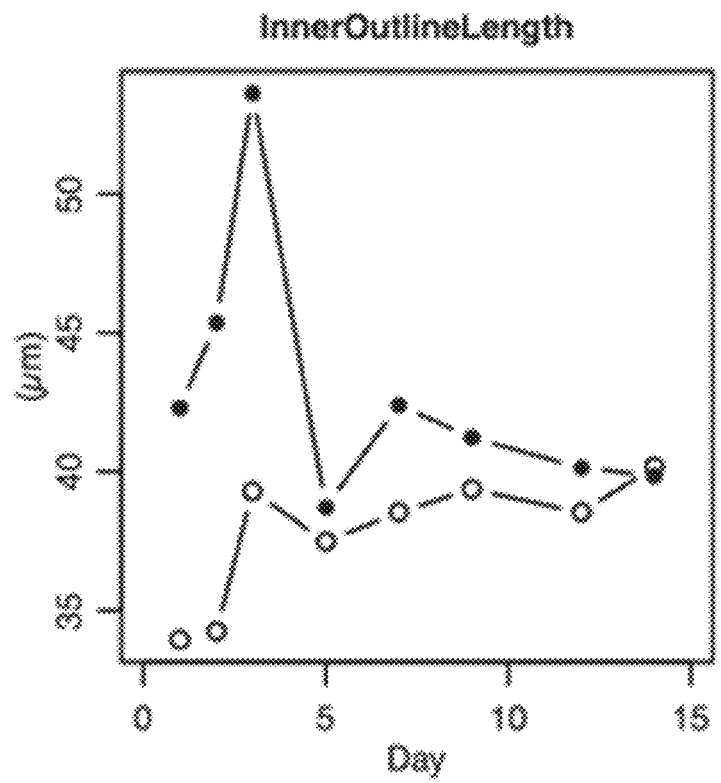
FIG. 36 is a graph showing the correlation between the culture time and InnerOutlineLength (unit: $\mu m$) indicating the outline length of a pigmented region in a cell of the cell image.

FIG. 36 is a graph showing the correlation between the culture time and InnerOutlineLength (unit: μm) indicating the outline length of a pigmented region in a cell in the cell image. In FIG. 36, the vertical axis indicates the measured value of InnerOutlineLength, and the horizontal axis indicates the number of days for which cells are cultured.

Figure 37:
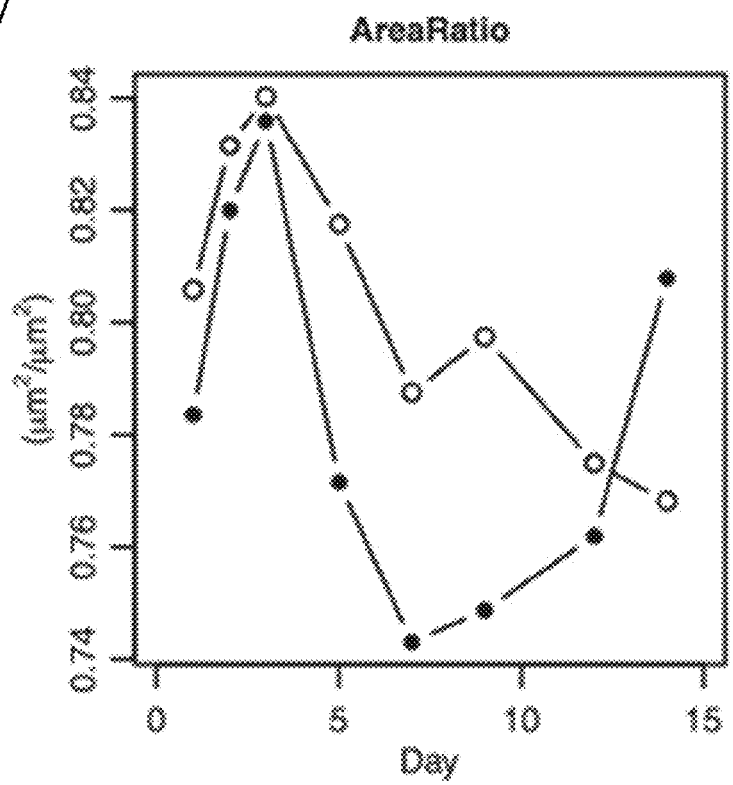
FIG. 37 is a graph showing the correlation between the culture time and AreaRatio (unit: $\mu m^2/\mu m^2$) indicating the ratio between the area of a pigmented region in a cell and the area of a cell in the cell image.

FIG. 37 is a graph showing the correlation between the culture time and AreaRatio (unit: $\mu m^2/\mu m^2$) indicating the ratio between the area of the pigmented region in a cell and the area of the cell in the cell image. In FIG. 37, the vertical axis indicates the measured value of AreaRatio, and the horizontal axis indicates the number of days for which cells are cultured. The cell structure calculating section 18 described above determines the ratio of the area of the pigmented region to the area of the entire cell image by dividing the area of the pigmented region by the area of the entire cell image, using the pixel values of the cell image, and the ratio is used as AreaRatio.

Figure 38:
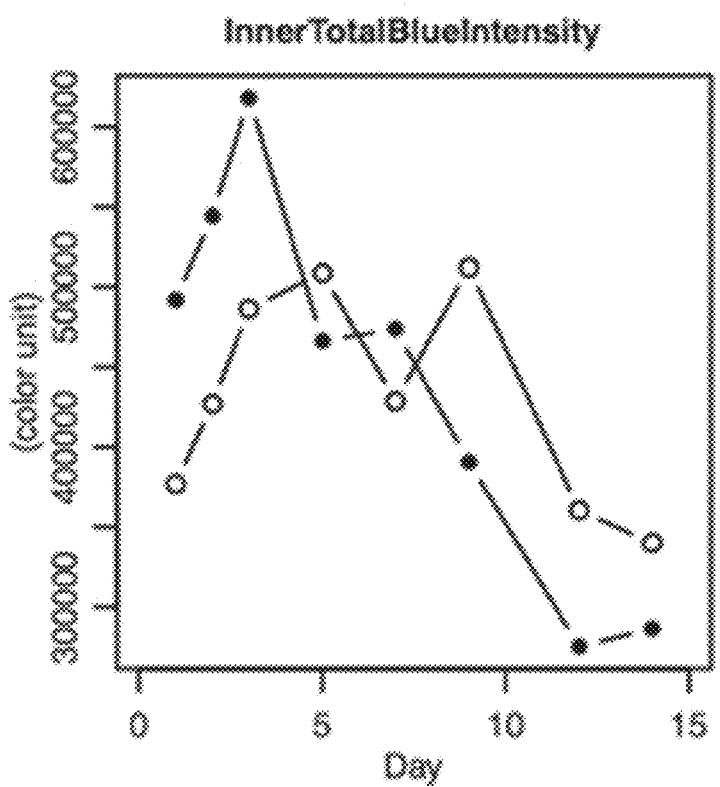
FIG. 38 is a graph showing the correlation between the culture time and InnerTotalBlueIntensity (unit: color unit) which is a numerical value indicating the sum of the intensity values of the blue channels (B pixels) of a pigmented region in a cell in the cell image of the cultured cell.

FIG. 38 is a graph showing the correlation between the culture time and InnerTotalBlueIntensity (unit: color unit) which is a numerical value indicating the sum of the intensity values of the blue channels (B pixels) of a pigmented region in a cell in the cell image of the cultured cell. In FIG. 38, the vertical axis indicates the measured value of InnerTotalBlueIntensity, and the horizontal axis indicates the number of days for which cells are cultured. Here, the cell structure calculating section 18 described above calculates the sum of the intensity values of B pixels in the entire pixels in a pigmented region in the cell image, and the summation result is used as InnerTotalBlueIntensity.

Figure 39:
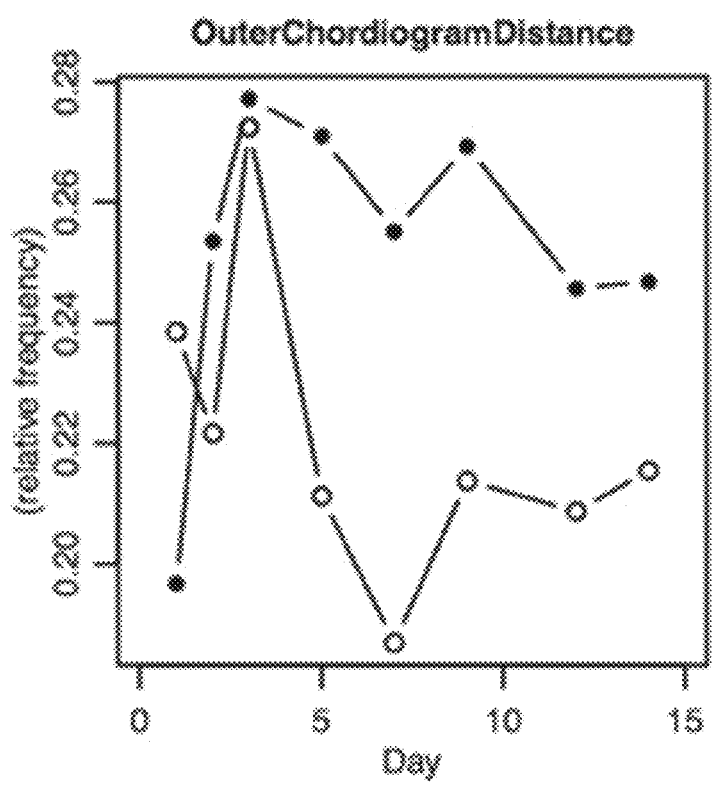
FIG. 39 is a graph showing the correlation between the culture time and OuterChordiogramDistance (unit: relative frequency) which is a numerical value indicating the Chordiogram distance (a parameter described above) in the cell image.

FIG. 39 is a graph showing the correlation between the culture time and OuterChordiogramDistance (unit: relative frequency) which is a numerical value indicating the Chordiogram distance (parameter described above) in the cell image. In FIG. 39, the vertical axis indicates the measured value of OuterChordiogramDistance, and the horizontal axis indicates the number of days for which cells are cultured.

Figure 40:
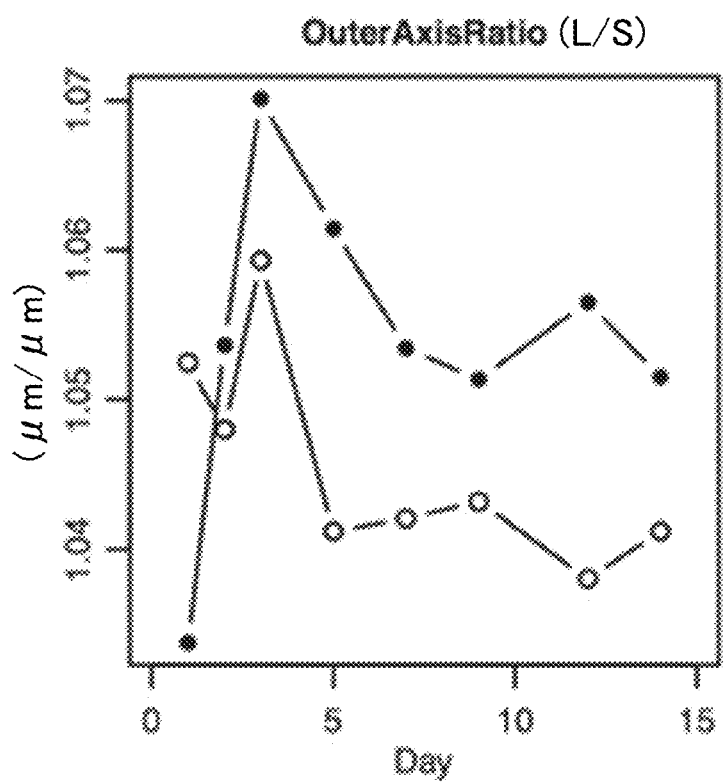
FIG. 40 is a graph showing the correlation between the culture time and OuterAxisRatio (L/S) (unit: $\mu m/\mu m$) which is a numerical value indicating the ratio of the long axis to the short axis in the cell image of the cultured cell.

FIG. 40 is a graph showing the correlation between the culture time and OuterAxisRatio (L/S) (unit: μm/μm) which is a numerical value indicating the ratio between the long axis and the short axis in the cell image of the cultured cell. In FIG. 40, the vertical axis indicates the measured value of OuterAxisRatio (L/S), and the horizontal axis indicates the number of days for which cells are cultured.

Figure 41:
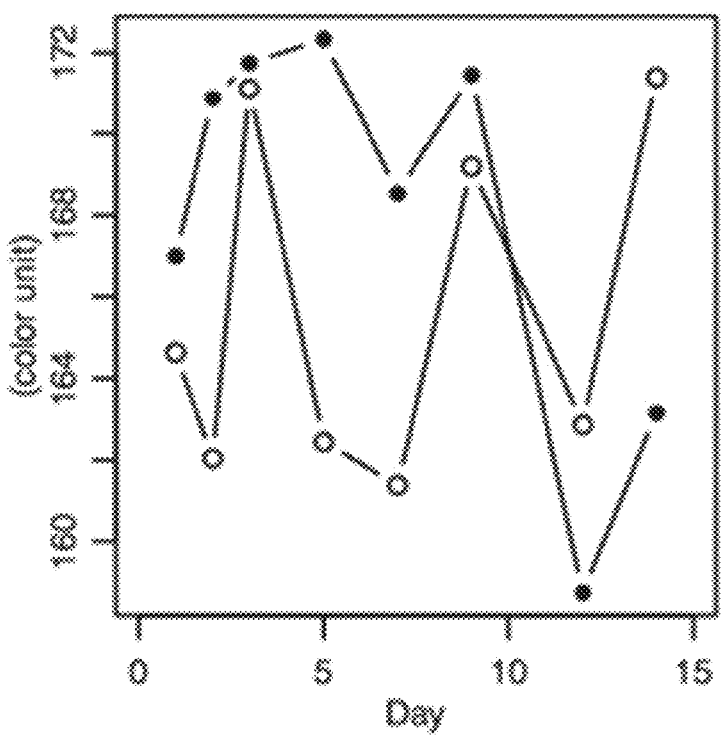
FIG. 41 is a graph showing the correlation between the culture time and OuterMeanRedIntensity (unit: color unit) which is a numerical value indicating the mean intensity value of the red channels (R pixels) in a cell in the cell image of the cultured cell.

FIG. 41 is a graph showing the correlation between the culture time and OuterMeanRedIntensity (unit: color unit) which is a numerical value indicating the mean intensity value of the red channels (R pixels) in a cell in the cell image of the cultured cell. In FIG. 41, the vertical axis indicates the measured value of OuterMeanRedIntensity, and the horizontal axis indicates the number of days for which cells are cultured. Here, the cell structure calculating section 18 described above calculates the mean intensity value of R pixels in the entire pixels in the cell image, and the calculation result is used as OuterMeanRedIntensity.

Figure 42:
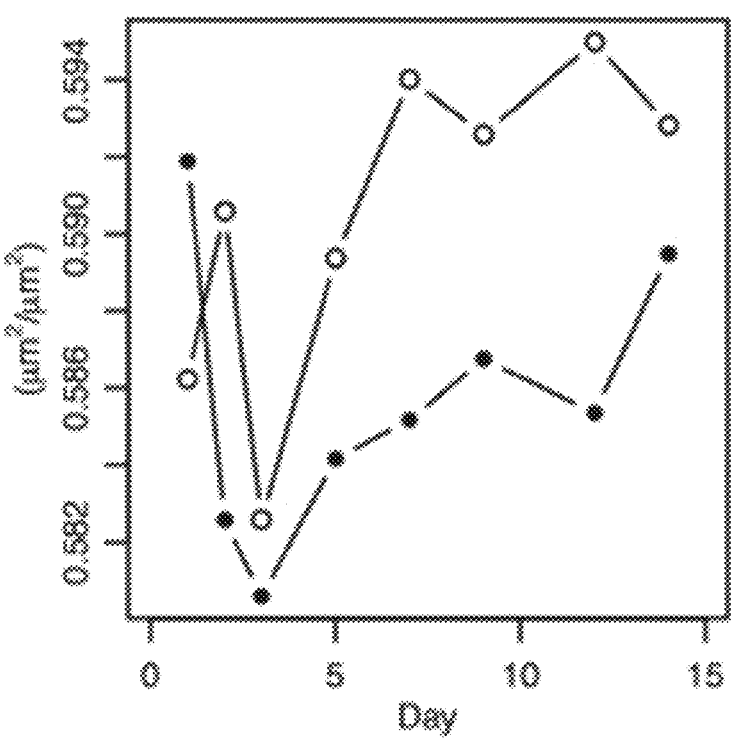
FIG. 42 is a graph showing the correlation between the culture time and OuterRoundFitness (unit: $\mu m^2/\mu m^2$) which is a numerical value indicating the fitness of the outer edge of the cell image to a circle.

FIG. 42 is a graph showing the correlation between the culture time and OuterRoundfitness (unit: μm²/μm²) which is a numerical value indicating the fitness of the outer edge of the cell image to a circle. In FIG. 42, the vertical axis indicates the measured value of OuterRoundfitness, and the horizontal axis indicates the number of days for which cells are cultured.

Figure 43:
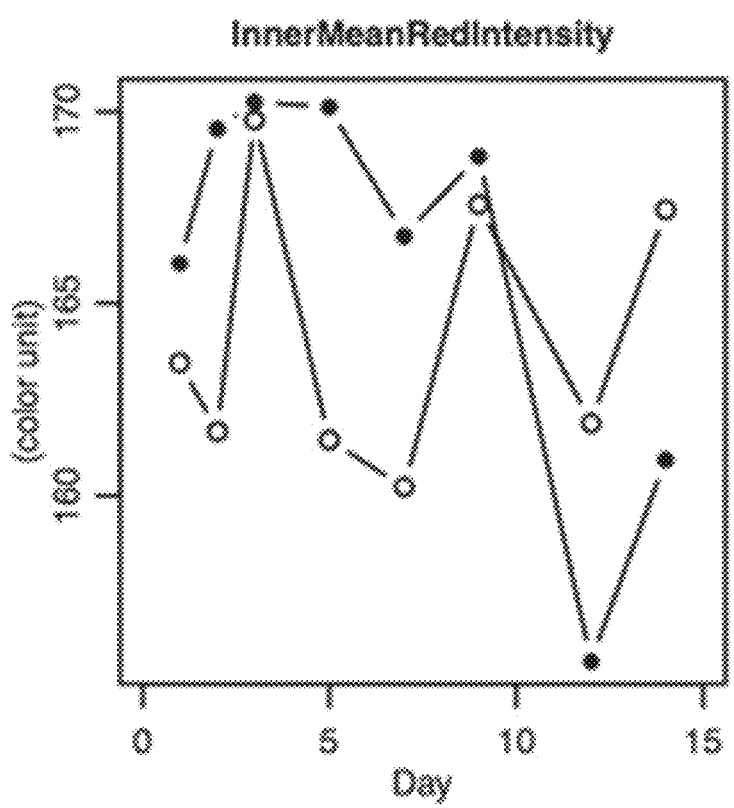
FIG. 43 is a graph showing the correlation between the culture time and InnerMeanRedIntensity (unit: color unit) which is a numerical value indicating the mean intensity value of the red channels (R pixels) in a pigmented region in a cell in the cell image of the cultured cell.

FIG. 43 is a graph showing the correlation between the culture time and InnerMeanRedIntensity (unit: color unit) which is a numerical value indicating the mean intensity value of the red channels (R pixels) in a pigmented region in a cell in the cell image of the cultured cell. In FIG. 43, the vertical axis indicates the measured value of InnerMeanRedIntensity, and the horizontal axis indicates the number of days for which cells are cultured. Here, the cell structure calculating section 18 described above calculates the mean intensity value of R pixels in the entire pixels in the pigmented region in the cell image, and the calculation result is used as InnerMeanRedIntensity.

Figure 44:
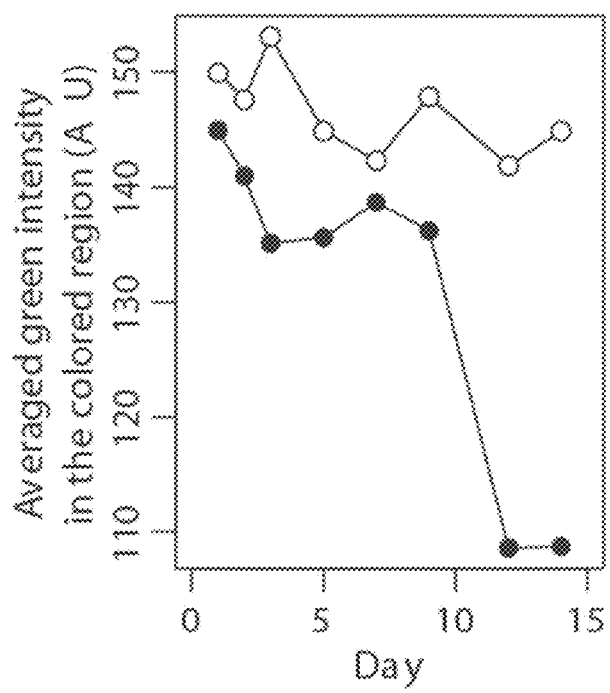
FIG. 44 is a graph showing the correlation between the culture time and InnerMeanGreenIntensity (unit: color unit) which is a numerical value indicating the mean intensity value of the green channels (G pixels) in a pigmented region in a cell in the cell image of the cultured cell.

FIG. 44 is a graph showing the correlation between the culture time and InnerMeanGreenIntensity (unit: color unit) which is a numerical value indicating the mean intensity value of the green channels (G pixels) in a pigmented region in a cell in the cell image of the cultured cell. In FIG. 44, the vertical axis indicates the measured value of InnerMeanGreenIntensity, and the horizontal axis indicates the number of days for which cells are cultured. Here, the cell structure calculating section 18 described above calculates the mean intensity value of G pixels in the entire pixels in the pigmented region in the cell image, and the calculation result is used as InnerMeanGreenIntensity.

Figure 45:
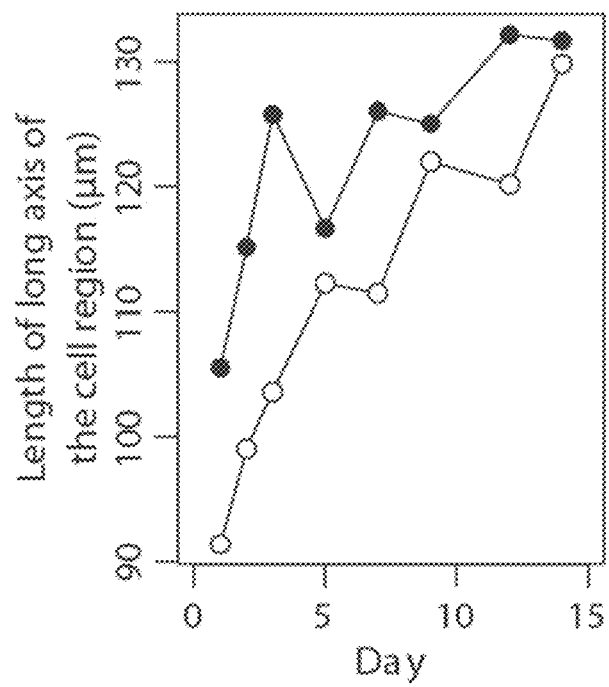
FIG. 45 is a graph showing the correlation between the culture time and OuterLongAxisLength (unit: $\mu m$) indicating the size of the maximum width (long axis) portion in the cell image of the cultured cell.

FIG. 45 is a graph showing the correlation between the culture time and OuterLongAxisLength (unit: μm) indicating the length of the maximum width (long axis) portion in the cell image of the cultured cell. In FIG. 24, the vertical axis indicates the measured value of OuterLongAxisLength, and the horizontal axis indicates the number of days for which cells are cultured.

To generate the tree model in the random forest method described above, twenty five parameters shown in FIGS. 21 to 45 were used.

<Evaluation of Dynamism in Change of Development Over Time of Monitoring Target Cell (*Haematococcus*)>

Next, from the parameters determined by the cell morphology detecting section 19 including twenty five parameters of FIGS. 21 to 45, suitable parameters were chosen by a principal component analysis for the purpose of evaluating the change over time and the condition dependence in the *Haematococcus* cell morphology development process from zoospore to palmelloid.

By this principal component analysis, the contribution ratio of the first principal component PC1 was determined to be 51%. It was found that the first principal component PC1 had a high correlation with eight parameters (described below) including the length of the long axis, i.e., the OuterLongAxisLength, and the area of the cell, i.e., the OuterArea, among the parameters detected by the cell structure calculating section 18 including twenty five parameters of FIGS. 21 to 45 described above.

Among those eight parameters, for example, the outline length of a cell shown in FIG. 21, i.e., OuterOutlineLength, the maximum width, i.e., OuterMaxRadius, from the gravity center to the outer edge of the cell image shown in FIG. 22, show a linear change with respect to the time change, and have a high correlation with the first principal component PC1.

Figure 46:
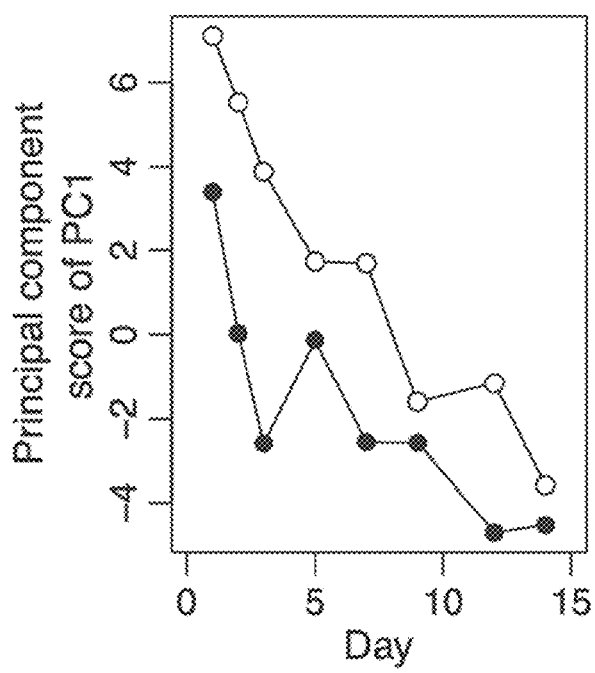
FIG. 46 is a graph showing the correlation between a first principal component PC1 and an elapsed time from the start of culturing.

Next, FIG. 46 is a graph showing the correlation between the first principal component PC1 and an elapsed time from the start of culturing. In FIG. 46, the vertical axis indicates the score of the first principal component PC1, and the horizontal axis indicates the elapsed time (Day) from the start of the culturing.

As can be seen from FIG. 46, although the value of the first principal component decreases with time, the manner of changes is different for the LL condition and the LD condition. However, both of the cells cultured under either the LL condition or the LD condition are correlated with the first principal component PC1, and naturally, have a correlation with respect to the time change. Therefore, it is found that for both of the LL condition and the LD condition, the parameter correlated with the first principal component PC1 can be used as the parameter for detecting the morphological changes in the developmental process in the time course of the monitoring target cell.

Figure 47:
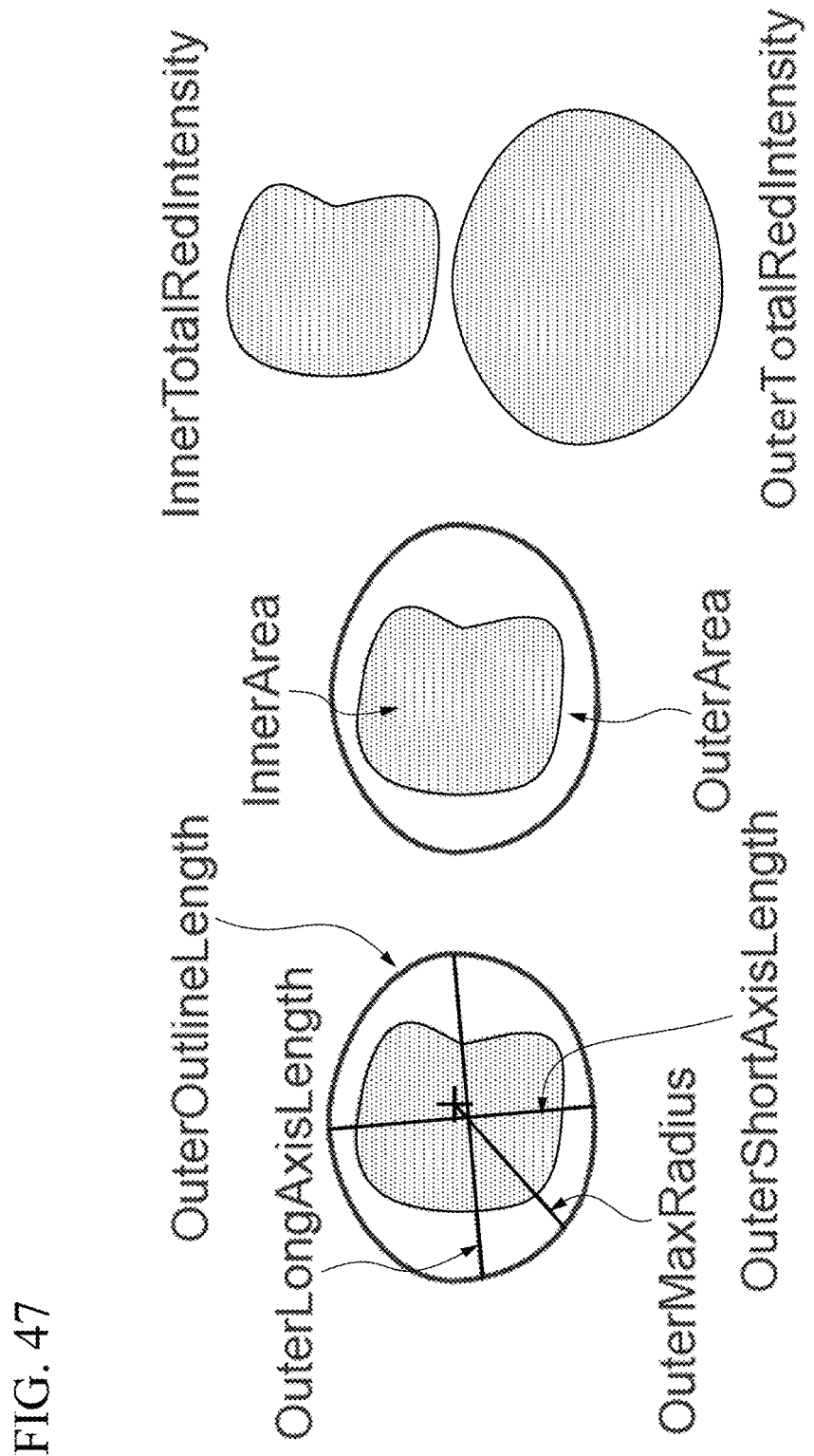
FIG. 47 is a diagram showing eight parameters having a correlation with the first principal component PC1 (i.e., having a correlation with the shape depending on the time course).

Next, FIG. 47 is a diagram showing eight parameters correlated with the first principal component PC1 (i.e., correlated with the time course in the morphological changes). The eight parameters are: the length of the long axis, i.e., OuterLongAxisLength (FIG. 45); the outline length of a cell, i.e., the OuterOutlineLength (FIG. 21); the maximum width from the gravity center to the outer periphery, i.e., the OuterMaxRadius (FIG. 22); the area of a cell, i.e., OuterArea (FIG. 23); the length of the short axis, i.e., the OuterShortAxisLength (FIG. 24); the sum of the intensity values of the entire red channels in the cell image, i.e., the OuterTotalRedIntensity (FIG. 25); the area size of pigmented portion (pigmented region) in a cell, i.e., the InnerArea (FIG. 26); and the sum of the intensity values of the red channels in a pigment portion, i.e., the InnerTotalRedIntensity (FIG. 27).

Therefore, when monitoring the morphology in the development process in the change of a cell over time, by monitoring each of the above-described eight parameters, i.e., the OuterLongAxisLength, the OuterOutlineLength, the OuterMaxRadius, the OuterArea, the OuterShortAxisLength, the OuterTotalRedIntensity, the InnerArea, and the InnerTotalRedIntensity through the lapse of time, it is possible to detect the morphological change of a cell using the cell image. Therefore, when culturing cells, by monitoring the eight parameters described above, statistically, it is possible to determine that the cells is in which stage of the development process (degree of the numerical value of the first principal component PC1) at different lapse of time, and it is possible to determine whether the culture environment is suitable or unsuitable.

Figure 48:
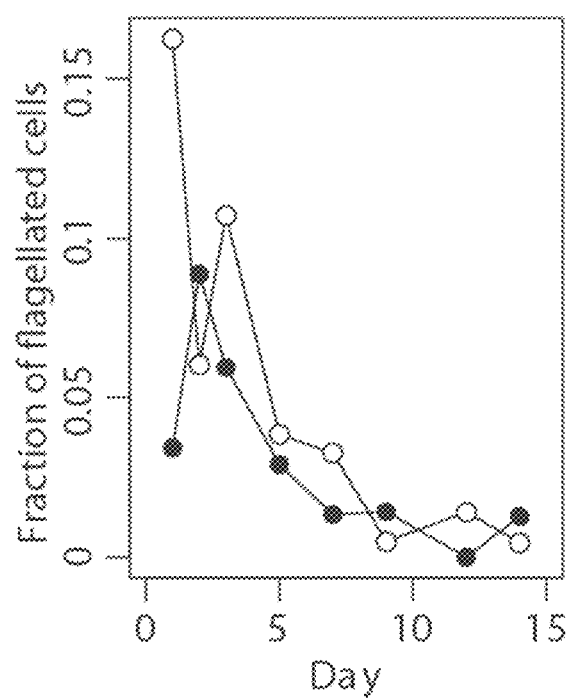
FIG. 48 is a graph the correlation between generation and disappearance of flagella and an elapsed time from the start of culturing.

Next, FIG. 48 is a graph showing the correlation between generation and disappearance of flagella and the elapsed time from the start of culturing. In FIG. 48, the vertical axis indicates the appearance rate (fraction of flagellated cells) which is the frequency of appearance of flagellated cells, and the horizontal axis indicates the elapsed time (Day) from the start of culture. From FIG. 48, it is found that, for cells in the LL condition culture environment, the peak of flagella generation in cells is at the first day, and for cells in the LD condition culture environment, the peak of generation of flagella in cells is at the second day. The appearance rate is obtained by dividing the number of cells having flagella by total cells in the measurement region of the culture medium in which cells are cultured.

In addition, it is found that, with respect to the temporal change in the loss of flagella in the time course thereafter, there is no difference between the cells in the culture environments of the LL condition and the LD condition. From this parameter, it is found that the development rate from the start of the culture until flagella generation in culture is faster in the LL condition culture environment than in the LD condition culture environment. However, it is found that for the development process after flagella are generated, from zoospore to palmelloid, there is no difference between cultures under the environments of the LL condition and the LD condition.

For example, changes in the mean intensity value of the green channels in a cell shown in FIG. 33, i.e., the OuterMeanGreenIntensity are different, for the period after the tenth day from the start of the cell culture. That is, in the culture under the environment of the LL condition, the numerical value of the OuterMeanGreenIntensity in the cell image obtained by capturing cells does not change.

On the other hand, in the culture under the environment of the LD condition, a significant decrease can be seen in the numerical value of OuterMeanGreenIntensity in the cell image obtained by capturing cells. From this result, it is found that OuterMeanGreenIntensity is a parameter by which the cells cultured under the environment of the LD condition from the cells cultured under the LL condition can be distinguished.

It is inferred that for the parameters having low correlation with the first principal component PC1, the temporal difference in the cell morphology during the development process depends not on the change by the lapse of time in the cell morphology development, but rather on the culture conditions and the environment.

Therefore, by choosing parameters dependent on the culture conditions and environments among the parameters having low correlation with the first principal component PC1, as described above, it is possible to perform clustering of cells grown under either of the LL condition and the LD condition.

As described above, from parameters determined by the cell monitoring device according to the embodiment, it is possible to determine parameters characterized by monitoring-cell temporal change and parameters characterized by condition-dependent and environment-dependent change, using a principal component analysis.

In addition, by the parameter extracted using the principal component analysis, it is possible to evaluate the dynamism of temporal changes in the growth of the monitoring target cells.

<Discrimination Analysis of Different Strain of Chlorella Cell>

Then, using the discrimination analysis method, discrimination analysis of different strains of chlorella cells was performed. For example, in the embodiment, discrimination analyses were performed on the wild-type (WT) chlorella strain, a mutant strain PkE6 derived from the wild-type strain, and a mutant strain PkE8. Discrimination analysis is a technique, under a condition where each of the data given in advance can be clearly classified into one of different groups, to obtain a criteria (discrimination function) for discriminating (clustering) to which group a new data is clustered. The following process is performed using the data of the parameters shown in FIGS. 21 to 45 using the cell morphology detecting section 19.

Figure 49:
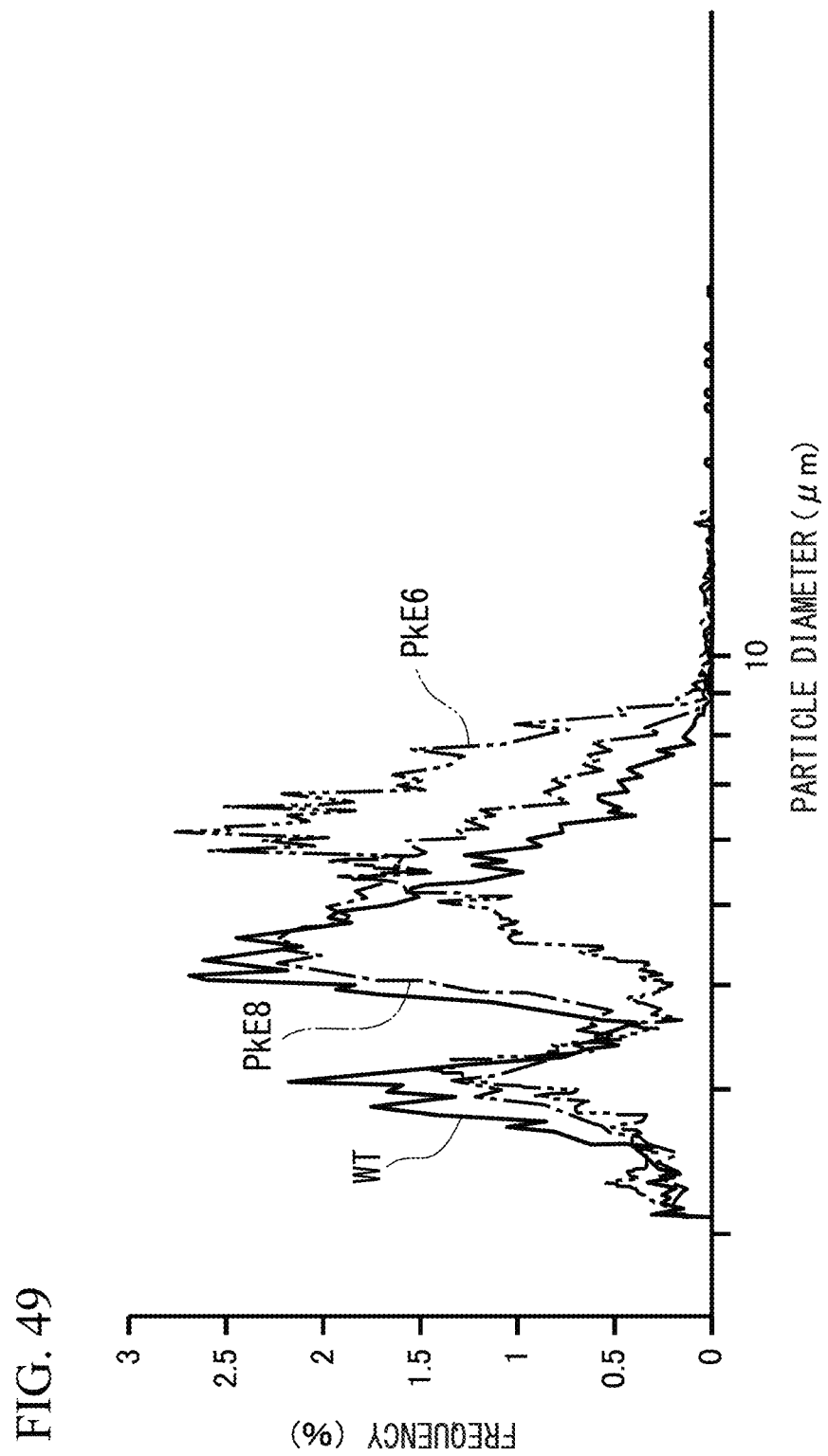
FIG. 49 is a graph showing the appearance frequency of each particle diameter of a wild-type (WT) strain, a mutant strain PkE6, and a mutant strain PkE8 detected using an automatic cell counting device.

FIG. 49 is a graph showing the appearance frequency, which is the frequency at which each of the particle diameters observed, for each of the wild-type (WT) strain, the mutant strain PkE6, and the mutant strain PkE8. This frequency is detected using an automatic cell counting device which can measure the particle diameter and the number of particles at the same time. In FIG. 49, the vertical axis indicates the appearance frequency, and the horizontal axis indicates the particle diameter of a cell. The particle diameter corresponds to the parameter OuterLongAxisLength in the embodiment. As can be seen from FIG. 49, it was found that the particle diameter of the mutant strain PkE6 is large, by the measurement using the automatic cell counting device. Here, WT is an abbreviation of wild-type.

Figure 50:
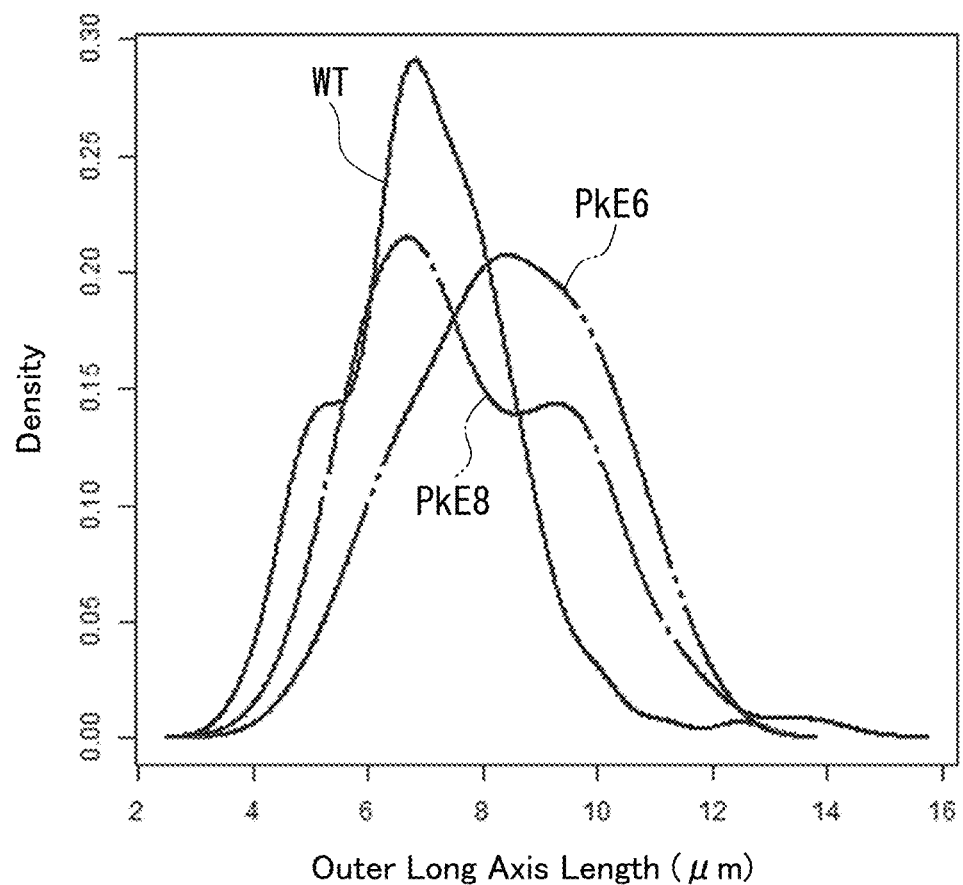
FIG. 50 is a graph showing the appearance frequency of each particle diameter of a wild-type (WT) strain, a mutant strain PkE6, and a mutant strain PkE8, obtained using a cell monitoring device 1 according to the embodiment.

Next, FIG. 50 is a graph showing the appearance frequency of particle diameters for each of the wild-type (WT) strain, the mutant strain PkE6, and the mutant strain PkE8, obtained by the cell morphology detecting section 19 in the cell monitoring device 1 according to the embodiment. In FIG. 50, the vertical axis indicates the appearance frequency, and the horizontal axis indicates the parameter OuterLongAxisLength (particle diameter) detected from the cell image. In FIG. 50, the wild-type (WT) strain is indicated by a solid line, the mutant strain PkE8 is indicated by a dashed line, and the mutant strain PkE6 is indicated by a dot and dash line. The appearance frequency is obtained by dividing the sum of probability densities having respective particle diameters by the value for all cells in the measurement region of the culture medium in which cells are cultured. Here, the probability density for a cell to have respective particle diameters is estimated by the kernel density estimation method in which it is assumed that the particle diameters of respective cells obtained are distributed according to a normal distribution.

As can be seen from FIG. 50, it was confirmed that the particle diameter of the mutant strain PkE6 is large, also by the image analysis for each of cell images in the captured image by the cell monitoring device 1 according to the embodiment.

Here, the cell morphology detecting section 19 detects the particle diameter of the cell image in a predetermined region in the captured image, and determines the appearance frequency of cells having this particle diameter, for each of the particle diameters. FIG. 50 is the graph showing the result.

From this result, it is found that the mutant strain PkE6 has the largest particle diameters, the mutant strain PkE8 has the next largest particle diameters, and the wild-type (WT) strain has the smallest particle diameters. In addition, from FIG. 50, it is found that populations of cells having the similar size with the mutant strain PkE6 is also present in the mutant strain PkE8.

FIG. 51 is a table showing the significance test results for the parameters shown in FIGS. 21 to 45. In the table in FIG. 51, ID indicates the parameter name, kw indicates the test result of the Kruskal-Wallis test, e6/wt indicates the result of pairwise U-test comparison between the mutant strain PkE6 and the wild-type strain (WT), e8/wt indicates the result of pairwise U-test comparison between the mutant strain PkE8 and the wild-type strain (WT), and e6/e8 indicates the result of pairwise U-test comparison between the mutant strain PkE6 and the mutant strain PkE8. In the test results of the Kruskal-Wallis test, significant differences were detected in twenty parameters among the twenty five parameters (P<0.05, P-value determination). In the U-test, significant differences are detected in thirty two pairs among of 75 pairs (P<0.05, P-value determination).

From the results described above, it is expected that it is possible to identify each of the wild-type (WT) strain, the mutant strain PkE6, and the mutant strain PkE8 by performing the discrimination analysis using the parameters shown in FIG. 51.

Figure 52:
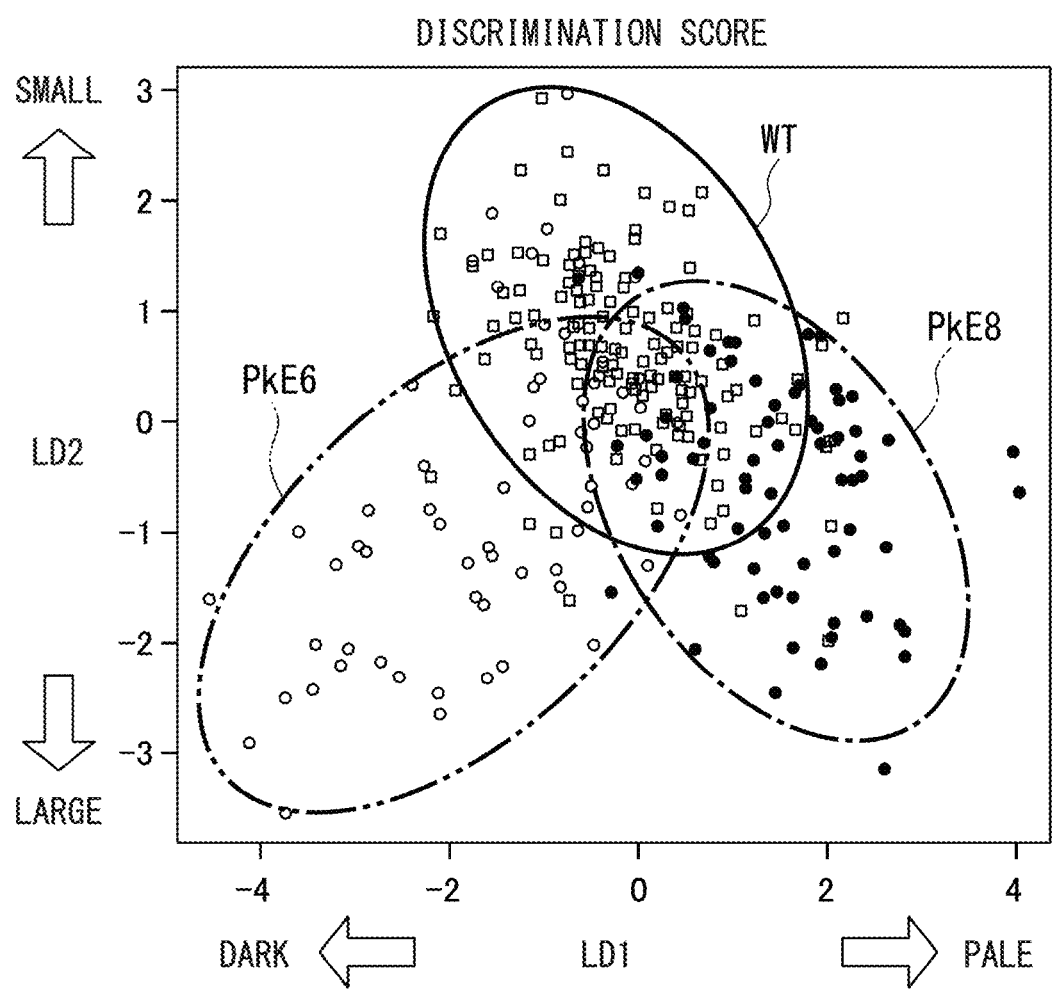
FIG. 52 is a graph showing each classification result of a wild-type (WT) strain, a mutant strain PkE8, and a mutant strain PkE6 by classification functions LD1 and LD2 obtained from classification analyses.

FIG. 52 is a graph showing each discrimination result for the wild-type (WT) strain, the mutant strain PkE6, and the mutant strain PkE8 by discrimination functions LD1 and LD2 obtained from discrimination analyses. In FIG. 52, the vertical axis indicates the score of the discrimination functions LD2, and the horizontal axis indicates the score of the discrimination functions LD1. In addition, In FIG. 52, the white circle indicates the mutant strain PkE6, the black circle indicates the mutant strain PkE8, and the white square indicates the wild-type (WT) strain. In this result, there is a tendency that as the score of the discrimination functions LD1 increases to the +side, the color of the pigment in a cell becomes thinner, and, in contrast, as the score of the discrimination functions LD1 increases in absolute value to the –side, the color of the pigment in a cell becomes darker. In addition, there is a tendency that as the score of the discrimination functions LD2 increases to the +side, the size of a cell becomes smaller, and, in contrast, as the score of the discrimination functions LD2 is increases in absolute value to the –side, the size of a cell becomes larger.

As described above, the discrimination function LD1 has a high correlation with the parameters showing the intensity of the channel of each color in the pixels in the cell or in the pigmented region of the cell image. On the other hand, the discrimination function LD2 has a high correlation with the parameters showing the size of the cell of the cell image.

Thus, from FIG. 52, it is found that the wild-type (WT) strain, the mutant strain PkE6, and the mutant strain PkE8 are separated (clustered) as distinctive groups.

FIG. 53 is a table showing correlation coefficients between each of the discrimination functions LD1 and LD2 and the parameters shown in FIGS. 21 to 45. In the table in FIG. 53, ID indicates the parameter name, LD1 indicates a correlation coefficient with the discrimination function LD1, and LD2 indicates a correlation coefficient with the discrimination function LD2. From the table in FIG. 53, it is found that the discrimination function LD1 has a high correlation with a parameter showing the intensity value of the channel of each color in the pixels in the cell or the pigmented region of the cell image. On the other hand, it is found that the discrimination function LD2 has a high correlation with the parameters showing the size of the cell in the cell image.

Figure 54:
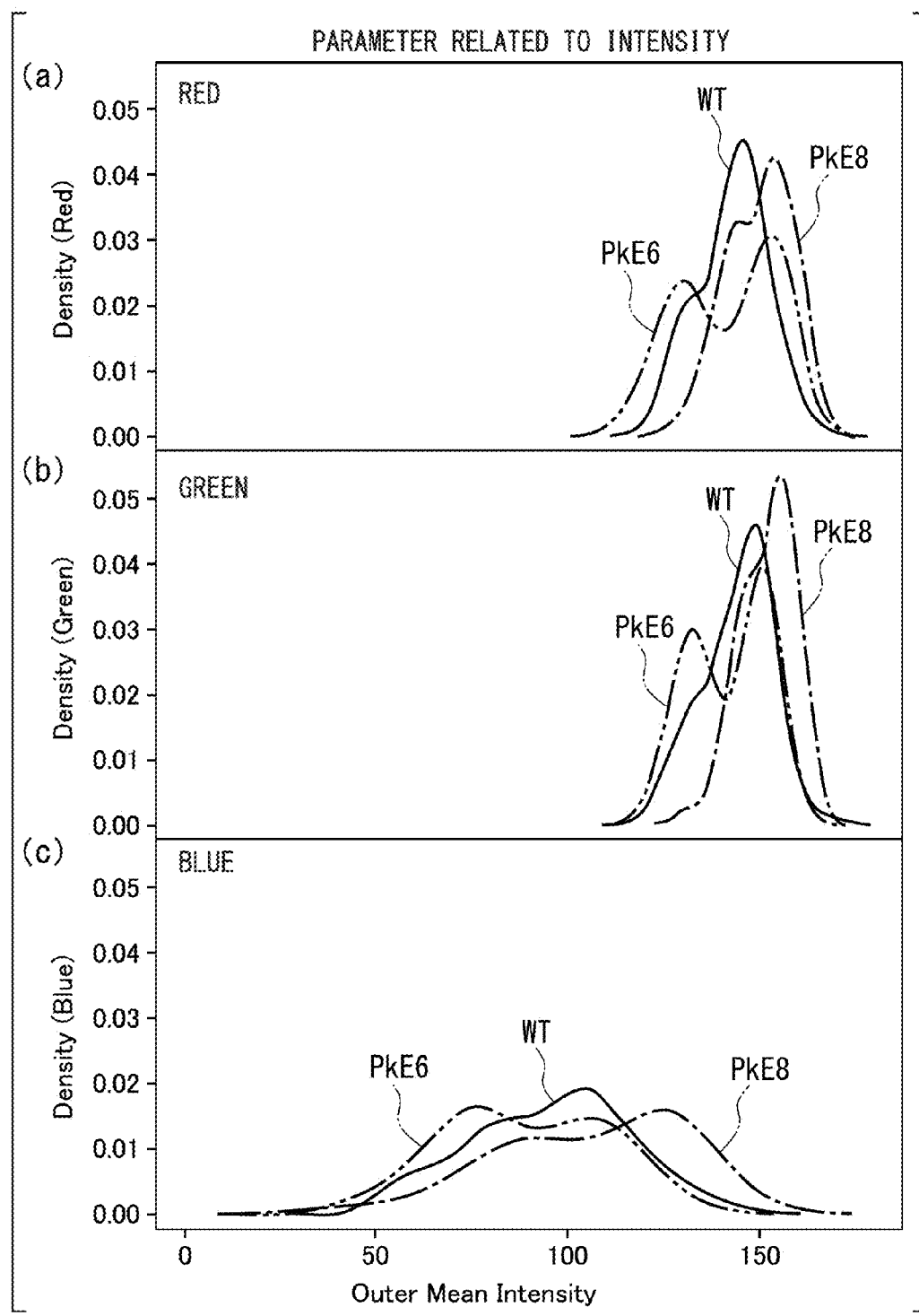
FIG. 54 is a graph the correlation between a mean intensity value (OuterMeanIntensity) of pixels of cells of each color channel highly correlated with the classification function LD1 and an appearance rate.

FIG. 54 is a graph showing the correlation between the mean intensity value (OuterMeanIntensity) of pixels of cells of each color channel, which have a high correlation with the discrimination function LD1, and the appearance rate of cells.

FIG. 54(a) shows the correlation between the mean intensity value of the red channels in the pixels of a cell and the appearance rate of the cells having the mean value. In FIG. 54(a), the vertical axis indicates the appearance rate of cells, and the horizontal axis indicates the numerical value of the parameter OuterMeanRedIntensity. For OuterMeanRedIntensity, the mean intensity value of the mutant strain PkE8 is the highest compared to those for the wild-type (WT) strain and for the mutant strain PkE6. In the mean intensity values of the mutant strain PkE6, two peaks are observed, one population having the same value as that of the mutant strain PkE8 and the other population having a lower value than those of the wild-type (WT) strain and the mutant strain PkE8. The mean intensity value of the wild-type (WT) strain is lower than that of the mutant strain PkE8, and higher than that of population having a low intensity value of the mutant strain PkE6.

FIG. 54(b) shows the correlation between the mean intensity value of the green channels in the pixels of a cell and the appearance rate of the cells having the mean value. In FIG. 54(b), the vertical axis indicates the appearance rate of cells, and the horizontal axis indicates the numerical value of the parameter OuterMeanGreenIntensity. For OuterMeanGreenIntensity, in the same manner as in OuterMeanRedIntensity, the mean intensity value of the mutant strain PkE8 is the highest as compared to those of the wild-type (WT) strain and the mutant strain PkE6. In the mean intensity values of the mutant strain PkE6, two peaks of population are observed, each having the same value as that of the mutant strain PkE8 and having a lower value than those of the wild-type (WT) strain and the mutant strain PkE8. The mean intensity values of the wild-type (WT) strain is lower than that of the mutant strain PkE8, and higher than that of population having a low intensity value of the mutant strain PkE6.

FIG. 54(c) shows the correlation between the mean intensity value of the blue channels in the pixels of a cell and the appearance rate of the cells having the mean value. In FIG. 54(c), the vertical axis indicates the appearance rate of cells, and the horizontal axis indicates the numerical value of the parameter OuterMeanBlueIntensity. For OuterMeanBlueIntensity, in the same manner as in OuterMeanRedIntensity, the mean intensity values of the mutant strain PkE8 is the highest as compared to those of the wild-type (WT) strain and the mutant strain PkE6. The mean intensity values of the mutant strain PkE6 is the lowest as compared to those of the mutant strain PkE8 and the wild-type (WT) strain. The mean intensity values of the wild-type (WT) strain is lower than that of the mutant strain PkE8, and higher than that of the mutant strain PkE6.

In the process described above, the cell morphology detecting section 19 estimates the probability density that each cell appears in each numerical value of the parameter OuterMeanRedIntensity in each stain among the wild-type (WT) strain, the mutant strain PkE6, and the mutant strain PkE8. Then the appearance rate is calculated by dividing the sum of the estimated probability densities by the number of cells of all strains. In the same manner, the cell morphology detecting section 19 estimates the probability density that each cell appears in each numerical value of the parameter OuterMeanGreenIntensity in each stain among the wild-type (WT) strain, the mutant strain PkE6, and the mutant strain PkE8. Then the appearance rate is calculated by dividing the sum of the estimated probability densities by the number of cells of all strains. In addition, the cell morphology detecting section 19 estimates the probability density for cells having each numerical value of the parameter OuterMeanBlueIntensity for each strain among the wild-type (WT) strain, the mutant strain PkE6, and the mutant strain PkE8. Then the appearance rate is calculated by dividing the sum of the estimated probability densities by the number of cells of all strains. Here, the estimation of the probability density for cells having respective particle diameters is performed by the kernel density estimation method.

Figure 55:
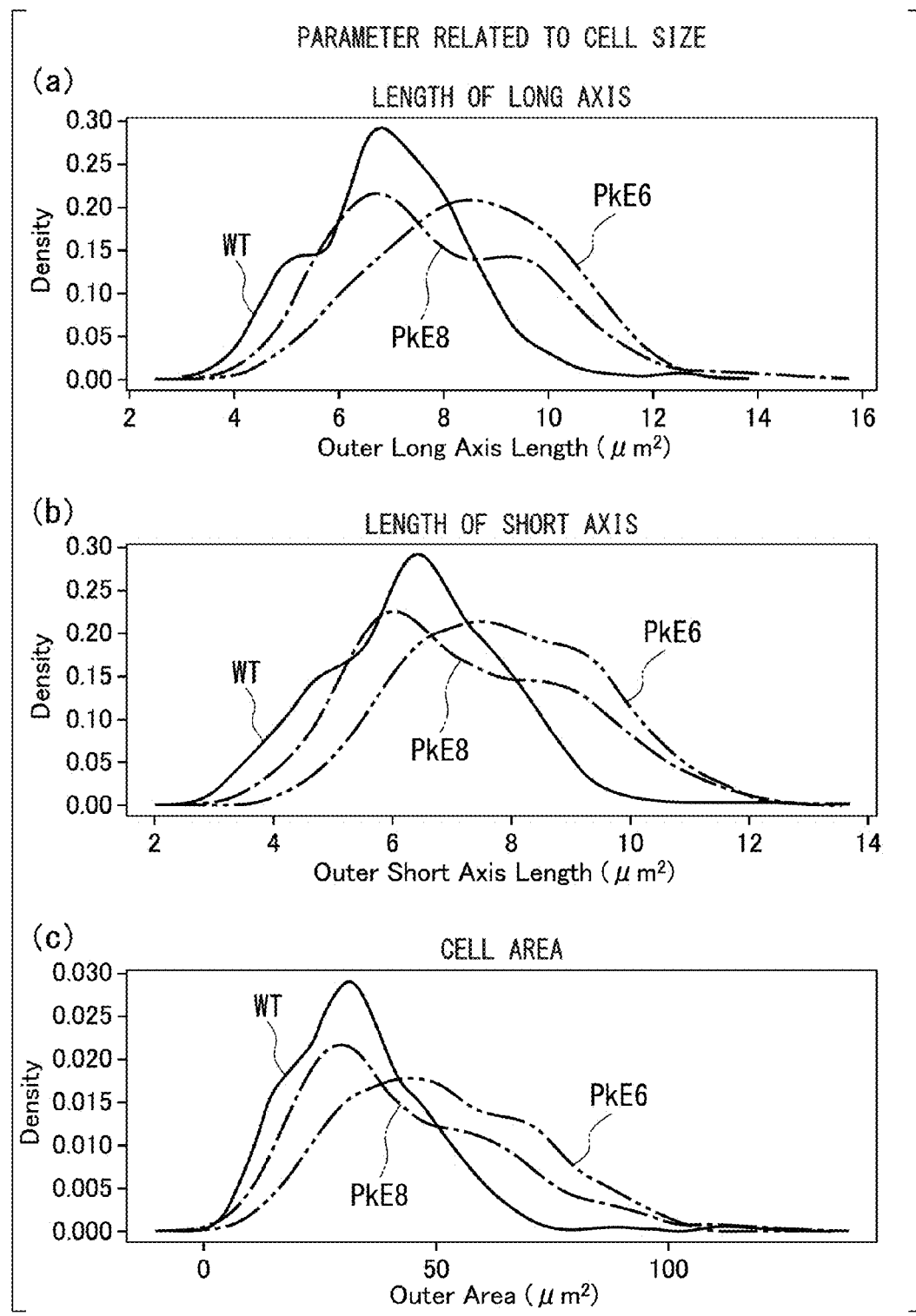
FIG. 55 is a graph the correlation between a parameter relating to the size of cells highly correlated with the classification function LD2 and an appearance rate.

FIG. 55 is a graph showing the correlation between the parameter relating to the cells size, which is highly correlated with the discrimination function LD2, and the appearance rate of cells. FIG. 55(a) shows the correlation between the length of the long axis, i.e., OuterLongAxisLength, and the appearance rate of cells having the long axis length, i.e., OuterLongAxisLength. In FIG. 55(a), the vertical axis indicates the appearance rate of cells, and the horizontal axis indicates the numerical value of the length of the long axis, i.e., OuterLongAxisLength. For the length of the long axis, i.e., OuterLongAxisLength, the peak of the mutant strain PkE6 is the highest as compared to the peak of the wild-type (WT) strain and the peak of the mutant strain PkE8. The peak of the wild-type (WT) strain is the smallest as compared to the peak of the mutant strain PkE6 and the peak of the mutant strain PkE8. The peak level of the mutant strain PkE8 is between the peak of the wild-type (WT) and the peak of the mutant strain PkE8.

FIG. 55(b) shows the correlation between the length of the short axis, i.e., OuterShortAxisLength and the appearance rate of cells having the short axis length, i.e., OuterShortAxisLength. In FIG. 55(b), the vertical axis indicates the appearance rate of cells, and the horizontal axis indicates the numerical value of the length of the short axis, i.e., OuterShortAxisLength. For the length of the short axis, i.e., OuterShortAxisLength, the peak of the mutant strain PkE6 is the highest as compared to the peak of the wild-type (WT) strain and the peak of the mutant strain PkE8. The peak of the mutant strain PkE8 is the smallest as compared to the peak of the wild-type (WT) strain and the peak of the mutant strain PkE8. The peak level of the wild-type (WT) strain is between the peak of the mutant strain PkE6 and the peak of the mutant strain PkE8.

FIG. 55(c) shows the correlation between the cell area size, i.e., the OuterArea and the appearance rate of cells having the cell area size, i.e., the OuterArea. In FIG. 55(c), the vertical axis indicates the appearance rate of cells, and the horizontal axis indicates the numerical value of the cell area size, i.e., the OuterArea. For the cell area size, i.e., the OuterArea, the peak of the mutant strain PkE6 is the highest as compared to the peak of the wild-type (WT) strain and the peak of the mutant strain PkE8. The peak of the mutant strain PkE8 is the smallest as compared to the peak of the wild-type (WT) strain and the peak of the mutant strain PkE8. The peak level of the wild-type (WT) strain is between the peak of the mutant strain PkE6 and the peak of the mutant strain PkE8.

In the process described above, the cell morphology detecting section 19 estimates the probability density that each cell appears in each numerical value of the parameter OuterLongAxisLength for each strain among the wild-type (WT) strain, the mutant strain PkE6, and the mutant strain PkE8. Then the appearance rate is calculated by dividing the sum of the estimated probability density by the number of cells of all strains. In the same manner, the cell morphology detecting section 19 estimates the probability density that each cell appears in each numerical value of the parameter OuterShortAxisLength for each strain among the wild-type (WT) strain, the mutant strain PkE6, and the mutant strain PkE8. Then the appearance rate is calculated by dividing the sum of the estimated probability density by the number of cells of all strains. In addition, the cell morphology detecting section 19 estimates the probability density that each cell appears in each numerical value of the parameter OuterArea for each strain among the wild-type (WT) strain, the mutant strain PkE6, and the mutant strain PkE8. Then the appearance rate is calculated by dividing the sum of the estimated probability density by the number of cells of all strains. Here, the estimation of the probability density for cells to have respective particle diameters is performed by the kernel density estimation method.

As described above, according to the embodiment, using the discrimination function LD1 correlated with the parameter related to the intensity value in the cell and the discrimination function LD2 correlated with the parameter related to the cell size, it is possible to classify cells into groups of each of the wild-type (WT) strain, the mutant strain PkE6, and the mutant strain PkE8.

In addition, detection of the physiological state of cells and management of culturing may be performed by recording the program for realizing the functions of the cell monitoring device 1 in FIG. 1 on a computer-readable recording medium, by causing a computer system to read the program recorded on the recording medium, and by executing the program. Moreover, the "computer system" described here includes OS or hardware such as peripheral devices.

In addition, when the WWW system is used in the "computer system", the system also includes a web pages providing environment (or display environment).

In addition, the "computer-readable recording medium" refers to portable media such as a flexible disk, a magneto-optical disk, ROM, and CD-ROM, and storage devices such as a hard disk built in a computer system. Furthermore, the "computer-readable recording medium" also includes a medium dynamically retaining a program for a short period of time, as in communication lines for sending programs through communication channels such as networks like the internet or communication lines like the telephone line, and a medium retaining a program for a certain period of time, such as volatile memory inside a computer system which becomes a server or a client for the communication. In addition, the program may realize a part of the functions described above, and, furthermore, the program may realize the functions described above in combination with programs already recorded in the computer system.

The embodiments of the invention has been described in detail with reference to the accompanying drawings, but specific configurations are not limited to the embodiment, and the invention includes design differences not departing from the gist of the invention.

INDUSTRIAL APPLICABILITY

It is possible to provide a cell monitoring device for monitoring in real time the contamination status of other organisms contaminated in a culture medium of cells and the production amount of useful substances by microalgae cells, in development of culture conditions or breeding strains producing high amount of the useful substance, in order to improve the production amount of the useful substances by the cells.

REFERENCE SIGNS LIST

1 Cell monitoring device
11 Controller
12 Color modifying section
13 Outline detecting section
14 Pigmented region detecting section
15 Image segmentation section
16 Image merging section
17 Cell region detecting section
18 Cell structure detecting section
19 Cell morphology detecting section
20 Pigment value calculating section
21 Image storage section
22 Storage section
23 Table storage section
24 Display

The invention claimed is:

1. A cell monitoring device, comprising:
an outline detecting section that detects edge pixels from a cell image in a captured image of cells arranged in a single layer and generates an edge image including the detected edge pixels;
a pigmented region detecting section that detects pixels of a pigmented region of the cell image in the captured image, and generates a pigmented region image including the detected pixels of the pigmented region; and
an image segmentation section which overlays the edge image and the pigmented region image, removes extra edge portions in the edge image, performs completion of incomplete cell shapes in the edge image, whereby generates a new edge image, and performs a segmentation of the captured image based on the new edge image; and
a detection section which determines an intensity variance of pixels in each of segments in the captured image following a result of the segmentation, and determines cell segments and background segments in the captured image.

2. The cell monitoring device according to claim 1, further comprising:
a cell morphology detecting section that classifies, among a plurality of the cell image region, an image region in which the pigmented region is present as a target cell image, and classifies an image region in which the pigmented region is not present as a non-target cell image, and obtains a proportion of the non-target cell image in all of the cell images.

3. The cell monitoring device according to claim 1, further comprising:
a pigment value calculating section that calculates a pigment amount from an intensity value of the pigmented region in the cell image region.

4. The cell monitoring device according to claim 3, wherein a mean intensity value of the pigmented region is determined from the cell image region, the pigment amount is measured by extracting pigment from the cell of which the captured image is captured, a regression equation between the mean intensity value and the pigment amount per cell is built in advance and saved in a storage section, the pigment value calculating section determines the mean intensity value in the cell image, and the pigment amount per cell is determined using the regression equation.

5. A cell monitoring method, comprising:
an outline detecting process that detects edge pixels from a cell image in a captured image of cells arranged in single layer and generates an edge image including the detected edge pixels by an outline detecting section;
a pigmented region detecting process that detects pixels of pigmented region of the cell image in the captured image and generates a pigmented region image including the detected pixels of the pigmented region by a pigmented region detecting section; and
an image segmentation process which overlays the edge image and the pigmented region image, removes extra edge portions in the edge image, performs completion of incomplete cell shapes in the edge image, whereby generates a new edge image, and performs a segmentation of the captured image based on the new edge image by an image segmentation section; and
a detection process which determines an intensity variance of pixels in each of segments in the captured image following a result of the segmentation, and determines cell segments and background segments in the captured image by a detection section.

6. A program stored on a non-transitory computer-readable medium that causes a computer to execute as a cell monitoring device for monitoring the shape of a cell, the program causing the computer to function as:
an outline detecting section that detects edge pixels from a cell image in a captured image of cells arranged in a single layer and generates an edge image including the detected edge pixels;
a pigmented region detecting section that detects pixels of a pigmented region of the cell image in the captured image, and generates a pigmented region image including the detected pixels of the pigmented region;
an image segmentation section which overlays the edge image and the pigmented region image, removes extra edge portions in the edge image, performs completion of incomplete cell shapes in the edge image, whereby generates a new edge image, and performs a segmentation of the captured image based on the new edge image; and
a detection section which determines an intensity variance of pixels in each of segments in the captured image following a result of the segmentation, and determines cell segments and background segments in the captured image.

7. The cell monitoring device according to claim 2, further comprising:
a pigment value calculating section that calculates a pigment amount from an intensity value of the pigmented region in the cell image region.

8. A computer system to operate as a cell monitoring device for monitoring the shape of a cell comprising a program causing the computer to function as:
an outline detecting section that detects edge pixels from a cell image in a captured image of cells arranged in a single layer and generates an edge image including the detected edge pixels;
a pigmented region detecting section that detects pixels of a pigmented region of the cell image in the captured image, and generates a pigmented region image including the detected pixels of the pigmented region;
an image segmentation section which overlays the edge image and the pigmented region image, removes extra edge portions in the edge image, performs completion of incomplete cell shapes in the edge image, whereby generates a new edge image, and performs a segmentation of the captured image based on the new edge image; and a detection section which determines an intensity variance of pixels in each of segments in the captured image following a result of the segmentation, and determines cell segments and background segments in the captured image.

* * * * *